US009789162B2

(12) United States Patent
Baylink et al.

(10) Patent No.: US 9,789,162 B2
(45) Date of Patent: Oct. 17, 2017

(54) SYSTEMIC AND LOCAL EX VIVO GENE THERAPY OF THE SKELETON

(71) Applicants: The United States of America, as represented by the Department of Veterans Affairs, Washington, DC (US); Loma Linda University, Loma Linda, CA (US)

(72) Inventors: David Baylink, Redlands, CA (US); Kin-Hing William Lau, Redlands, CA (US); Wanqiu Chen, Loma Linda, CA (US); Xiao-Bing Zhang, Loma Linda, CA (US)

(73) Assignees: The United States of America as represented by the Department of Veteran Affairs, Washington, DC (US); Loma Linda University, Loma Linda, CA (US)

( * ) Notice: Subject to any disclaimer, the term of this patent is extended or adjusted under 35 U.S.C. 154(b) by 0 days.

(21) Appl. No.: 14/932,826

(22) Filed: Nov. 4, 2015

(65) Prior Publication Data
US 2016/0120944 A1 May 5, 2016

Related U.S. Application Data

(60) Provisional application No. 62/075,401, filed on Nov. 5, 2014.

(51) Int. Cl.
C12N 5/0789 (2010.01)
C12N 5/10 (2006.01)
C12N 15/63 (2006.01)
A61K 38/18 (2006.01)
C07K 14/49 (2006.01)
C12N 15/86 (2006.01)
C12N 7/00 (2006.01)
A61K 35/28 (2015.01)
A61K 47/48 (2006.01)
C12N 5/0775 (2010.01)
A61K 48/00 (2006.01)

(52) U.S. Cl.
CPC .......... A61K 38/1858 (2013.01); A61K 35/28 (2013.01); A61K 47/48084 (2013.01); A61K 47/48238 (2013.01); C07K 14/49 (2013.01); C12N 5/0663 (2013.01); C12N 7/00 (2013.01); C12N 15/86 (2013.01); A61K 48/00 (2013.01); C12N 2501/135 (2013.01); C12N 2510/00 (2013.01); C12N 2740/15043 (2013.01); C12N 2740/15071 (2013.01); C12N 2800/00 (2013.01)

(58) Field of Classification Search
None
See application file for complete search history.

(56) References Cited

U.S. PATENT DOCUMENTS 8,772,571 B2    7/2014  Lau et al.
2015/0240219 A1 8/2015  Baylink et al.

OTHER PUBLICATIONS

Saeed et al, Mesenchymal Stem Cells (MSCs) as skeletal Therapeutics—An Update. Journal of Biomedical Science, 2016. 23:14, 15 pages.*
Aiuti et al. "Correction of ADA-SCID by stem cell gene therapy combined with nonmyeloablative conditioning." Science 296, No. 5577 (2002): 2410-2413.
Aiuti et al. "Lentiviral hematopoietic stem cell gene therapy in patients with Wiskott-Aldrich syndrome." Science 341, No. 6148 (2013): 1233151.
Al-Zube et al., "Recombinant human platelet-derived growth factor BB (rhPDGF-BB) and beta-tricalcium phosphate/collagen matrix enhance fracture healing in a diabetic rat model." Journal of Orthopaedic Research 27:8: 1074-1081 (2009).
Blaise et al., "Do different conditioning regimens really make a difference?." ASH Education Program Book 2012, 1: 237-245 (2012).
Canalis et al., "Mechanisms of anabolic therapies for osteoporosis." New England Journal of Medicine 357.9: 905-916 (2007).
Cartier et al. "Hematopoietic stem cell gene therapy with a lentiviral vector X-linked adrenoleukodystrophy." Science 326, No. 5954 (2009): 818-823.
Cavazzana-Calvo et al. "Transfusion independence and HMGA2 activation after gene therapy of human [bgr]-thalassaemia." Nature 467, No. 7313 (2010): 318-322.
Chanda et al., "Therapeutic potential of adult bone marrow-derived mesenchymal stem cells in diseases of the skeleton." Journal of cellular biochemistry 111.2: 249-257 (2010).
Cole et al., "Whole bone mechanics and bone quality." Clinical Orthopaedics and Related Research 469.8: 2139-2149 (2011).
Ettinger et al., "Reduction of vertebral fracture risk in postmenopausal women with osteoporosis treated with raloxifene: results from a 3-year randomized clinical trial." Jama 282.7: 637-645 (1999).
Falahati, et al. "Chemoselection of allogeneic HSC after murine neonatal transplantation without myeloablation or post-transplant immunosuppression." Molecular Therapy 20, No. 11 (2012): 2180-2189.

(Continued)

Primary Examiner — Christopher M Babic
Assistant Examiner — Kimberly A Aron
(74) Attorney, Agent, or Firm — Klarquist Sparkman, LLP

(57) ABSTRACT

Methods are disclosed herein for increasing bone mass and strength or bone fracture healing in a subject. The methods include administering to the subject a therapeutically effective amount of multipotent stem cells, wherein each multipotent stem cell is transformed with a recombinant nucleic acid molecule comprising a heterologous promoter operably linked to a nucleic acid encoding platelet derived growth factor (PDGF) B, and wherein the multipotent stem cells express a sufficient amount of PDGFB to increase bone mass and strength or bone fracture healing. A lentiviral vector also is disclosed that includes a phosphoglycerate kinase-1 (PGK) promoter operably linked to a nucleic acid encoding PDGFB.

25 Claims, 11 Drawing Sheets

(56) References Cited

OTHER PUBLICATIONS

Fischbach et al., "Cell-based therapeutics: the next pillar of medicine." *Science translational medicine* 5.179: 179ps7-179ps7 (2013).
Hall et al., "Sca-1+ Hematopoietic Cell-based Gene Therapy with a Modified FGF-2 Increased Endosteal/Trabecular Bone Formation in Mice." *Molecular Therapy* 15.10: 1881-1889 (2007).
Hall et al., "Stem cell antigen-1 positive cell-based systemic human growth hormone gene transfer strategy increases endosteal bone resorption and bone loss in mice." *The journal of gene medicine* 13.2: 77-88 (2011).
Hall et al., "Stem cell antigen-1+ cell-based bone morphogenetic protein-4 gene transfer strategy in mice failed to promote endosteal bone formation." *The journal of gene medicine* 11.10: 877-888 (2009).
Johnell et al., "An estimate of the worldwide prevalence and disability associated with osteoporotic fractures." *Osteoporosis international* 17.12: 1726-1733 (2006).
Kasperk et al., "Interactions of growth factors present in bone matrix with bone cells: effects on DNA synthesis and alkaline phosphatase." *Growth factors* 3.2: 147-158 (1990).
Lau et al., "Marrow stromal cell-based cyclooxygenase 2 ex vivo gene-transfer strategy surprisingly lacks bone-regeneration effects and suppresses the bone-regeneration action of bone morphogenetic protein 4 in a mouse critical-sized calvarial defect model." *Calcified tissue international* 85.4: 356-367 (2009).
Luo, et al. "Microbiota from obese mice regulate hematopoietic stem cell differentiation by altering the bone niche." *Cell Metabolism* 22, No. 5 (2015): 886-894.
McClung et al., "Romosozumab in postmenopausal women with low bone mineral density." *New England Journal of Medicine* 370.5 (2014): 412-420.
Meng et al., "Efficient reprogramming of human cord blood CD34+ cells into induced pluripotent stem cells with OCT4 and SOX2 alone." *Molecular Therapy* 20.2: 408-416 (2012).
Mitlak et al., "The effect of systemically administered PDGF-BB on the rodent skeleton." *Journal of Bone and Mineral Research* 11.2: 238-247 (1996).
Mosekilde et al., "Biomechanical competence of vertebral trabecular bone in relation to ash density and age in normal individuals." *Bone* 8.2: 79-85 (1987).
Nevins et al., "Platelet-derived growth factor stimulates bone fill and rate of attachment level gain: results of a large multicenter randomized controlled trial." *Journal of periodontology* 76.12: 2205-2215 (2005).
Patel et al. "Outcomes of patients with severe combined immunodeficiency treated with hematopoietic stem cell transplantation with and without preconditioning." *Journal of Allergy and Clinical Immunology* 124, No. 5 (2009): 1062-1069.
Rachner et al., "Osteoporosis: now and the future." *The Lancet* 377.9773: 1276-1287 (2011).
Scott et al. "Gene therapy's out-of-body experience." *Nature Biotechnology* 34, No. 6 (2016): 600-607.
Solchaga et al., "Comparison of the effect of intra-tendon applications of recombinant human platelet-derived growth factor-BB, platelet-rich plasma, steroids in a rat achilles tendon collagenase model." *Journal of Orthopaedic Research* 32.1: 145-150 (2014).
Solchaga et al., "Safety of recombinant human platelet-derived growth factor-BB in Augment® Bone Graft." *Journal of tissue engineering* 3.1: 2041731412442668 (2012).
Taya, et al. "Depleting dietary valine permits nonmyeloablative mouse hematopoietic stem cell transplantation." *Science* (2016): aag3145.
Tobiume et al., "Serum Bone Alkaline Phosphatase Isoenzyme Levels in Normal Children and Children with Growth Hormone (GH) Deficiency: A Potential Marker for Bone Formation and Response to GH Therapy 1." *The Journal of Clinical Endocrinology & Metabolism* 82.7: 2056-2061 (1997).
Tyagi et al., "Estrogen deficiency induces the differentiation of IL-17 secreting Th17 cells: a new candidate in the pathogenesis of osteoporosis." *PloS one* 7.9: e44552 (2012).
Xian et al., "Matrix IGF-1 maintains bone mass by activation of mTOR in mesenchymal stem cells." *Nature medicine* 18.7: 1095-1101 (2012).
Zielske, et al. "In vivo selection of MGMT (P140K) lentivirus-transduced human NOD/SCID repopulating cells without pretransplant irradiation conditioning." *The Journal of Clinical Investigation* 112, No. 10 (2003): 1561-1570.

\* cited by examiner

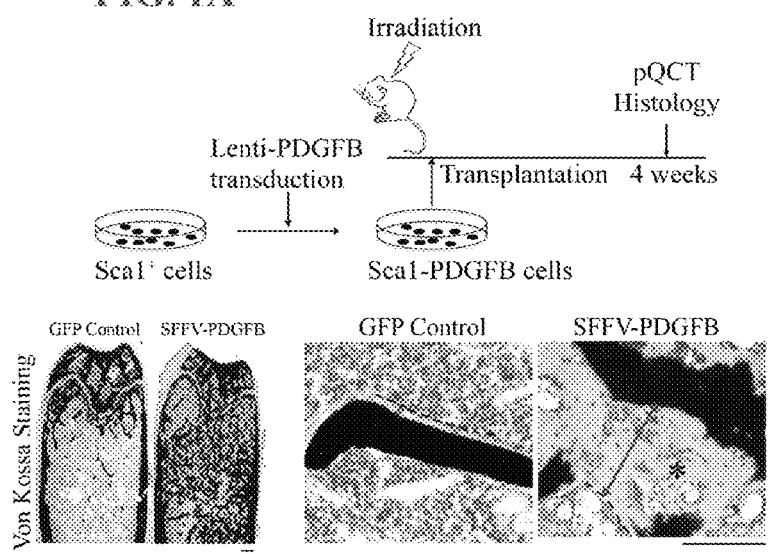
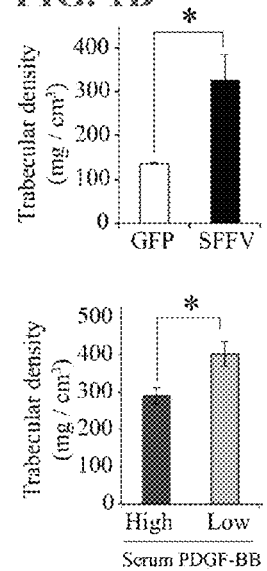
FIG. 1A  FIG. 1B  FIG. 1C  FIG. 1D  FIG. 1E

FIG. 2A
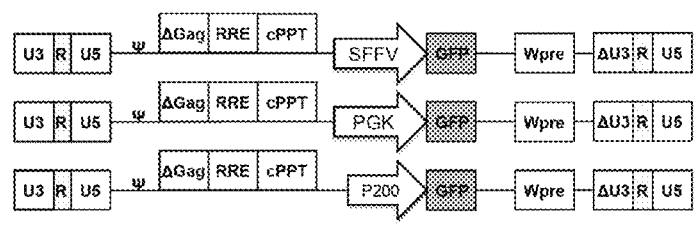
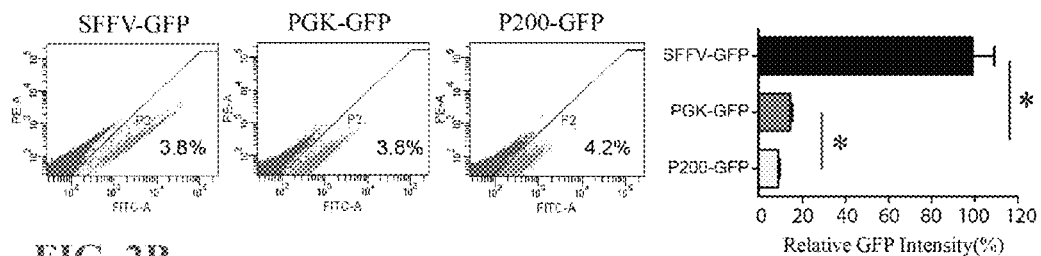
FIG. 2B
FIG. 2C

FIG. 4A
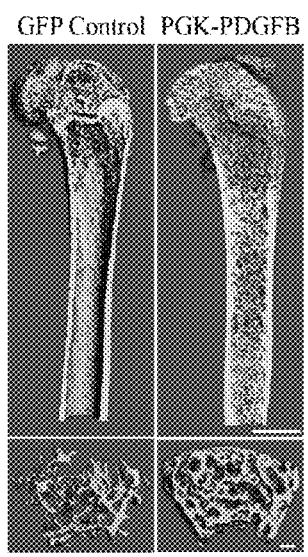
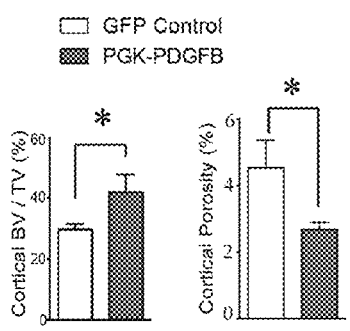
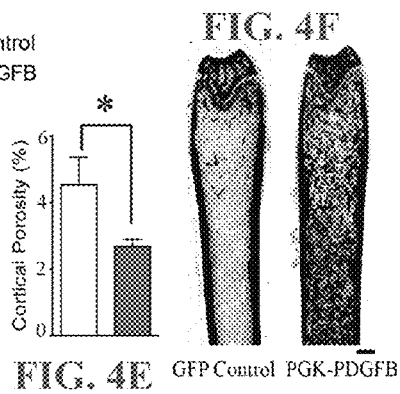
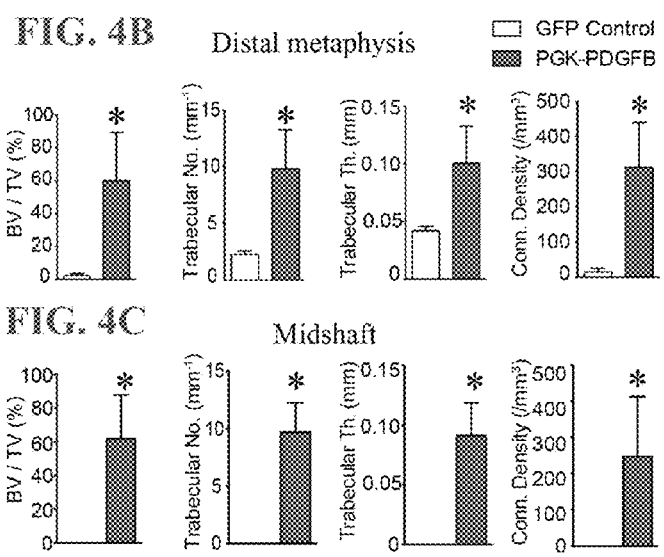
FIG. 4B Distal metaphysis
FIG. 4C Midshaft
FIG. 4D  FIG. 4E  FIG. 4F  FIG. 4G Von Kossa Staining  FIG. 4H

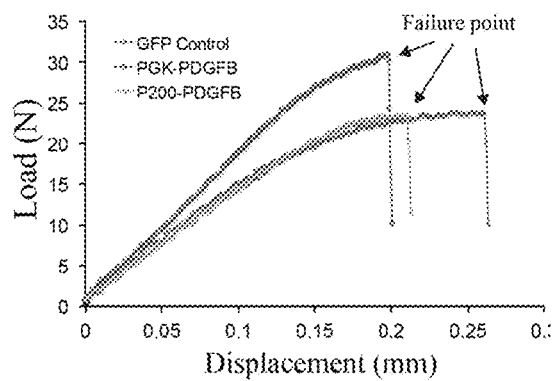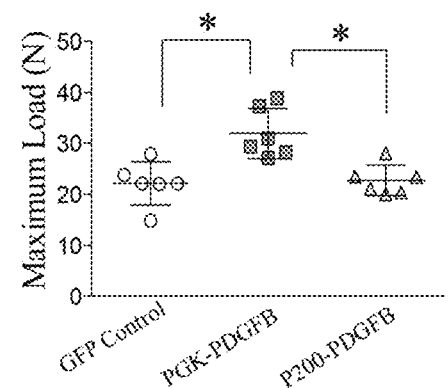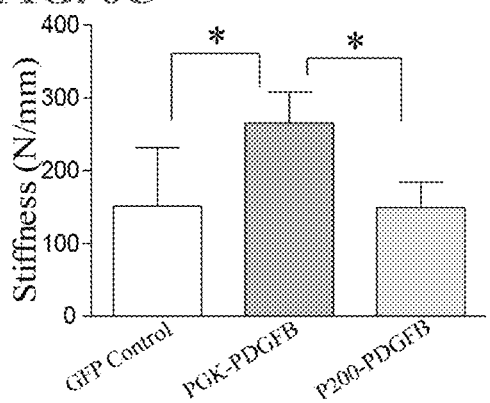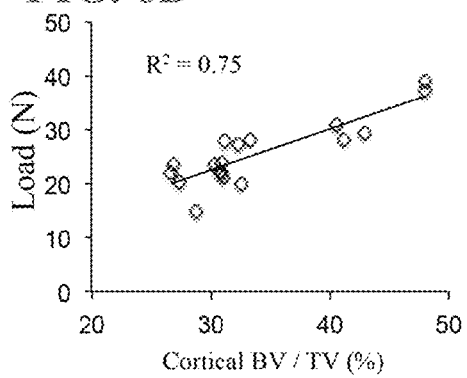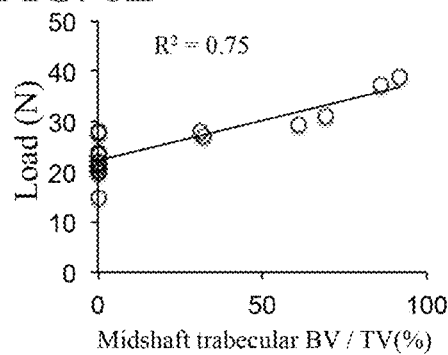

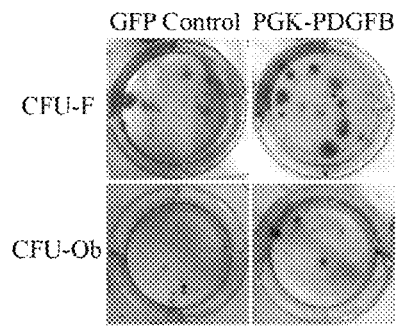
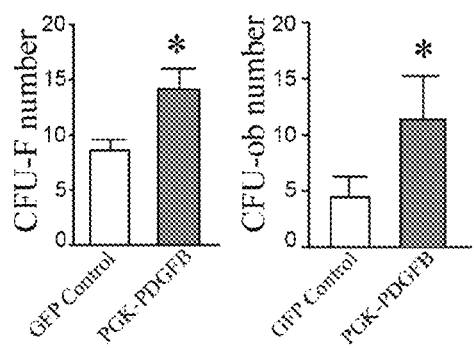
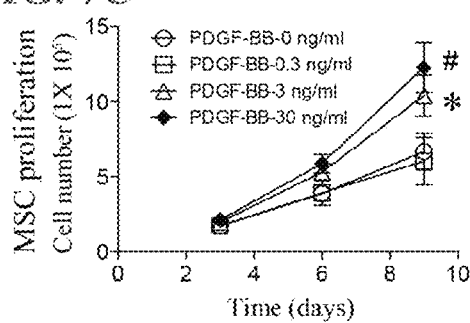
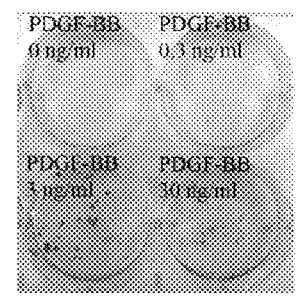
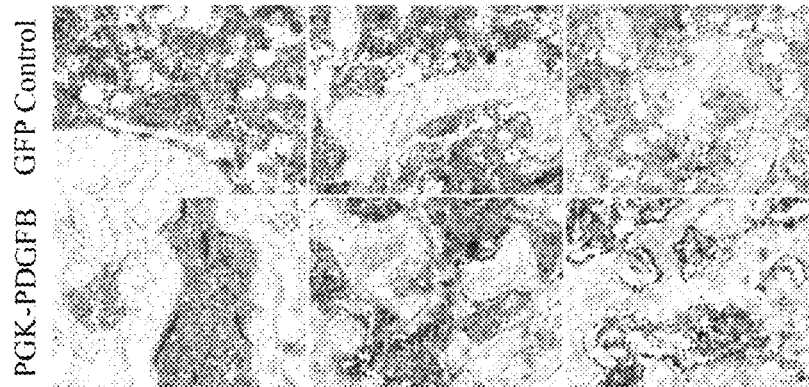
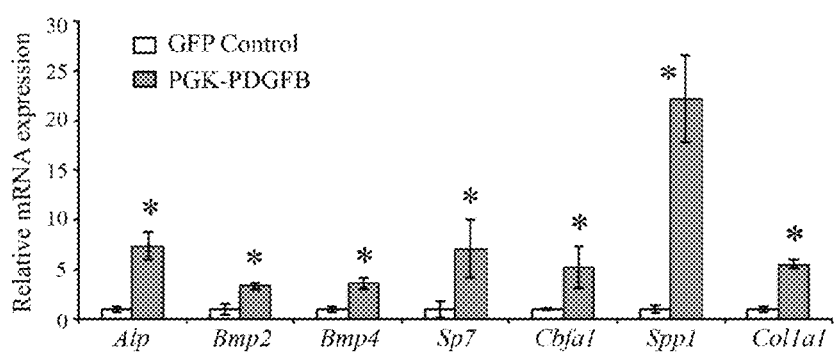

OVX+
GFP control

OVX+
PGK-PDGFB

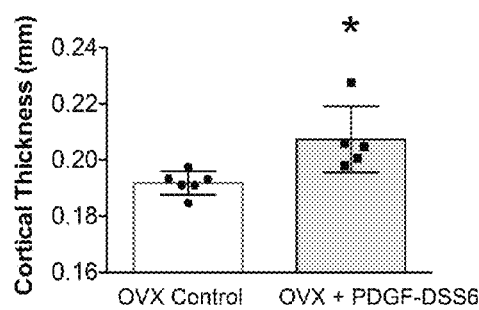 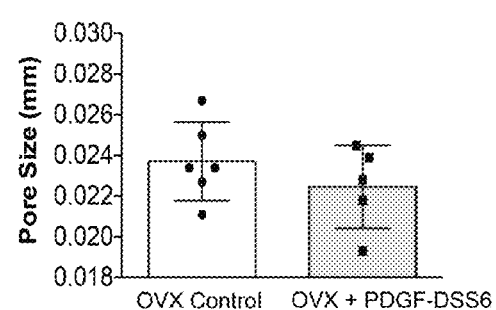
FIG. 11A
FIG. 11B

SYSTEMIC AND LOCAL EX VIVO GENE THERAPY OF THE SKELETON

CROSS REFERENCE TO RELATED APPLICATIONS

This claims the benefit of U.S. Application No. 62/075,401, filed Nov. 5, 2014, which is incorporated by reference herein.

ACKNOWLEDGMENT OF GOVERNMENT SUPPORT

This invention was made with government support under Grant No. W81XWH-08-1-0697 awarded by United States Army Medical Research Acquisition Activity. The government has certain rights in the invention.

FIELD

This disclosure relates to the field of osteogenesis, specifically to treating bone diseases and bone defects using platelet derived growth factor (PDGF) B.

BACKGROUND

Osteoporosis is a major public health problem, nationally and globally. Currently there are almost 10,000,000 osteoporosis related fractures annually worldwide. In the last two decades, the treatment of osteoporosis has shown dramatic advancement because of the development of effective anti-resorptive medications (Rachner et al., *Lancet.* 2011; 377 (9773):1276-87). These medications can decrease the fracture rate by as much as 50% (Ettinger et al., *JAMA: The Journal of the American Medical Association.* 1999; 282(7): 637-45). Later, parathyroid hormone (PTH) treatment was introduced, a therapy that stimulates bone formation as opposed to prior osteoporosis drugs, which retard bone loss. However the impact in terms of fracture reduction has been about the same as anti-resorptive drugs (Canalis et al., *The New England Journal of Medicine.* 2007; 357(9):905-16). More recently newer and stronger anabolic agents are now in clinical trials (McCLung et al., *The New England Journal of Medicine.* 2014; 370(5):412-20; Horwitz et al., *Journal of bone and mineral research: the official journal of the American Society for Bone and Mineral Research.* 2013; 28(11): 2266-76; Cabal et al., *Journal of bone and mineral research: the official journal of the American Society for Bone and Mineral Research.* 2013; 28(8):1830-6). However, none of these newer agents appear to have the potential to completely rejuvenate the osteoporotic skeleton back to a normal bone density. Each of these therapies also carries potential side-effects. A need remains for treatments for osteoporosis and other bone diseases and defects, such as fractures.

SUMMARY

Methods are disclosed herein for increasing bone mass and strength or enhancing bone fracture healing in a subject. The disclosed methods are advantageous as they avoid the formation of bones with low bone mineral density.

The method includes administering to the subject a therapeutically effective amount of multipotent stem cells, wherein each multipotent stem cell is transformed with a recombinant nucleic acid molecule comprising a heterologous promoter operably linked to a nucleic acid encoding platelet derived growth factor (PDGF)B, and wherein the multipotent stem cells express a sufficient amount of PDGFB to increase bone mass and strength or to enhance bone fracture healing, wherein the subject has a normal serum concentration of PDGF, a normal serum concentration of calcium, and/or a normal concentration of parathyroid hormone (PTH), following the administration. In several embodiments, the subject can be preconditioned prior to administration of the stem cells, for example, by total body or local irradiation or myeloablation to the subject before administration of the stem cells.

In some embodiments, the multipotent stem cells are hematopoietic stem cells. In additional embodiments, the multipotent cells are mixture of hematopoietic stem cells and mesenchymal stem cells. In some embodiments, the multipotent stem cells secrete about 1 to about 10 ng per $10^6$ cells of PDGF-BB into culture media in 24 hours, for example, when cultured at 37° C. at a cell density of about $1 \times 10^6$ cells per ml in Iscove's Modified Dulbecco Media (IMDM) supplemented with 10% fetal bovine serum, 100 ng/ml Stem Cell Factor/c-kit ligand (SCF), 100 ng/ml Thrombopoietin (Tpo), and 100 ng/ml Flt-3 ligand.

In additional embodiments, a lentiviral vector is disclosed that includes a phosphoglycerate kinase-1 (PGK) promoter operably linked to a nucleic acid encoding PDGFB.

The foregoing and other objects, features, and advantages of the invention will become more apparent from the following detailed description, which proceeds with reference to the accompanying figures.

BRIEF DESCRIPTION OF THE DRAWINGS

FIGS. 1A-1E. Transplantation of mouse Sca1$^+$ hematopoietic stem cells/progenitor cells transduced with a lentiviral vector expressing PDGFB under the control of the spleen focus-forming virus (SFFV) promoter (Lenti SFFV-PDGFB or SFFV-PDGFB) leads to massive trabecular bone formation but also induces osteomalacia. (A) Schematics of experimental design. After irradiation, animals were transplanted with Sca1$^+$ cells that were transduced with the Lenti SFFV-PDGFB vector or control lentiviral vector expressing green fluorescent protein (GFP) under control of the SFFV promoter (Lenti-SFFV-GFP), and bone tissue was analyzed 4 weeks later. (B) Peripheral Quantitative Computer Tomography (pQCT) analysis of femoral trabecular bone mineral density at 4 weeks after transplantation. Treatment with Lenti-SFFV-PDGFB Sca1$^+$ cells resulted in significant trabecular bone formation (*P<0.01). Control group: n=8; Lenti-SFFV-PDGFB group: n=13. (C) Von Kossa staining of mineralized bone in femur from mice treated with Sca1$^+$ cells transduced with Lenti-SFFV-PDGFB. Black color: mineralized bone. Scale bar: 200 µm. (D) High magnification images of Von Kossa staining of mineralized bone in femur. Osteomalacia-like phenotype was seen in mice treated with Sca1$^+$ cells transduced with Lenti-SFFV-PDGFB (indicated by *). Dash lines indicate the edge of osteoid. Red arrows indicate the osteoid width. Scale bar in right panel: 100 µm. (E) pQCT data from mice treated with Sca1$^+$ cells transduced with Lenti-SFFV-PDGFB was divided into low serum PDGF-BB (200-600 pg/ml, n=4) subgroup and high serum PDGF-BB (1000-3000 pg/ml, n=9) subgroup. Low serum PDGF-BB subgroup showed higher trabecular bone density than the high serum PDGF-BB subgroup (*P<0.05).

FIGS. 2A-2C. Reducing transgene expression by using weaker promoters, the PGK promoter and the truncated PGK (P200) promoter (with only ~200 bp proximal sequence of the PGK promoter). (A) Schematics of the constructed lentiviral vectors. Δ indicates the self-inactivation design with partially deleted U3 of the 3' long terminal repeat (LTR). cPPT, central polypurine tract; Wpre, Woodchuck Hepatitis Virus post-transcriptional regulatory element; RRE, rev-responsive element; ψ, packaging signal. SFFV, Spleen focus-forming virus U3 promoter; PGK, Phosphoglycerokinase promoter; P200, truncated PGK promoter. (B) FACS analysis of Sca1+ cells transduced with Lenti-SFFV-GFP, Lenti-PGK-GFP, or Lenti-P200-GFP with a low MOI of 0.1. Cells showed similar transduction efficiency. (C) Quantitative analysis of GFP intensity. With the similar transduction efficiency, GFP expression by PGK promoter was significantly lower than that driven by SFFV promoter (*P<0.05), and GFP expression by P200 promoter was significantly lower than that driven by PGK promoter (*P<0.05).

FIGS. 4A-4H. Sca1+ Lenti-PGK-PDGFB treatment promoted tremendous trabecular bone formation on the endosteum without inducing osteomalacia. (A) Representative μCT images of the femurs of GFP control and PGK-PDGFB treated mice at 12 weeks after transplantation. The bone volume and parameters of trabecular bone were analyzed at the distal femur metaphysis and midshaft. For top panel: scale bar=1 mm. For lower panel: scale bar=200 μm. (B) Parameters of the trabecular bone at the distal metaphysis of femurs as determined by μCT analysis. (n=6 for each group).*P<0.05. (C) Parameters of the trabecular bone at the midshaft of femurs as determined by μCT analysis. (n=6 for each group). *P<0.05. Cortical bone volume (D) and cortical porosity (E) as determined by μCT scan. *P<0.001. (F) Von Kossa staining showing increased bone formation in the marrow space in Lenti-PGK-PDGFB group. Scale bar: 500 μm. (G) High magnification images of Von Kossa stained femurs. Fully mineralized bone was seen in the mice treated with Sca1+ cells transduced with Lenti-PGK-PDGFB vector. Scale bar: 100 μm. (H) Quantification of osteoid width. ns: no significance.

FIGS. 6A-6E. Sca1+ Lenti-PGK-PDGFB treatment increased bone strength at the femoral midshaft. (A) A representative force-displacement curve for each test group. Three-point bending test at the midshaft of mouse femurs was used to measure bone strength. (B) Maximum load-to-failure was significantly increased in Sca1+ Lenti-PGK-PDGFB treated femurs when compared to Lenti-SFFV-GFP control or Lenti-P200-PDGFB treated femurs. *P=0.001. (C) Stiffness was significantly increased on Sca1+ Lenti-PGK-PDGFB treated femurs when compared to control or Lenti-P200-PDGFB group. *P=0.0037. (D) The maximum load-to-failure is positively correlated with the femur cortical bone volume ($R^2$=0.75, *P=0.0005). (E) The maximum load-to-failure is positively correlated with the trabecular bone volume in the midshaft ($R^2$=0.75, *P=0.0005).

FIGS. 7A-7F. Sca1+ Lenti-PDGF-BB promoted bone formation by increasing numbers of MSC, preosteoblasts and osteoblasts, as well as enhancing osteogenesis-related gene expression. (A) Representative images of CFU-F stained with crystal violet (top) and representative images of CFU-Ob stained with Alizarin red (bottom). CFU-F and CFU-Ob assays were conducted with bone marrow cells harvested from GFP control or PGK-PDGFB treated mice. (B) Quantification of the CFU-F and CFU-Ob numbers. GFP control vs. PGK-PDGFB, *P<0.05. (C) MSC proliferation curve. PDGF-BB used at 3 ng/ml or 30 ng/ml significantly increased MSC proliferation. GFP control vs. PDGF-BB (3 ng/ml or 30 ng/ml), *#P<0.05. (D) Alizarin red staining showing that the osteoblastic differentiation of MSCs was induced by PDGF-BB at 3 ng/ml, but was reduced by PDGF-BB at 30 ng/ml. Red stained are bone nodules after 3 weeks of culture. (E) Immunostaining for Runx2, Sp7 (also known as osterix), and osteocalcin on the sections of mouse femurs. Scale bar: 100 μm. (F) Real-time qPCR analysis of osteogenesis-related genes in the tibias. GFP control vs. PGK-PDGFB, *P<0.05.

FIGS. 11A-11B. Bar graphs of the MicroCT analysis of the midshaft of the tibias following 8-week treatment. (A) Cortical thickness; (B) Pore size. *P<0.05.

SEQUENCE LISTING

Figure 3A:
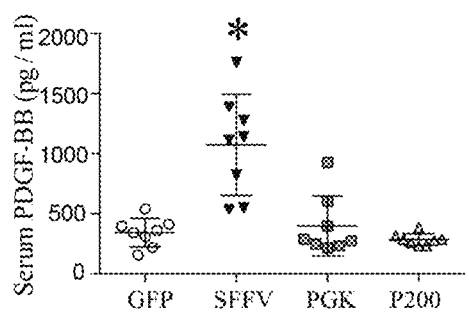
FIGS. 3A-3D. Sca1+ Lenti-PGK-PDGF-BB treatment increased serum levels of the two bone formation biomarkers, ALP and osteocalcin. (A) Serum PDGF-BB levels at 5 weeks post-transplantation. Serum PDGF-BB was significantly increased in the Sca1+ Lenti-SFFV-PDGFB group compared to all the other test groups (*P<0.001). Treatment with Sca1+ cells transduced with Lenti-PGK-PDGFB or Lenti-P200-PDGFB did not change serum PDGF-BB levels. N=8 in each group. (B) Serum alkaline phosphatase (ALP) activity after transplantation with Lenti-PGK-GFP control, Lenti PGK-PDGFB, or Lenti P200-PDGFB transduced Sca1+ cells. ALP activity was significantly higher in PGK-PDGFB group from 5 weeks to 11 weeks post-transplantation (*P<0.05). N=8 in each group. (C) Cytochemical staining of ALP in femur showed increased ALP activity in mice treated with Sca1+ cells transduced with Lenti-PGK-PDGFB vector. Scale bar: 200 μm. (D) Serum osteocalcin levels at 11 weeks post-transplantation. *P<0.01. N=8 in each group.

The nucleic and amino acid sequences listed are shown using standard letter abbreviations for nucleotide bases, and one or three letter code for amino acids, as defined in 37 C.F.R. 1.822. Only one strand of each nucleic acid sequence is shown, but the complementary strand is understood as included by any reference to the displayed strand.

The Sequence Listing is submitted as an ASCII text file 6915-93851-02_Sequence_Listing.txt, Nov. 3, 2015, 33.0 KB], which is incorporated by reference herein.

SEQ ID NO: 1 is an exemplary nucleic acid sequence encoding human PDGFB.

SEQ ID NO: 2 is an exemplary amino acid sequence for PDGFB.

SEQ ID NO: 3 is a nucleic acid sequence of a DNA targeting sequence.

SEQ ID NOs: 4-25 are the nucleic acid sequence of primers.

SEQ ID NO: 26 is the nucleic acid sequence of a wpre post-transcriptional regulatory element.

SEQ ID NOs: 27-34 are promoter sequences.

DETAILED DESCRIPTION

Substantial advances have been made in the last two decades in the management of osteoporosis. However none of the current medications eliminate the risk of fracture and rejuvenate the skeleton. To this end, it has been determined that a single IV injection of hematopoietic stem cells engineered to overexpress FGF2, a hematopoietic and mesenchymal stem cell mitogen (HSCs and MSCs), in myeloablated (preconditioned) mice resulted in a large increase in lamellar bone matrix formation. However, the bone can be fragile with severe osteomalacia and secondary hyperparathyroidism, and low bone mineral density. It is disclosed herein that PDGFB is an autocrine/paracrine mitogen for both HSCs and MSCs. A single IV injection of hematopoietic stem cells engineered to overexpress high levels of PDGFB, in preconditioned mice led to formation of bone that, similar to FGF2 expression, suffered from low bone mineral density. Surprisingly, modest overexpression of PDGFB increased bone formation, increased bone strength, increased trabecular connections, and decreased cortical porosity. Therapeutic methods based on this finding have wide applications including treatment of subjects undergoing bone marrow transplantation (which includes total body irradiation preconditioning), subjects with osteoporosis and other bone diseases, and subject with fractures and other bone defects.

Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

In order to facilitate review of the various embodiments of this disclosure, the following explanations of specific terms are provided:

Administration: The introduction of a composition into a subject by a chosen route. For example, if the chosen route is intravenous, the composition is administered by introducing the composition into a vein of the subject. If the chosen route is intraarticular, the composition is administered by introducing the composition into a joint of the subject. Administration can be systemic or local.

Animal: Living multi-cellular vertebrate organisms, a category that includes, for example, mammals and birds. The term mammal includes both human and non-human mammals. Similarly, the term "subject" includes both human and veterinary subjects.

Bone defect: Includes any disease, defect, or disorder which affects bone strength, function, and/or integrity, such as those resulting from injury, or a defect brought about during the course of surgery, infection, malignancy, or developmental malformation. Examples of bone defects include, but are not limited to, fractures (such as a critical defect or non-union fracture), dental or facial defects (such as cleft palate or facial or dental injuries or malformations). Other examples of bone defects include damage to bones resulting from diseases of bone fragility, such as osteoporosis, osteonecrosis, such as avascular osteonecrosis (AVN), osteogenesis inperfecta (OI), and malignancies and/or cancers of the bone such as a sarcoma, such as osteosarcoma.

Bone disease: Includes any disease or disorder which affects bone strength, function, and/or integrity, such as decreasing bone tensile strength and modulus. Examples of bone diseases include, but are not limited to, diseases of bone fragility, such as all types of osteoporosis according to etiology and pathogenesis, all types of metabolic bone diseases according to pathogenesis and etiology, osteonecrosis, and genetic diseases which result in abnormal bone formation such as McCune-Albright syndrome (MAS) and osteogenesis imperfecta. Other examples of bone diseases include malignancies and/or cancers of the bone such as a sarcoma, such as osteosarcoma.

Bone-forming cells and mineral forming cells: Cells having osteogenic potential. Examples include, but are not limited to: bone marrow stromal cells, osteoblasts, osteocytes, and dental pulp cells. "Osteogenesis" is the formation or production of bone.

Bone Healing and Fracture Healing: Bone heals (fuses) in a unique way compared with other connective tissues. Rather than develop scar tissue, it has the ability to regenerate itself completely. The majority of fractures heal by secondary fracture healing and that involves a combination of intramembranous and endochondral ossification. Without being bound by theory, it is generally believed that the fracture healing sequence involves five discrete stages of healing. This includes an initial stage in which a hematoma is formed and inflammation occurs; a subsequent stage in which cartilage begins to form and angiogenesis proceeds, and then three successive stages of cartilage calcification, cartilage resorption and bone deposition, and ultimately a more chronic stage of bone remodeling. Generally, committed osteoprogenitor cells and uncommitted, undifferentiated mesenchymal stem cells contribute to the process of fracture healing. Bone that forms by intramembranous ossification is found early and further from the site of the fracture, results in the formation of a hard callus, and forms bone directly without first forming cartilage. Generally, two weeks after fracture, cell proliferation declines and hypertrophic chondrocytes become the dominant cell type in the chondroid callus. The resulting endochondral bone is formed adjacent to the fracture site.

Bone Morphogenic Proteins (BMPs): A family of proteins, identified originally in extracts of demineralized bone that were capable of inducing bone formation at ectopic sites. BMPs are found in minute amounts in bone material (approximately 1 microgram/kg dry weight of bone). Most members of this family (with the exception of BMP-1) belong to the transforming growth factor-β family of proteins.

BMPs can be isolated from demineralized bones and osteosarcoma cells. They have been shown also to be expressed in a variety of epithelial and mesenchymal tissues in the embryo. BMPs are proteins which act to induce the differentiation of mesenchymal-type cells into chondrocytes and osteoblasts before initiating bone formation. They promote the differentiation of cartilage- and bone-forming cells near sites of fractures but also at ectopic locations. Some of the proteins induce the synthesis of alkaline phosphatase and collagen in osteoblasts. Some BMPs act directly on osteoblasts and promote their maturation. Other BMPs promote the conversion of typical fibroblasts into chondrocytes and are capable also of inducing the expression of an osteoblast phenotype in non-osteogenic cell types. BMPs include BMP-1 to BMP-15, such as BMP-2 and BMP-4. BMP-2 and BMP-4 and BMP-7 have been shown to promote bone formation. BMP2/4 is a hybrid gene in which the secretion signal of BMP4 is replaced with that of BMP2 (see Peng et al., *Mol. Therapy* 4:95-104, 2001, incorporated herein by reference).

cDNA (complementary DNA): A piece of DNA lacking internal, non-coding segments (introns) and regulatory sequences that determine transcription. cDNA is synthesized in the laboratory by reverse transcription from messenger RNA extracted from cells. cDNA can also contain untranslated regions (UTRs) that are responsible for translational control in the corresponding RNA molecule.

Conservative Substitutions: Modifications of a polypeptide that involve the substitution of one or more amino acids for amino acids having similar biochemical properties that do not result in change or loss of a biological or biochemical function of the polypeptide are designated "conservative" substitutions. These conservative substitutions are likely to have minimal impact on the activity of the resultant protein. Table 1 shows amino acids that can be substituted for an original amino acid in a protein, and which are regarded as conservative substitutions.

TABLE

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

One or more conservative changes, or up to ten conservative changes (such as two substituted amino acids, three substituted amino acids, four substituted amino acids, or five substituted amino acids, etc.) can be made in the polypeptide without changing a biochemical function of the osteogenic growth factor, such as Cox-2, LIM-1, FGF-2, BMP-2 or -4, or PDGF-BB.

Contacting: Placement in direct physical association. Includes both in solid and liquid form.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to, tumor necrosis factor-α, interleukin (IL)-6, IL-10, IL-12, transforming growth factor, and interferon-γ.

Degenerate variant: A polynucleotide encoding a polypeptide, such as a PDGFB polypeptide, that includes a sequence that is degenerate as a result of the genetic code. There are 20 natural amino acids, most of which are specified by more than one codon. Therefore, all degenerate nucleotide sequences are included as long as the amino acid sequence of the PDGFB polypeptide encoded by the nucleotide sequence is unchanged.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

DNA Nuclear Targeting Sequence (DTS): A specific DNA sequence or repeats of a DNA sequence that is needed to support nuclear import of an otherwise cytoplasmically localized plasmid DNA. Naturally occurring DNA sequences in the promoters of viruses or in the promoters of mammalian genes provide nuclear entry of the DNA containing a transgene by incorporating them into plasmid-expression vectors that can be expressed in a non-dividing cell. A non-limiting example is the DNA sequence from the SV40 genome, which contain the 72 bp enhancer repeats (5'-ATGCTTTGCA TACTTCTGCC TGCTGGGGAG CCTGGGGACT TTCCACACCC TAACTGACAC ACATTCCACA GCTGGTTGGT ACCTGCA-3', SEQ ID NO: 3). This SV40 DTS has been shown to support sequence-specific DNA nuclear import of plasmid DNA (see Dean et al., *Exp. Cell Res.* 253:713-722, 1999).

Expressed: The translation of a nucleic acid sequence into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Fibroblast Growth Factor (FGF): A large family of multigene family of growth factors that is a pleiotropic regulator of the proliferation, differentiation, migration, and survival in a variety of cell types (see Bikfalvi et al., Endocrine Rev. 18:26-45, 1997). The proteins in this family are 16-18 kDa proteins controlling normal growth and differentiation of mesenchymal, epithelial, and neuroectodermal cell types.

Two main groups of FGF are known. One type of FGF was isolated initially from brain tissue and identified by its ability to enhance proliferation of murine fibroblasts. Due to its basic pI the factor was named basic FGF or FGF-2 (see below). This factor is the prototype of the FGF family. Another factor, isolated also initially from brain tissues, has the ability to enhance proliferation of myoblasts. This factor is termed acidic FGF (aFGF). Other proteins in the FGF family are int-2 (FGF-3), FGF-4 FGF-5, FGF-6, K-FGF (FGF-7) and FGF-8. All of these factors are products of different genes. Some FGF are not secreted (FGF-2) while others (FGF-3, FGF-4, FGF-5 and FGF-6) have a signal sequence and therefore are secreted. Presently there are 23 factors identified as an FGF (numbered FGF-1 to FGF-23).

Basic fibroblast growth factor ("b-FGF" or "FGF-2") is a potent stimulator of angiogenesis (see D'Amore and Smith, Growth Factors 8:61-75, 1993) and hematopoiesis in vivo (see Allouche and Bikfalvi, Prog. Growth Factor Res. 6:35-48, 1995). FGF-2 is also involved in organogenesis (Martin, Genes Dev. 12:1571-1586, 1998), vascularization (see Friesel and Maciag, FASEB J. 9:919-925, 1995), and wound healing (see Ortega et al., Proc. Natl. Acad. Sci. USA 95:5672-5677, 1998), and plays an important role in the differentiation and/or function of various organs, including the nervous system (see Ortega et al., Proc. Natl. Acad. Sci. USA 95:5672-5677, 1998), and the skeleton (see Montero et al., J. Clin. Invest. 105:1085-1093, 2000). Because of its angiogenic and anabolic properties, FGF-2 has been shown to be involved in wound healing.

Fracture: A medical condition in which a bone is cracked or broken; a break in the continuity of a bone. Fractures may be classified as closed or open. A closed fracture is one in which the skin is intact; an open (or compound) fracture is one in which the bone is in contact with the air (such as piercing the skin or due to severe tissue injury). Fractures are also classified as simple or multi-fragmentary. A simple fracture occurs along only one line (such as splitting a bone into two pieces), while a multi-fragmentary fracture splits a bone into multiple pieces (such as three or more pieces). Other types of fracture include complete, incomplete, linear, transverse, oblique, compression, spiral, comminuted, and compacted fractures. Additional fractures include a critical defect (such as when part of a bone is lost or removed) and a non-union fracture (such as when the ends of the fracture are not in contact with each other).

Heterologous: A heterologous sequence is a sequence that is not normally (i.e. in the wild-type sequence) found adjacent to a second sequence. In one embodiment, the sequence is from a different genetic source, such as a virus or organism, than the second sequence.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Inhibiting or treating a disease: Inhibiting the full development of a disease or condition or accelerating healing, for example, in a subject who is at risk for a disease (for example, osteoporosis or a fracture). "Treatment" refers to a therapeutic intervention that ameliorates a sign or symptom of a disease or pathological condition after it has begun to develop. Treatment can also refer to acceleration of fracture healing. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, such as pain, a shortened recovery time or an improvement in the overall health or well-being of the subject, or by other parameters well known in the art that are specific to the particular disease.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Mammal: This term includes both human and non-human mammals. Similarly, the term "subject" includes both human and veterinary subjects.

Mesenchymal Stem Cell: A multipotent stem cell capable of giving rise to differentiated cells in multiple mesenchymal lineages, specifically to osteoblasts, adipocytes, myoblasts, chondroblasts, and fibroblasts. Generally, mesenchymal stem cells also have one or more of the following properties: an ability to undergo asynchronous, or asymmetric replication (where the two daughter cells after division can have different phenotypes); extensive self-renewal capacity; and clonal regeneration of the tissue in which they exist, for example, the non-hematopoietic cells of bone marrow.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand." Sequences on a nucleic acid sequence which are located 5' to sequence of interest are referred to as "upstream sequences;" sequences a nucleotide sequence which are located 3' to the sequence of interest are referred to as "downstream sequences."

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together, such as in a wild-type gene. This includes nucleic acid vectors comprising an amplified or assembled nucleic acid which can be used to transform a suitable host cell. In one example, a recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, such as by genetic engineering techniques. A host cell that includes the recombinant nucleic acid is referred to as a "recombinant host cell." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence. Thus, the two sequences are complementary.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Osteoblast: A mononucleated cell that is responsible for bone formation. Osteoblasts produce osteoid, which is composed mainly of Type I collagen. Osteoblasts are also responsible for mineralization of the osteoid matrix. Bone is a dynamic tissue that is constantly being reshaped by osteoblasts, which build bone, and osteoclasts, which resorb bone. Osteoblasts arise from osteoprogenitor cells located in the periosteum and the bone marrow. Osteoprogenitors are immature progenitor cells that express the master regulatory transcription factor Cbfa1/Runx2. Once osteoprogenitors start to differentiate into osteoblasts, they begin to express a range of markers including osterix, collagen type 1, alkaline phosphatase, osteocalcin, osteopontin, and osteonectin.

Osteoclast: A type of bone cell that removes bone tissue by removing its mineralized matrix by a process of bone resorption. Osteoclasts are formed by the fusion of cells of the monocyte-macrophage cell line. Osteoclasts are characterized by high expression of tartrate resistant acid phosphatase and cathepsin K.

Osteoconduction: The scaffold function provided by the transplanted extracellular bone matrix which facilitates cell attachment and migration, and therefore the distribution of a bone healing response throughout the grafted volume. This property is likely dependent on adhesion molecules within bone matrix such as: collagens, fibronectin, vitronectin, osteonectin, osteopontin, osteocalcin, proteoglycans and others. Growth factors in the matrix may also play a role.

Osteocyte: Mature, non-dividing bone cells that are housed in their own lacunae (small cavities in the bone). Osteocytes are derived from osteoblasts and they represent the final stage of maturation of the bone cell lineage. They are less active than osteoblasts, and although they are not responsible for a net increase in bone matrix, they are essential to the maintenance and routine turnover of the matrix. The narrow, cytoplasmic processes of osteocytes remain attached to each other and to osteoblasts through canaliculi (small channels in the bone).

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Biodegradable and biocompatible polymer scaffolds may be used as carriers for gene delivery (see Jang et al., Expert Rev. Medical Devices 1:127-138, 2004). These scaffolds usually contain a mixtures of one or more biodegradable polymers, for example and without limitation, saturated aliphatic polyesters, such as poly(lactic acid) (PLA), poly(glycolic acid), or poly(lactic-co-glycolide) (PLGA) copolymers, unsaturated linear polyesters, such as polypropylene fumarate (PPF), or microorganism produced aliphatic polyesters, such as polyhydroxyalkanoates (PHA), (see Rezwan et al., Biomaterials 27:3413-3431, 2006; Laurencin et al., Clin. Orthopaed. Rel. Res. 447:221-236). By varying the proportion of the various components, polymeric scaffolds of different mechanical properties are obtained. A commonly used scaffold contains a ratio of PLA to PGA is 75:25, but this ratio may change depending upon the specific application. Other commonly used scaffolds include surface bioeroding polymers, such as poly(anhydrides), such as trimellitylimidoglycine (TMA-gly) or pyromellitylimidoalanine (PMA-ala), or poly(phosphazenes), such as high molecular weight poly(organophasphazenes) (P[PHOS]), and bioactive ceramics. An advantage of these polymeric carriers is that they represent not only a scaffold but also a drug or gene delivery system.

Platelet Derived Growth Factor (PDGF): A dimeric glycoprotein composed of two A (-AA) or two B (-BB) chains or a combination of the two (-AB) that binds to a platelet derived growth factor receptor. PDGF is a required element in cellular division for fibroblasts. Binding of a PDGF to a PDGF receptor results in dimerization of the receptor, and auto-phosphorylation of several sites on their cytosolic domains, which in turn serves to mediate binding of cofactors and subsequently activate signal transduction through the PI3K pathway or through reactive oxygen species (ROS)-mediated activation of the STAT3 pathway.

There are two genes that encode PDGF, PDGFA (which encodes PDGFA) and PDGFB (which encodes PDGFB, located at 22q13.1 in the human genome. An exemplary mRNA encoding human PDGFB is set forth in GENBANK Accession No. NM_002608.2, and an exemplary human PDGFB protein is set forth as GENBANK Accession No. NP_002599, which are both incorporated herein by reference. Other mammalian PDGFB proteins include, but are not limited to mouse PDGFB (GENBANK Accession No, XM_006520591.1 (mRNA), XP_00652065301 (protein)), cow PDGFB (GENBANK Accession No. NM_001017953.2 (mRNA), NP_001017953.2 (protein)), monkey PDGFB (GENBANK Accession No. XM_001097395.2 (mRNA), XP_001097395 (protein)), dog PDGFB (GENBANK Accession No. NM_001003383.1 (mRNA), NP_001003383.1 (protein), rat PDGFB (GENBANK Accession No. L40991.1 (mRNA), AAA70048.1 (protein)).

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (for example, a cDNA) independent of other sequences. The nucleotides can be ribonucleotides, deoxyribonucleotides, or modified forms of either nucleotide. The term includes single- and double-stranded forms of DNA. A PDGF-B polynucleotide is a nucleic acid encoding a PDGF-B polypeptide.

Polypeptide: Any chain of amino acids, regardless of length or post-translational modification (such as glycosylation or phosphorylation). In one embodiment, the polypeptide is PDGFB polypeptide. A "residue" refers to an amino acid or amino acid mimetic incorporated in a polypeptide by an amide bond or amide bond mimetic, the "position" of the residue indicates its place in the amino acid sequence. A polypeptide has an amino terminal (N-terminal) end and a carboxy terminal end.

Polypeptide modifications: The polypeptides disclosed herein include synthetic embodiments of polypeptides such as PDGFB. In addition, analogs (non-peptide organic molecules), derivatives (chemically functionalized peptide molecules obtained starting with the disclosed peptide sequences) and variants (homologs) of these proteins can be utilized in the methods described herein. Each polypeptide is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into peptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of polypeptide. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press, Buffalo Grove, Ill., pp. 165-174 and *Principles of Pharmacology* Munson (ed.) 1995, Ch. 102, for descriptions of techniques used in CADD. Also included are mimetics prepared using such techniques.

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

In some non-limiting examples, the promoter can be, for example, a Phosphoglycerate Kinase-1 (PGK) promoter, a beta-globin promoter, a human cytomegalovirus (CMV) promoter, a Murine Stem Cell Virus (MSV) promoter, a Human elongation factor-1 alpha (EF1alpha) promoter, a ubiquitous chromatin opening elements (UCOE) promoter, a metallothionein promoter, a retrovirus long terminal repeat; a adenovirus late promoter, vaccinia virus 7.5K promoter, or spleen focus-forming virus (SFFV) promoter. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells. The promoter can be, for example, derived from the genome of mammalian cells or from mammalian viruses.

Protein purification: The PDGFB polypeptides and disclosed herein can be purified by any of the means known in the art. See, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Purified: The term purified does not require absolute purity; rather, it is intended as a relative term. Thus, for example, a purified peptide or polynucleotide preparation is one in which the peptide or polynucleotide is more enriched than the peptide or polynucleotide is in its natural environment within a cell. In one embodiment, a preparation is purified such that the protein or polynucleotide represents at least 50% of the total peptide or polynucleotide content of the preparation.

Repair: New bone formation which is sufficient to at least partially fill a void or structural discontinuity at the site of a bone defect. The term repair does not require a process of complete healing or a treatment which is 100% effective at restoring a defect to its pre-defect state.

Retrovirus: Any virus in the family Retroviridae. These viruses have similar characteristics, specifically they share a replicative strategy. This strategy includes as essential steps reverse transcription of the virion RNA into linear double-stranded DNA, and the subsequent integration of this DNA into the genome of the cell. All native retroviruses contain three major coding domains with information for virion proteins: gag, pol and env. In one embodiment, a retrovirus is an avian sarcoma and leukosis virus, a mammalian B-type virus, a Murine leukemia-related virus, a Human T-cell leukemia-bovine leukemia virus, a D-type virus, a lentivirus, or a spumavirus. In another embodiment, the virus is a Rous sarcoma virus, a mouse mammary tumor virus, a human T-cell leukemia virus, a Mason-Pzifer monkey virus, a human immunodeficiency virus, a human foamy virus, or a Molony Leukemia Virus (MLV). A native retrovirus generally contains three genes known as "gag," "pol," and "env." A replication defective retrovirus does not contain genetic sequences coding for these three retroviral genes: gag, pol and env.

Safe harbor: A locus in the genome where a polynucleotide may be inserted without causing deleterious effects to the host cell. Examples of safe harbor loci known to exist within mammalian cells may be found within the AAVS 1 gene, the CYBL gene, and the CCR5 gene.

Selectively hybridize: Hybridization under moderately or highly stringent conditions that exclude non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (such as GC versus AT content), and nucleic acid type (such as RNA versus DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., Sambrook et al. (Molecular Cloning: A Laboratory Manual, 4$^{th}$ ed, Cold Spring Harbor, N.Y., 2012). Washing can be carried out using only one of these conditions, e.g. high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a PDGFB polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a PDGFB polypeptide are typically characterized by possession of at least about 75%, for example at least about 80%, 90%, 95%, 96%, 97%, 98% or 99% sequence identity counted over the full length alignment with the amino acid sequence of PDGFB using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Another indicia of sequence similarity between two nucleic acids is the ability to hybridize. The more similar are the sequences of the two nucleic acids, the more stringent the conditions at which they will hybridize. Substantially similar or substantially identical nucleic acids (and to subsequences thereof), such as PDGFB nucleic acids, include nucleic acids that hybridize under stringent conditions to any of these reference polynucleotide sequences. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013).

For purposes of the present disclosure, "stringent conditions" encompass conditions under which hybridization will only occur if there is less than 25% mismatch between the hybridization molecule and the target sequence. "Stringent conditions" can be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid.

In nucleic acid hybridization reactions, the conditions used to achieve a particular level of stringency will vary depending on the nature of the nucleic acids being hybridized. The length, degree of complementarity, nucleotide sequence composition (e.g., GC v. AT content), and nucleic acid type (e.g., RNA versus DNA) of the hybridizing regions of the nucleic acids all influence the selection of appropriate hybridization conditions. Additionally, whether one of the nucleic acids is immobilized, for example, on a filter can impact the conditions required to achieve the desired stringency.

A specific example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, or each of the conditions can be used, such as for 10-15 minutes each, in the order listed above, repeating any or all of the steps listed. However, as mentioned above, optimal conditions will vary, depending on the particular hybridization reaction involved, and can be determined empirically.

Spinal fusion: A technique in which one or more of the vertebra of the spine are united together ("fused") so that motion is severely limited or no longer occurs between the vertebra. Spinal fusion can be preformed for the treatment of a fractured (broken) vertebra, the correction of deformity (spinal curves such as scoliosis or slippages such as spondylolisthesis), the elimination of pain from painful motion, the treatment of instability, and the treatment of some cervical disc herniations.

Stem cell: A cell that can generate a fully differentiated functional cell of more than one given cell type. The role of stem cells in vivo is to replace cells that are destroyed during the normal life of an animal. In some embodiments, stem cells (for example, embryonic stem cells) can divide without limit and are totipotent or pluripotent. After division, a pluripotent stem cell may remain as a pluripotent stem cell, become a multipotent stem cell, or proceed to terminal differentiation. A multipotent stem cell is a stem cell that can generate a fully differentiated cell of more than one given cell type, but is not pluripotent. In one example, a multipotent stem cell includes a mesenchymal cell that can self-renew and can generate bone-forming or mineral-forming cells, such as osteoblasts. In another example, a multipotent stem cell is a hematopoietic stem cell. Multipotent stem cells may be derived from tissues of a post-natal subject, for example, from bone marrow and adipose tissue; examples of multipotent stem cells include mesenchymal stem cells and adipose-derived stem cells. A hematopoietic stem cell refers to a heterogenous class of cells typically isolated from bone marrow, cord blood, peripheral blood or embryonic liver. Hematopoietic stem cells are multipotent stem cells that give can differentiate into to hematopoietic cells, including red and white blood cells. Additionally, certain hematopoietic stem cells can be induced to differentiate into cells of various lineages and germ layers, including one or more of muscle lineage cells, neural lineage cells and osteoblast lineage cells.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to accelerate bone fracture healing. When administered to a subject, a dosage will generally be used that will achieve target tissue concentrations (for example, in bone) that has been shown to achieve a desired in vitro effect.

It is understood that multiple administrations of the disclosed agents or compositions may be required to achieve the desired effect. Thus, a therapeutically effective amount encompasses a fractional dose that contributes in combination with previous or subsequent administrations to attaining the desired bone fracture healing or increase in bone strength. For example, a therapeutically effective amount of an agent can be administered in a single dose, or in several doses, for example daily, during a course of treatment. However, the therapeutically effective amount can depend on the subject being treated, the severity and type of the condition being treated, and the manner of administration.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Transgene: An exogenous gene.

Transposon: Mobile elements that transpose gene segments in the genome. Tc1-like transposons, including sleeping beauty, are members of a superfamily of eukaryotic transposons that transpose in a "cut-and-paste" manner that requires the binding of an element-encoded enzyme, the transposase, to short inverted repeat/direct repeat (IR/DR) sequences flanking the element (see Plasterk, Curr. Top. Microbiol. Immunol. 204:125-143, 1996). Most of these elements integrate stably into TA-based target sites, which are duplicated upon insertion. Accordingly, the Tc1-like transposase has the unique ability to catalyze the excision of the DNA region flanked by the transposon elements in a plasmid DNA and promote its integration into the genome at TA target dinucleotide sites. Thus, this transposon system can be engineered into a gene transfer plasmid vector system that leads to stable integration with relative site-specificity (such as in TA dinucleotide sites).

The Tc1-like transposable elements in vertebrates are defective due to accumulation of mutations caused by a process known as "vertical inactivation" and are not functional (see Vos et al., Genes Dev. 10:755-761, 1996). However, Ivics and coworkers (see Cell 91:501-510, 1997) have reconstructed or "resurrected" a Tc1-like transposase from fish by correcting key mutations and referred to this molecularly reconstructed, functional fish Tc1-like transposon system as the "Sleeping Beauty" transposon system. This system has been shown to effectively transpose exogenous extrachromosomal DNA (supercoiled plasmid DNA) into genomic loci of human and mouse embryonic cells (see Ivics, et al., Cell 91:501-510, 1997, Luo et al., Proc. Natl. Acad. Sci. USA 95:10769-10773, 1998).

The first generation Sleeping Beauty plasmid vector system contained two plasmids: one plasmid expressed the reconstructed Tc1-like Sleeping Beauty transposase, and the other plasmid contained the Tc1-like transposon IR/DR elements flanking the transgene-of-interest. A single plasmid including both elements (the transposase and the IR/DR elements), which is a "Sleeping Beauty" Tc1-like transposon-based vector is referred to as the Prince Charming (pPC) vector system (Harris et al., Anal. Biochem. 310:15-26, 2002, incorporated herein by reference).

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival or mobility. The treatment may be assessed by objective or subjective parameters; including the results of a physical examination or laboratory tests.

Upregulated or increase: When used in reference to the expression of a nucleic acid molecule, such as a gene, or to an amount of a protein or other molecule, "increase" refers to any process which results in an increase in production of a molecule of interest.

An upregulation or an increase includes a detectable increase in the amount of a molecule in a sample. In certain examples, the amount is increased by at least 2-fold, for example at least 3-fold or at least 4-fold, as compared to a control (such an amount of present in an untreated cell).

Vector: A nucleic acid molecule as introduced into a cell, thereby producing a transformed host cell. A vector may include nucleic acid sequences that permit it to replicate in a host cell, such as an origin of replication. A vector may also include one or more selectable marker genes and other genetic elements known in the art. Vectors can be viral vectors, such as adenoviral, retroviral, or lentiviral vectors. Vectors can be non-viral vectors, such as Sleeping Beauty plasmids or Prince Charming plasmids.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Cells and Vectors

The method disclosed herein utilizes multipotent stem cells that can localize to bone marrow and express a sufficient amount of heterologous platelet derived growth factor (PDGF) B. Generally, a therapeutically effective amount of the cells are administered to the subject, such that the amount of PDGFB produced by the cells is sufficient to increase bone mass and strength and/or bone fracture healing.

In some embodiments, the multipotent stem cells produce about 1 to about 10 ng per $10^6$ cells of PDGFB in 24 hours. In other embodiments, the multipotent stem cells produce about 2 to about 6 ng per $10^6$ cells of PDGFB in 24 hours. In specific non-limiting examples, the multipotent stem cells produce about 1 ng of PDGFB per $10^6$ cells, about 2 ng of PDGFB per $10^6$ cell, about 3 ng of PDGFB per $10^6$ cells, about 4 ng of PDGFB per $10^6$ cells, about 5 ng of PDGFB per $10^6$ cells, about 6 ng of PDGFB per $10^6$ cells, about 7 ng of PDGFB per $10^6$ cells, about 8 ng of PDGFB per $10^6$ cells, about 9 ng of PDGFB per $10^6$ cells, or about 10 ng of PDGFB per $10^6$ cells. In further embodiments, the serum level of PDGF of the subject is normal following the administration of the cells. Thus, if the subject is human, the serum level of PDGFB can be from 0.1 to 15 ng/ml following administration of the cells.

In some embodiments, the multipotent stem cells are obtained from the same subject to whom the cells are to be administered, and thus are autologous. The hematopoietic stem cells can also be from a different subject, and be allogeneic. Typically, donor(s) and recipient(s) are immunologically compatible. Thus the multipotent stem cells can be allogeneic.

A number of tissues can provide a source of stem cells for use in the compositions and methods described herein, and stem cells can be isolated from these tissues using isolation procedures known in the art. One significant feature of these cells is that they are able to home to, engraft, continue to produce progeny cells (including additional stem cells), and reside in the bone marrow following transplantation.

In some embodiments, the multipotent stem cells are hematopoietic stem cells, including CD34 positive cells isolated from the umbilical cord blood, the bone marrow, and the peripheral blood. A non-limiting example of such a murine hematopoietic stem cell is a Sca-$1^+$ stem cell population described below. Such hematopoietic stem cells can be isolated from the bone marrow, from umbilical cord vein blood or from the peripheral blood of humans, for example, following treatment with granulocyte-macrophage colony-stimulating factor (GM-CSF) and or erythropoietin (EPO).

In some examples, the multipotent stem cells are human bone marrow derived stem cells capable of homing to the bone marrow and giving rise to osteoblast lineage. These cells can be hematopoietic stem cells, such as cells characterized as $CD34^+$, $lin^-$ cells, more specifically $CD34^+$, $AC133^+$, $lin^-$, $CD45^-$, $CXCR4^+$ (Kucia et al., Leukemia 19:1118-1177, 2005). Hematopoietic stem cells that are $CD34^+/CD38^-$ cells (Chen et al., Stem Cells 15:368-377, 1997); $CD73^+$, $STRO-1^+$, $CD105^+$, $CD34^-$, $CD45^-$, $CD144^-$ cells (Tuli et al., Stem Cells 21:681-693); and $CD29^+$, $CD63^+$, $CD81^+$, $CD122^+$, $CD164^+$, $cMet^+$, bone morphogenetic protein receptor $1B^+$, and neurotrophic tyrosine kinase receptor $3^+$ and $CD34^-$, $CD36^-$, $CD45^-$, $CD117^-$ ($cKit^-$), and $HLA-DR^-$ (D'Ippolito et al., Journal of Cell Science 117:2971-2981, 2004) are also of use.

In certain embodiments, the hematopoietic stem cells express CXCR4, which facilitates homing to the bone marrow. Such cells are capable of expressing heterologous nucleic acid molecules that encode PDGFB at appropriate levels, home to bone marrow throughout the entire skeleton, undergo stem cell renewal, and give rise to cells of the osteoblastic lineage.

A population of cells enriched in hematopoietic stem cells can be administered to the subject. For example, the population can be enriched by treating a population of cells in vivo or in vitro with a growth factor that promotes expansion of hematopoietic lineage cells, such as erythropoietin (EPO), granulocyte colony stimulating factor (G-CSF), and/or granulocyte macrophage colony stimulating factor (GM-CSF). The population of cells can be treated either before or after isolation from bone marrow, cord blood or peripheral blood. Thus, the population of cells can be enriched for hematopoietic stem cells by administering EPO, G-CSF and/or GM-CSF to a donor subject prior to isolating hematopoietic stem cells from bone marrow or peripheral blood. These cells express heterologous PDGFB.

The cells can also contain any fractions of marrow stem cells, osteoblast cells and mesenchymal stem cells. The cells can also be mesenchymal stem cells, cells differentiated from embryonic stem cells or cells derived from induced pluripotent stem cells, so long as they are able to home to, reside and engraft in the bone marrow cavity. For example, endothelial stem cells that express CXCR4 can be substituted for hematopoietic stem cells in the methods disclosed herein.

These cells can also be mixture of hematopoeitic stem cells and mesenchymal stem cells (MSC) that express heterologous PDGFB. The presence of hematopoeitic stem cells helps MSCs to home to, stay at, and expand in the marrow stem cell niche (Méndez, et al., Nature 466:829-834, 2010). MSC can be isolated from bone marrow, such as from iliac crest, femora, tibiae, spine, rib or other medullary spaces. Other sources of mammalian MSC, include embryonic yolk sac, placenta, umbilical cord, periosteum, fetal and adolescent skin, fat, and blood.

As a non-limiting example, bone marrow derived MSC may be separated from hematopoietic cells by plating isolated cells on treated polystyrene tissue culture dishes. This allows MSC to attach, while the hematopoietic cells remain suspension, floating in the dish. The isolation media may be aspirated, such as about two to three days following plating, and replaced with fresh isolation media. The cells may be serially passaged two or more times to ensure complete removal of any contaminating cells such as hematopoietic cells. Prior to reaching confluence, cells may be sub-cultured by first washing cells with a sterile solution, such as phosphate-buffered saline (PBS), followed by the addition of a solution comprising trypsin, which may be an animal free product. In some embodiments, MSC can be maintained in culture for at least 10-20 passages. Other methods of isolating MSC, such as from adipose tissue or from any other tissue that contains MSC, are known in the art.

MSC can be isolated by fluorescence activated cell sorting (FACS). As a non-limiting example, bone marrow derived cells may be stained with an antibody specific for an MSC marker, and separated on the basis of expression of that marker. In some embodiments, MSC may be isolated from other cells by separating cells that express Sca1. Non-limiting examples of MSC markers that may be used to confirm isolation of human MSC by FACS, or other similar methods, include CD29, CD44, CD51, CD70, CD73, CD90/Thy-1, CD105, CD146, CD166, CD271, Nes, Stro1, SSEA-4, Integrin α1, PDGFRα, Sca1, SCFR/c-kit, and VCAM-1. Thus, cells can be isolated that express 1, 2, 3, 4, 5, 6, 7, 8, 9, 10, 11, 12, 13, 14, 15, 16, 17, 18, or all 18 of these markers.

Analysis of MSC markers can be performed using well-known methods (e.g., flow cytometric analysis, Western blot analysis, RT-PCR, in situ hybridization, immunofluorescence, immunohistochemistry, etc). Analysis of MSC proliferation may be performed using well-known methods, e.g., BrdU incorporation.

MSC can be propagated continuously in culture, using culture conditions that promote proliferation without promoting differentiation, using methods known in the art. The cells can be maintained in medium, such as, but not limited to, Dulbecco's Modified Eagle's Medium (DMEM); in the presence of fetal bovine serum or serum-free replacement without differentiation. Generally the cells may be passaged at about 75 to 95% confluence, using a protease, such as, but not limited to, trypsin or Accutase. In one embodiment, MSC are propagated continuously in mesenchymal stem cell proliferation media, such as DMEM, fetal calf serum (e.g., at a concentration of about 0-10%), and antibiotics such as penicillin/streptomycin (pen/strep; e.g., at a concentration of about 100 units/ml), and optionally horse serum (e.g., at a concentration of 0-10%). In embodiments where fetal calf serum and/or horse serum are undesirable, bFGF (e.g., at about 0-100 ng/ml) can be used.

In some embodiments, the MSC can be targeted and maintain at the endosteal bone surface by using a peptidomimetic ligand (LLP2A) linkage that against integrin on the surface of the MSC, coupled to a bisphosphonate that has high affinity for bone minerals on the bone surface. The bisphosphonate can be alendronate (Ale) or any bisphosphonate that has a strong affinity to bind bone minerals. (see, for example, Guan et al., Nature Medicine 18: 456-462, 2012).

In a specific, non-limiting example, LLP2A-Ale can be synthesized by Michael addition of the sulfhydryl group of LLP2A-Lys (D-Cys) to alendronate-maleimide (Ale-Mal), see Guan et al., supra. In some embodiments, the peptidomimetic section, LLP2A-Lys (d-Cys), can be synthesized to have a d-cysteine (d-Cys) attached to the side chain amino group of lysine (Lys), and to have a pair of identical hydrophilic linkers in series between the peptidomimetic ligand, LLP2A and the dipeptide Lys (d-Cys). This synthesis can be performed on ring amide 4-methyl-benzhydrylamine (MBHA) resin.

Ale-Mal can be prepared in situ from Ale and sulfosuccinimidyl-4-(N-maleimidomethyl)cyclohexane-1-carboxylate (sulfo-SMCC). In a specific non-limiting example, Ale disodium salt (1.0 eq.) (powder from lyophilization of aqueous solution of alendronic acid and 2 eq. NaOH) can be dissolved in, for example, 0.1 M PBS (with 10 mM EDTA), pH 7.5. The aqueous solution is then cooled in an ice water bath, and a solution of Sulfo-SMCC (1.1 eq.) in water is added drop-wise. After the completion of this addition, the resulting solution is allowed to warm to 20-25° C. while being stirred for 2 hours. This solution is cooled before the dropwise addition of a solution of LLP2A-Lys (d-Cys) (1.0 eq.) in a small amount of 50% acetonitrile/water. The pH is adjusted to between 6 and 7 with aqueous $NaHCO_3$. The resulting mixture is stirred for 1 hour and then allowed to warm to room temperature (20-22° C.). After a negative Ellman test, the solution is lyophilized. The resulting powder can then be redissolved in a small amount of 50% acetonitrile/water and purified by reverse phase high performance liquid chromatography (RP-HPLC) (C18 column). Buffer A can be 0.5% acetic acid/$H_2O$. Buffer B was 0.5% acetic acid/acetonitrile. The collected eluent can then be lyophilized. The structure of LLP2A is shown below:

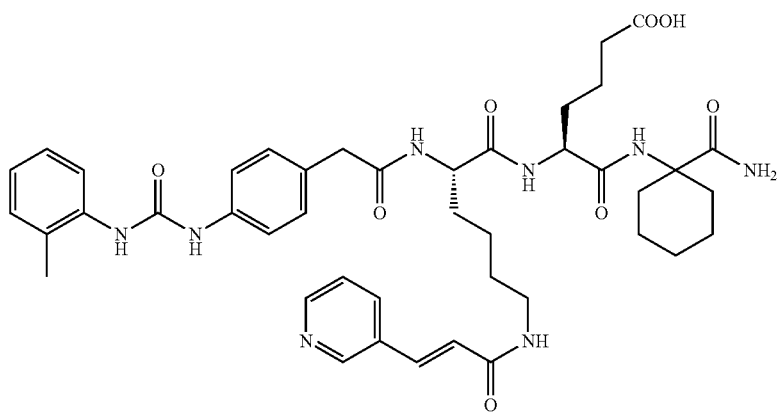

LLP2A (2)

This compound is disclosed in PCT Publication No. WO2013032527, which is incorporated herein by reference.

Bisphosphonates are widely used for the treatment of osteoporosis. This class of drugs is also used as a "vehicle" for delivering bone-targeted drugs to osseous tissue as prodrugs based on their bisphosphonic moiety. Bisphosphonates include the non-nitrogenous bisphosphonates (such as Etidronate (DIDRONEL®), Clodronate (BONEFOS®), and Tiludronate (SKELID®), and the nitrogenous bisphosphonates (such as Pamidronate (AREDIA®), Neridronate (NERIXIA®), Opadronate, Alendronate (FOSAMAX®), Ibandronate (BONIVA®), Risedronate (ACTONEL®), and Zoledronate (ZOMETA®).

The multipotent stem cells, such as hematopoietic stem cells, MSCs, or a combination of hematopoietic stem cells and MSCs, include a heterologous nucleic acid encoding PDGFB. In some embodiments, the multipotent stem cells are transformed with a construct, such as a vector, encoding PDGF. In a specific non-limiting example, the vector is a lentiviral vector. In one non-limiting embodiment the stem cells are transduced with a lentiviral vector including a nucleic acid encoding PDGFB that is operably linked to a PGK promoter and a wpre post-transcriptional regulatory element comprising the nucleic acid sequence set forth as SEQ ID NO: 26:

```
caggtggcacttttcggggaaatgtgcgcggaaccctatttgtttattt
ttctaaatacattcaaatatgtatccgctcatgagacaataaccctgata
aatgcttcaataatattgaaaaggaagagtatgagtattcaacatttcc
gtgtcgcccttattcccttttttgcggcattttgccttcctgttttttgct
cacccagaaacgctggtgaaagtaaaagatgctgaagatcagttgggtgc
acgagtgggttacatcgaactggatctcaacagcggtaagatccttgaga
gttttcgccccgaagaacgttttccaatgatgagcacttttaaagttctg
ctatgtggcgcggtattatcccgtattgacgccgggcaagagcaactcgg
tcgccgcatacactattctcagaatgacttggttgagtactcaccagtca
cagaaaagcatcttacggatggcatgacagtaagagaattatgcagtgct
gccataaccatgagtgataacactgcggccaacttacttctgacaacgat
cggaggaccgaaggagctaaccgcttttttgcacaacatggggatcatg
taactcgccttgatcgttgggaaccggagctgaatgaagccataccaaac
gacgagcgtgacaccacgatgcctgtagcaatggcaacaacgttgcgcaa
actattaactggcgaactacttactctagcttcccggcaacaattaatag
actggatggaggcggataaagttgcaggaccacttctgcgctcggccctt
ccggctggctggttttattgctgataaatctggagccggtgagcgtgggtc
tcgcggtatcattgcagcactggggccagatggtaagccctcccgtatcg
tagttatctacacgacggggagtcaggcaactatggatgaacgaaataga
cagatcgctgagataggtgcctcactgattaagcattggtaactgtcaga
ccaagtttactcatatatactttagattgatttaaaacttcatttttaat
ttaaaaggatctaggtgaagatcctttttgataatctcatgaccaaaatc
ccttaacgtgagttttcgttccactgagcgtcagaccccgtagaaaagat
caaaggatcttcttgagatcctttttttctgcgcgtaatctgctgcttgc
aaacaaaaaaaccaccgctaccagcggtggtttgtttgccggatcaagag
ctaccaactcttttccgaaggtaactggcttcagcagagcgcagatacc
aaatactgtccttctagtgtagccgtagttaggccaccacttcaagaact
ctgtagcaccgcctacatacctcgctctgctaatcctgttaccagtggct
gctgccagtggcgataagtcgtgtcttaccgggttggactcaagacgata
gttaccggataaggcgcagcggtcgggctgaacgggggttcgtgcacac
agcccagcttggagcgaacgacctacaccgaactgagatacctacagcgt
gagctatgagaaagcgccacgcttcccgaagggagaaaggcggacaggta
tccggtaagcggcagggtcggaacaggagagcgcacgagggagcttccag
gggaaacgcctggtatctttatagtcctgtcgggtttcgccacctctga
cttgagcgtcgatttttgtgatgctcgtcaggggggcggagcctatggaa
aaacgccagcaacgcggcctttttacggttcctggccttttgctggcctt
ttgctcacatgttctttcctgcgttatcccctgattctgtggataaccgt
attaccgcctttgagtgagctgataccgctcgccgcagccgaacgaccga
gcgcagcgagtcagtgagcgaggaagcggaagagcgcccaatacgcaaac
cgcctctccccgcgcgttggccgattcattaatgcagctggcacgacagg
tttcccgactggaaagcgggcagtgagcgcaacgcaattaatgtgagtta
gctcactcattaggcaccccaggctttacactttatgcttccggctcgta
tgttgtgtggaattgtgagcggataacaatttcacacaggaaacagctat
gaccatgattacgccaagcgcgcaattaaccctcactaaagggaacaaaa
gctggagctgcaagcttaatgtagtcttatgcaatactcttgtagtcttg
caacatggtaacgatgagttagcaacatgccttacaaggagagaaaaagc
accgtgcatgccgattggtggaagtaaggtggtacgatcgtgccttatta
ggaaggcaacagacgggtctgacatggattggacgaaccactgaattgcc
gcattgcagagatattgtatttaagtgcctagctcgatacaataaacggg
tctctctggttagaccagatctgagcctgggagctctctggctaactagg
gaacccactgcttaagcctcaataaagcttgccttgagtgcttcaagtag
tgtgtgcccgtctgttgtgtgactctggtaactagagatccctcagaccc
ttttagtcagtgtggaaaatctctagcagtggcgcccgaacagggacctg
aaagcgaaagggaaaccagagctctctcgacgcaggactcggcttgctga
agcgcgcacggcaagaggcgaggggcggcgactggtgagtacgccaaaaa
ttttgactagcggaggctagaaggagagagatgggtgcgagagcgtcagt
attaagcggggggagaattagatcgcgatgggaaaaaattcggttaaggcc
agggggaaagaaaaaatataaattaaaacatatagtatgggcaagcaggg
agctagaacgattcgcagttaatcctggcctgttagaaacatcagaaggc
tgtagacaaatactgggacagctacaaccatcccttcagacaggatcaga
agaacttagatcattatataatacagtagcaaccctctattgtgtgcatc
aaaggatagagataaaagacaccaaggaagctttagacaagatagaggaa
gagcaaaacaaaagtaagaccaccgcacagcaagcggccgctgatcttca
gacctggaggaggagatatgagggacaattggagaagtgaattatataaa
tataaagtagtaaaaattgaaccattaggagtagcacccaccaaggcaaa
```

-continued gagaagagtggtgcagagagaaaaaagagcagtgggaataggagctttgt
tccttgggttcttgggagcagcaggaagcactatgggcgcagcctcaatg
acgctgacggtacaggccagacaattattgtctggtatagtgcagcagca
gaacaatttgctgagggctattgaggcgcaacagcatctgttgcaactca
cagtctggggcatcaagcagctccaggcaagaatcctggctgtggaaaga
tacctaaaggatcaacagctcctgggatttgggggttgctctggaaaact
catttgcaccactgctgtgccttggaatgctagttggagtaataaatctc
tggaacagatttggaatcacacgacctggatggagtgggacagagaaatt
aacaattacacaagcttaatacactccttaattgaagaatcgcaaaacca
gcaagaaaagaatgaacaagaattattggaattagatAAatgggcaagtt
tgtggaattggtttaacataacaaattggctgtggtatataaaattattc
ataatgatagtaggaggcttggtaggtttaagaatagttttttgctgtact
ttctatagtgaatagagttaggcagggatattcaccattatcgtttcaga
cccacctcccaaccccgaggggacccgacaggcccgaaggaatagaagaa
gaaggtggagagagagacagagacagatccattcgattagtgaacggatc
tcgacggtatcggttaacttttaaaagaaaaggggggattgggggggtaca
gtgcaggggaagaatagtagacataatagcaacagacatacaaactaaa
gaattacaaaaacaaattacaaaaattcaaaattttatcgatcacgagac
tagcctcgagaagcttgatatcgaattcccacggggttggggttgcgcct
tttccaaggcagccctgggtttgcgcaggacgcggctgctctgggcgtg
gttccgggaaacgcagcggcgccgaccctgggtctcgcacattcttcacg
tccgttcgcagcgtcacccggatcttcgccgctaccttgtgggccccc
ggcgacgcttcctgctccgcccctaagtcgggaaggttccttgcggttcg
cggcgtgccggacgtgacaaacggaagccgcacgtctcactagtaccctc
gcagacggacagcgccaggagcaatggcagcgcgccgaccgcgatgggc
tgtggccaatagcggctgctcagcggggcgcgccgagagcagcggccggg
aaggggcggtgcgggaggcgggtgtgggcggtagtgtgggccctgttc
ctgcccgcgcggtgttccgcattctgcaagcctccggagcgcacgtcggc
agtcggctccctcgttgaccgaatcaccgacctctctcccccaggggatc
cgcgatcgccatgaatcgctgctgggcgctcttcctgtctctctgctgct
acctgcgtctggtcagcgccgaggggacccattcccgaggagctttat
gagatgctgagtgaccactcgatccgctcctttgatgatctccaacgcct
gctgcacggagaccccggagaggaagatggggccgagttggacctgaaca
tgacccgctcccactctggaggcgagctggagagcttggctcgtggaaga
aggagcctgggttccctgaccattgctgagccggccatgatcgccgagtg
caagacgcgcaccgaggtgttcgagatctcccggcgcctcatagaccgca
ccaacgccaacttcctggtgtggccgccctgtgtggaggtgcagcgctgc
tccggctgctgcaacaaccgcaacgtgcagtgccgcccacccaggtgca
gctgcgacctgtccaggtgagaaagatcgagattgtgcggaagaagccaa
tctttaagaaggccacggtgacgctggaagaccacctggcatgcaagtgt -continued gagacagtggcagctgcacggcctgtgacccgaagcccggggggttccca
ggagcagcgagccaaaacgccccaaactcgggtgaccattcggacggtgc
gagtccgccggccccccaagggcaagcaccggaaattcaagcacacgcat
gacaagacggcactgaaggagaccctggagcctaggtttaaacgtcgac
aatcaacctctggattacaaaatttgtgaaagattgactggtattcttaa
ctatgttgctccttttacgctatgtggatacgctgctttaatgcctttgt
atcatgctattgcttcccgtatggctttcattttctcctccttgtataaa
tcctggttgctgtctctttatgaggagttgtggcccgttgtcaggcaacg
tggcgtggtgtgcactgtgtttgctgacgcaaccccactggttggggca
ttgccaccacctgtcagctccttccgggactttcgctttccccctccct
attgccacggcggaactcatcgccgcctgccttgcccgctgctggacagg
ggctcggctgttgggcactgacaattccgtggtgttgtcggggaagctga
cgtcctttccatggctgctcgcctgtgttgccacctggattctgcgcggg
acgtccttctgctacgtcccttcggccctcaatccagcggaccttccttc
ccgcggcctgctgccggctctgcggcctcttccgcgtcttcgccttcgcc
ctcagacgagtcggatctccctttgggccgcctccccgcctggaattcga
gctcggtacctttaagaccaatgacttacaaggcagctgtagatcttagc
cacttttaaaagaaaaggggggactggaagggctaattcactcccaacg
aagacaagatctgcttttttgcttgtactgggtctctctggttagaccaga
tctgagcctgggagctctctggctaactagggaacccactgcttaagcct
caataaagcttgccttgagtgcttcaagtagtgtgtgcccgtctgttgtg
tgactctggtaactagagatccctcagaccctttagtcagtgtggaaaa
tctctagcagtagtagttcatgtcatcttattattcagtatttataactt
gcaaagaaatgaatatcagagagtgagaggaacttgtttattgcagctta
taatggttacaaataaagcaatagcatcacaaatttcacaaataaagcat
ttttttcactgcattctagttgtggtttgtccaaactcatcaatgtatct
tatcatgtctggctctagctatcccgcccctaactccgcccagttccgcc
cattctccgccccatggctgactaattttttttatttatgcagaggccga
ggccgcctcggcctctgagctattccagaagtagtgaggaggcttttttg
gaggcctaggcttttgcgtcgagacgtacccaattcgccctatagtgagt
cgtattacgcgcgctcactggccgtcgttttacaacgtcgtgactgggaa
aaccctggcgttacccaacttaatcgccttgcagcacatcccctttcgc
cagctggcgtaatagcgaagaggcccgcaccgatcgcccttcccaacagt
tgcgcagcctgaatggcgaatggcgcgacgcgccctgtagcggcgcatta
agcgcggcgggtgtggtggttacgcgcagcgtgaccgctacacttgccag
cgccctagcgcccgctcctttcgctttcttcccttcctttctcgccacgt
tcgccggctttccccgtcaagctctaaatcggggctccctttagggttc
cgatttagtgctttacggcacctcgaccccaaaaaacttgattagggtga
tggttcacgtagtgggccatcgccctgatagacggttttcgccctttga
cgttggagtccacgttctttaatagtggactcttgttccaaactggaaca
acactcaaccctatctcggtctattcttttgatttataagggattttgcc -continued

```
gatttcggcctattggttaaaaaatgagctgatttaacaaaaatttaacg cgaattttaacaaaatattaacgtttacaatttcc
```

A heterologous promoter can be included in the construct. Generally, the promoter is operably linked to a nucleic acid encoding a PDGFB polypeptide, such as a human PDGFB polypeptide. An exemplary nucleic acid sequence encoding human PDGFB is set forth in GENBANK Accession No. NM_002608.2, May 25, 2014, which is incorporated by reference herein.

(SEQ ID NO: 1)
```
cctgcctgcc tccctgcgca cccgcagcct ccccgctgc ctccctaggg ctcccctccg
gccgccagcg cccatttttc attccctaga tagagatact ttgcgcgcac acacatacat
acgcgcgcaa aaaggaaaaa aaaaaaaaaa agcccaccct ccagcctcgc tgcaaagaga
aaaccggagc agccgcagct cgcagctcgc agctcgcagc ccgcagcccg cagaggacgc
ccagagcggc gagcgggcgg gcagacggac cgacggactc gcgccgcgtc cacctgtcgg
ccgggcccag ccgagcgcgc agcgggcacg ccgcgcgcgc ggagcagccg tgcccgccgc
ccggcccccg cgccagggcg cacacgctcc cgcccccta cccggcccgg gcgggagttt
gcacctctcc ctgcccgggt gctcgagctg ccgttgcaaa gccaactttg gaaaagttt
tttggggag acttgggcct tgaggtgccc agctccgcgc tttccgattt tgggggcctt
tccagaaaat gttgcaaaaa agctaagccg gcgggcagag gaaaacgcct gtagccggcg
agtgaagacg aaccatcgac tgccgtgttc cttttcctct tggaggttgg agtcccctgg
gcgcccccac acggctagac gcctcggctg gttcgcgacg cagcccccg gccgtggatg
ctcactcggg ctcgggatcc gcccaggtag cggcctcgga cccaggtcct gcgcccaggt
cctcccctgc cccccagcga cggagccggg gccggggcg gcggcgcccg ggggccatgc
gggtgagccg cggctgcaga ggcctgagcg cctgatcgcc gcggacccga gccgagccca
ccccctccc cagccccca ccctggccgc ggggcggcg cgctcgatct acgcgtccgg
ggccccgcgg ggccgggccc ggagtcggca tgaatcgctg ctgggcgctc ttcctgtctc
tctgctgcta cctgcgtctg gtcagcgccg aggggaccc cattcccgag gagctttatg
agatgctgag tgaccactcg atccgctcct tgatgatct ccaacgcctg ctgcacggag
accccggaga ggaagatggg gccgagttgg acctgaacat gacccgctcc cactctggag
gcgagctgga gagcttggct cgtggaagaa ggagcctggg ttccctgacc attgctgagc
cggccatgat cgccgagtgc aagacgcgca ccgaggtgtt cgagatctcc cggcgcctca
tagaccgcac caacgccaac ttcctggtgt ggccgccctg tgtggaggtg cagcgctgct
ccggctgctg caacaaccgc aacgtgcagt gccgccccac ccaggtgcag ctgcgacctg
tccaggtgag aaagatcgag attgtgcgga agaagccaat ctttaagaag gccacggtga
cgctggaaga ccacctggca tgcaagtgtg agacagtggc agctgcacgg cctgtgaccc
gaagcccggg gggttcccag gagcagcgag ccaaaacgcc ccaaactcgg gtgaccattc
ggacggtgcg agtccgccgg ccccccaagg gcaagcaccg gaaattcaag cacacgcatg
acaagacggc actgaaggag acccttggag cctagggca tcggcaggag agtgtgtggg
cagggttatt taatatggta tttgctgtat tgcccccatg gggtccttgg agtgataata
ttgtttccct cgtccgtctg tctcgatgcc tgattcggac ggccaatggt gcttccccca
cccctccacg tgtccgtcca cccttccatc agcgggtctc ctcccagcgg cctccggcgt
cttgcccagc agctcaagaa gaaaagaag gactgaactc catcgccatc ttcttccctt
aactccaaga acttgggata agagtgtgag agagactgat ggggtcgctc tttgggggaa
acgggctcct tcccctgcac ctggcctggg ccacacctga gcgctgtgga ctgtcctgag
gagccctgag gacctctcag catagcctgc ctgatccctg aaccctggc cagctctgag
```

-continued

```
gggaggcacc tccaggcagg ccaggctgcc tcggactcca tggctaagac cacagacggg cacacagact ggagaaaacc cctcccacgg tgcccaaaca ccagtcacct cgtctccctg gtgcctctgt gcacagtggc ttctttcgt tttcgttttg aagacgtgga ctcctcttgg tgggtgtggc cagcacacca agtggctggg tgccctctca ggtgggttag agatggagtt tgctgttgag gtggctgtag atggtgacct gggtatcccc tgcctcctgc cacccttcc tccccacact ccactctgat tcacctcttc ctctggttcc tttcatctct ctacctccac cctgcatttt cctcttgtcc tggcccttca gtctgctcca ccaaggggct cttgaacccc ttattaaggc cccagatgat cccagtcact cctctctagg gcagaagact agaggccagg gcagcaaggg acctgctcat catattccaa cccagccacg actgccatgt aaggttgtgc agggtgtgta ctgcacaagg acattgtatg cagggagcac tgttcacatc atagataaag ctgatttgta tatttattat gacaatttct ggcagatgta ggtaaagagg aaaaggatcc ttttcctaat tcacacaaag actccttgtg gactggctgt gccctgatg cagcctgtgg cttggagtgg ccaaatagga gggagactgt ggtaggggca gggaggcaac actgctgtcc acatgacctc catttcccaa agtcctctgc tccagcaact gcccttccag gtgggtgtgg gacacctggg agaaggtctc caagggaggg tgcagccctc ttgcccgcac ccctccctgc ttgcacactt ccccatcttt gatccttctg agctccacct ctggtggctc ctcctaggaa accagctcgt gggctgggaa tggggagag aagggaaaag atccccaaga cccctgggg tgggatctga gctcccacct ccttcccac ctactgcact ttccccttc ccgccttcca aaacctgctt ccttcagttt gtaaagtcgg tgattatatt tttgggggct ttccttttat tttttaaatg taaaatttat ttatattccg tatttaaagt tgtaaaaaaa aataaccaca aaacaaaacc aaatgaaaaa aaaaaaaaaa aaa
```

In some embodiments, the nucleic acid sequence encoding PDGFB is at least 95%, 96%, 97%, 98%, 99% identical to SEQ ID NO: 1 An exemplary human PDGFB protein is set forth as GENBANK Accession No. NP_002599, May 25, 2014, which is incorporated herein by reference. An exemplary human PDGFB is:

(SEQ ID NO: 2)
MNRCWALFLS LCCYLRLVSA EGDPIPEELY EMLSDHSIRS FDDLQRLLHG DPGEEDGAEL

DLNMTRSHSG GELESLARGR RSLGSLTIAE PAMIAECKTR TEVFEISRRL IDRTNANFLV

WPPCVEVQRC SGCCNNRNVQ CRPTQVQLRP VQVRKIEIVR KKPIFKKATV TLEDHLACKC

ETVAAARPVT RSPGGSQEQR AKTPQTRVTI RTVRVRRPPK GKHRKFKHTH DKTALKETLG

A

Thus, in some embodiments, the nucleic acid sequence encodes SEQ ID NO: 2. In addition embodiments, the nucleic acid encoding a polypeptide at least 95%, 96%, 97%, 98%, 99% or 100% identical to SEQ ID NO: 2.

Other mammalian PDGFB that can be used include, but are not limited to, mouse PDGFB (GENBANK Accession No, XM_006520591.1 (mRNA), XP_00652065301 (protein)), cow PDGFB (GENBANK Accession No. NM_001017953.2 (mRNA), NP_001017953.2 (protein)), monkey PDGFB (GENBANK Accession No. XM_001097395.2 (mRNA), XP_001097395 (protein)), dog PDGFB (GENBANK Accession No. NM_001003383.1 (mRNA), NP_001003383.1 (protein), rat PDGFB (GENBANK Accession No. L40991.1 (mRNA), AAA70048.1 (protein)).

A promoter can be operably linked to a nucleic acid encoding PDGFB. The promoter is selected such that transferred multipotent stem cells produce a moderate amount of PDGFB, sufficient to increase bone mass and strength or bone fracture healing in a subject. In some embodiments, the promoter provides expression of about 1 to about 10 ng per $10^6$ cells of PDGFB in 24 hours. In other embodiments, the promoter provides expression of about 2 to about 6 ng per $10^6$ cells of PDGFB in 24 hours. In specific non-limiting examples, the promoter provides about 1 ng of PDGFB per $10^6$ cells, about 2 ng of PDGFB per $10^6$ cells, about 3 ng of PDGFB per $10^6$ cells, about 4 ng of PDGFB per $10^6$ cells, about 5 ng of PDGFB per $10^6$ cells, about 6 ng of PDGFB per $10^6$ cells, about 7 ng of PDGFB per $10^6$ cells, about 8 ng of PDGFB per $10^6$ cells, about 9 ng of PDGFB per $10^6$ cells, or about 10 ng of PDGFB per $10^6$ cells. The conditions under which PDGFB expression controlled by a particular promoter is measured can be determined using Sca1+ hematopoietic stem or precursor cells are cultured at a cell density of ~1×10^6 cells per ml of IMDM medium supplemented with 10% fetal bovine serum, 100 ng/ml Stem Cell Factor/c-kit ligand (SCF), 100 ng/ml Thrombopoietin (Tpo), and 100 ng/ml Flt-3 ligand. After culturing for 24 hours, culture medium is collected and the PDGF-B concentration in the cultured medium is determined with a commercial ELISA that is specific for PDGF-BB. In yet other embodiments, the multipotent stem cells produce about 2 to about 6 ng per 10^6 cells of PDGF-BB in 24 hours.

In further embodiments, the serum level of PDGF of the subject is normal (e.g., 0.1 to 30 ng/ml, such as 0.1-15 ng/ml) following the administration of the cells. In additional embodiments, the serum level of calcium of the subject is normal (e.g., 9-11 mg/dL) following the administration of the cells. In another embodiments, the serum level of PTH of the subject is normal following the administration of the cells.

The promoter can be any promoter of interest, including constitutive and inducible promoters. The promoter can be, for example, Phosphoglycerate Kinase-1 (PGK), beta-globin, human cytomegalovirus (CMV), Murine Stem Cell Virus (MSV), Human elongation factor-1 alpha (EF1alpha), ubiquitous chromatin opening elements (UCOE), spleen focus-forming virus (SFFV).

PGK promoter:
(SEQ ID NO: 27)
ccacgggggttggggttgcgccttttccaaggcagccctgggtttgcgcag ggacgcggctgctctgggcgtggttccgggaaacgcagcggcgccgaccc tgggtctcgcacattcttcacgtccgttcgcagcgtcacccggatcttcg ccgctacccttgtgggccccccggcgacgcttcctgctccgcccctaagt cgggaaggttccttgcggttcgcggcgtgccggacgtgacaaacggaagc cgcacgtctcactagtaccctcgcagacggacagcgccagggagcaatgg cagcgcgccgaccgcgatgggctgtggccaatagcggctgctcagcgggg cgcgccgagagcagcggccgggaaggggcggtgcgggaggcggggtgtgg ggcggtagtgtgggccctgttcctgcccgcgcggtgttccgcattctgca agcctccggagcgcacgtcggcagtcggctccctcgttgaccgaatcacc gacctctctccccag CAG promoter:
(SEQ ID NO: 28)
gtcgacattgattattgactagttattaatagtaatcaattacggggtca ttagttcatagcccatatatggagttccgcgttacataacttacggtaaa tggcccgcctggctgaccgcccaacgacccccgcccattgacgtcaataa tgacgtatgttcccatagtaacgccaatagggactttccattgacgtcaa tgggtggactatttacggtaaactgcccacttggcagtacatcaagtgta tcatatgccaagtacgccccctattgacgtcaatgacggtaaatggcccg cctggcattatgcccagtacatgaccttatgggactttcctacttggcag tacatctacgtattagtcatcgctattaccatgggtcgaggtgagcccca cgttctgcttcactctccccatctcccccccctccccacccccaattttg tatttatttatttttaattattttgtgcagcgatggggcggggggggg ggggcgcgcgccaggcggggcggggcgggcgaggggcggggcgggcg aggcggagaggtgcggcggcagccaatcagagcggcgcgctccgaaagtt tcctttttatggcgaggcggcggcggcggcggccctataaaaagcgaagcg cgcggcgggcgggagtcgctgcgttgccttcgccccgtgccccgctccgc gccgcctcgcgccgcccgccccggctctgactgaccgcgttactcccaca ggtgagcgggcgggacggcccttctcctccgggctgtaattagcgcttgg tttaatgacggctcgtttcttttctgtggctgcgtgaaagccttaaaggg ctccgggagggcctttgtgcgggggggagcggctcgggggggtgcgtgcg tgtgtgtgtgcgtggggagcgccgcgtgcgggcccgcgctgcccggcggct gtgagcgctgcgggcgcggcgcggggctttgtgcgctccgcgtgtgcgcg aggggagcgcggccggggggcggtgcccgcggtgcgggggggctgcgagg ggaacaaaggctgcgtgcggggtgtgtgcgtggggggggtgagcagggggt gtgggcgcggcggtcgggctgtaaccccccccctgcaccccccctccccgag ttgctgagcacggcccggcttcgggtgcggggctccgtgcgggggcgtggc gcggggctcgccgtgcgggcgggggggtggcggcaggtgggggtgccggg cggggcggggccgcctcgggccggggaggggctcgggggagggggcgcggcg gccccgagcgccggcggctgtcgaggcgcggcgagccgcagccattgcc ttttatggtaatcgtgcgagagggcgcagggacttcctttgtcccaaatc tggcggagccgaaatctgggaggcgccgccgcacccccctctagcgggcgc gggcgaagcggtgcggcgccggcaggaaggaaatgggcggggagggccctt cgtgcgtcgccgcgccgccgtccccttctccatctccagcctcggggctg ccgcaggggggacggctgccttcgggggggacggggcaggggcggggttcgg cttctggcgtgtgaccggcggctctagagcctctgctaaccatgttcatg ccttcttcttttttcctacagctcctgggcaacgtgctggttattgtgctg tctcatcatttttggcaaagaatt EF1 promoter:
(SEQ ID NO: 29)
Ggctccggtgcccgtcagtgggcagagcgcacatcgcccacagtccccga gaagttggggggaggggtcggcaattgaaccggtgcctagagaaggtggc gcggggtaaactgggaaagtgatgtcgtgtactggctccgcctttttccc gagggtgggggagaaccgtatataagtgcagtagtcgccgtgaacgttct ttttcgcaacgggtttgccgccagaacacaggtaagtgccgtgtgtggtt cccgcgggcctggcctcttttacgggttatggcccttgcgtgccttgaatt acttccactggctgcagtacgtgattcttgatcccgagcttcgggttgga agtgggtgggagagttcgaggccttgcgcttaaggagccccttcgcctcg tgcttgagttgaggcctggcctgggcgctggggccgccgcgtgcgaatct ggtggcaccttcgcgcctgtctcgctgctttcgataagtctctagccatt taaaatttttgatgacctgctgcgacgctttttttctggcaagatagtct tgtaaatgcgggccaagatctgcacactggtatttcggttttttggggccg cgggcggcgacggggcccgtgcgtcccagcgcacatgttcggcgaggcgg ggcctgcgagcgcggccaccgagaatcggacgggggtagtctcaagctgg ccggcctgctctggtgcctggcctcgcgccgccgtgtatcgccccgccct -continued gggcggcaaggctggcccggtcggcaccagttgcgtgagcggaaagatgg ccgcttccggccctgctgcagggagctcaaaatggaggacgcggcgctc gggagagcgggcgggtgagtcacccacacaaaggaaaagggccttccgt cctcagccgtcgcttcatgtgactccacggagtaccgggcgccgtccagg cacctcgattagttctcgagcttttggagtacgtcgtctttaggttgggg ggaggggttttatgcgatggagtttccccacactgagtgggtggagactg aagttaggccagcttggcacttgatgtaattctccttggaatttgcccttt tttgagtttggatcttggttcattctcaagcctcagacagtggttcaaag ttttttttcttccatttcaggtgtcgtga SFFV promoter:

(SEQ ID NO: 30)

Gctagctgcagtaacgccatttttgcaaggcatggaaaaataccaaaccaa gaatagagaagttcagatcaagggcgggtacatgaaaatagctaacgttg ggccaaacaggatatctgcggtgagcagtttcggccccggcccggggcca agaacagatggtcaccgcagtttcggccccggcccgaggccaagaacaga tggtccccagatatggcccaaccctcagcagtttcttaagacccatcaga tgtttccaggctcccccaaggacctgaaatgaccctgcgccttatttgaa ttaaccaatcagcctgcttctcgcttctgttcgcgcgcttctgcttcccg agctctataaaagagctcacaacccctcactcggcgcgccagtcctccga cagactgagtcgcccgggtacc CD14 promoter:

(SEQ ID NO: 31)

Agctagcgtgccaacagatgaggttcacaatctcttccacaaaacatgca gttaaatatctgaggatattcagggacttggatttggtggcaggagatca acataaaccaagacaaggaagaagtcaaagaaatgaatcaagtagattct ctgggatataaggtaggggattgggggggttggatagtgcagagtatggt actggcctaaggcactgaggatcatccttttcccacacccaccagagaag gcttaggctcccgagtcaacagggcattcaccgcctggggcgcctgagtc atcaggacactgccaggagacacagaaccctagatgccctgcagaatcct tcctgttacggtcccccctccctgaaacatccttcattgcaatatttccag gaaaggaaggggctggctcggaggaagagaggtggggaggtgatcaggg ttcacagaggagggaactgaatgacatcccaggattacataaactgtcag aggcagccgaagagttcacaagtgtgaagcctggaagccggcgggtgccg ctgtgtaggaaagaagctaaagcacttccagagcctgtccggagctcaga ggttcggaagacttatcgaccgcgatcgcc CD45 promoter:

(SEQ ID NO: 32)

Gccaagaacatcttaagtcacagaaacattagttttttggaagcagggttt gctgtaactatagtagaaatgacattctgattccactcctagcttcacaa ggatatctgtgaaagatttggggcaaaactgttaagctgtctgaaagtgc ttttgcataagaaatggggtttttactgctaaaactgtcatattgctgagtt ttgaatgccctaatggtaaatgatactgggttgccaaaaataaccagatt agtagttttttcattcatttggccgtctcagtaagtcaaatattgatact ttctactaagtcatcttgccaacacccatttttgttatacttatgctgaat -continued ctgtttgtcatctcttaagtaagaaaattattgattattttgtggggatt taatttaaaaaaaatggtaatggatactgtaaaggagcattatttggatg gtttaaaaacatcttccttgatgggaaaatcttttaaaaggctttctaac ttggtgtaattacttgaattaaggaagtgcaatgccattctactgactta gaacaacttttttgacttcctgcaaagaggacccttacagtattttgga gaagttagtaaaaccgaatctgacatcatccctagcagttcatgcagct agcaagtggtttgttcttagggtaacagaggaggaaattgttcctcgtct gataagacaacagtggagagtatgcatttatttatttacttttacatttt tgattcgttttacagagaaaaacttctacagagataacaattatttgc ttttcagaaggacgc Sca1 promoter:

(SEQ ID NO: 33)

ggctgggtgtgttttttgtcttgcatgaagacttctctgcagagggcctgg cttctctagcacaagcctggcaacatctggtacctctaactctaagatta ctcaagtacactgtagccctctcccagaagagttaatgtgagtggtctgt cagtagaatgggcaggagtccaccactaagggaagctagctccccaacaa tggggctgggtggaaactggaggactcatgagaattcctagtttaagact tttagagaaacagtgcacggcactgtggttatatggcctttccctccaaa gagaaggtgatggcccgttgtcatcctggagtagggataatgttggccc aggagccctggcaataaatagagtcagaagagcaaaacagcaataggtct gtgataatgggcagaactctctatactcagaagggaggactgtcacctgg ggttccagccatgactcctcctgttctccgccaagcacaagtggtctca gaagatactagaatatagaggatacagaggatttactgaaagagggactc cgtgtactgcttttatgatggggtgagatttggtggtgactaagctgctc agaatttatgcatattcctgtaagtgacctcacccatcctctgggggaaa aaaagcctcataacctcattgggtggtgacattggcagggtttatcactt ggatctttccttgccgcttttctttgtttgcagaggcttgctgtctcct gctctttctttcacatacacttcttcatgcatgagccaataccgagcaca gcatgtgacagaattagagagacaacatttcttgcttgctctcttcctct taccactgtgctgggttatgcggtgttggaggcaaactgtttgcttatat gatatattatagggtaagaaggaagggggtttttagtggtgctcgggcaga ggccatggagtgtaagcagccttcctgcttaagtggggtgcgctcagct tcactgatgctgtggtccatttttgggactcagttgtcctgtgagcacagc tgttcatttgctgtggtatcatctcaggatgatttccagctcaggtctct acctctgtccagcacacacagccccatacatccccaaacacatcagacac tgcttggtaacttccatcccagttgccagttagttcttgcctcaggactc tcactttgtggatgcaagagcctactgggggcttgctcaccagagccagt ctttaagtatttgtaaattgttttcctgcttataggaaggaggggccattg gctctgagccactgcaaaccataccttctatttagacacagaaaaaagcc aggtagtggaggcagaagtatcagcggctgttgtgcaccccttttgatagc tgtgtgttggagccagcctgttctactgagcaagtcctaggacagccaaa -continued

```
gctacacagagaaactttgtctcaaaaaaaaaaaaaaagtcaaaaaaa acccaaaataaacaaacaaaaaacacgaagctaaacaaaacaaaaactag taaagggctgagcaacttgacttcttcccttgctttctaattggcaagca caagtcaactgtggcctctggccctcggccctctcagttctcctgcacca tggttcctccccaactgctataaatctggcttgatcaggtcacaaacaaa tcttgctacctcttaaccaataaacatgatggcctggaaaaggttaagta ctgaaacccctccctcttcaggatgccagctgggaggagctgaaggaaat taaagtacttcagtccacatctgacagaacttgccactgtgcctgcaacc ttgtctgagaggaagtaaggactggtgtgaggagggagctgctaggtgac aaagggaagagccctcaggatagggctggggttgggagtgtgggattagg aaggaagagctgggtgggtggtgggtgagagaagtaggcagacatgtatt cctcagggaaagctgtgtggagggttggagggagggaagatcggatgcct gagctctgtgagagcccagggatgtgattgggggtctattaattggctcc aacttccaaggttttatctgtgcagcccttctctg
```

Beta globin promoter:

(SEQ ID NO: 34)
```
gatctctatttatttagcaataatagagaaagcatttaagagaataaagc aatgaaataagaaatttgtaaatttccttctgataactagaaatagagg atccagtttcttttggttaacctaaattttatttcattttattgttttat tttatttatttttatttattttgtgtaatcgtagtttcagagtgttaga gctgaaaggaagaagtaggagaaacatgcaaagtaaaagtataacacttt ccttactaaaccgacatgggtttccaggtaggggcaggattcaggatgac tgacagggcccttagggaacactgagaccctacgctgacctcataaatgc ttgctacctttgctgttttaattacatctttaatagcaggaagcagaac tctgcacttcaaaagttttcctcacctgaggagttaatttagtacaagg ggaaaaagtacaggggggatgggagaaaggcgatcacgttgggaagctata gagaaagaagagtaaatttagtaaaggaggtttaaacaaacaaaatata aagagaaataggaacttgaatcaaggaaatgattttaaaacgcagtattc ttagtggactagaggaaaaaaataatctgagccaagtagaagaccttttc ccctcctaccctactttctaagtcacagaggcttttgttccccagac actcttgcagattagtccaggcagaaacagttagatgtcccagttaacc tcctatttgacaccactgattacccattgatagtcacactttgggttgt aagtgacttttatttatttgtattttgactgcattaagaggtctctag tttttatctcttgtttcccaaaacctaataagtaactaatgcacagagc acattgatttgtatttattctatttttagacataatttattagcatgcat gagcaaattaagaaaaacaacaacaaatgaatgcatatatatgtatatgt atgtgtgtatatatacacacatatatatatatatttttctttctttcttacc agaaggttttaatccaaataaggagaagatatgcttagaaccgaggtaga gttttcatccattctgtcctgtaagtattttgcatattctggagacgcag gaagagatccatctacatatcccaaagctgaattatggtagacaaaactc ttccacttttagtgcatcaacttcttatttgtgtaataagaaaattggga aaacgatcttcaatatgcttaccaagctgtgattccaaatattacgtaaa
```

-continued
```
tacacttgcaaaggaggatgttttttagtagcaatttgtactgatggtatg gggccaagagatatatcttagagggagggctgagggtttgaagtccaact cctaagccagtgccagaagagccaaggacaggtacggctgtcatcactta gacctcaccctgtggagccacaccctagggttggccaatctactcccagg agcagggagggcaggagccagggctgggcataaaagtcagggcagagcca tctattgcttacatttgcttctgacacaactgtgttcactagcaacctca aacagacac
```

Other promoters include osteoblast gene specific promoters, housekeeping gene promoters (GAPDH, Actin, Cyclophilin), or chimeric promoters with viral enhancers with gene promoters, osteoblast enhancers with housekeeping gene or viral promoters. In some embodiments, the promoter in a non-viral promoter, in other embodiments, the promoter is a viral promoter. Any promoter can be used that provides a moderate expression level of PDGFB when operably linked to a nucleic acid sequence encoding PDGFB and introduced into multipotent stem cells.

Polynucleotide sequences encoding PDGFB, can be inserted into an expression vector, such as a plasmid, virus or other vehicle known in the art that has been manipulated by insertion or incorporation of the PDGFB sequence. Polynucleotide sequences which encode PDGFB can be operatively linked to the promoter and optionally additional expression control sequences. In one embodiment, an expression control sequence operatively linked to a coding sequence is ligated such that expression of the coding sequence is achieved under conditions compatible with the expression control sequences. The expression vector typically contains an origin of replication, a promoter, and specific genes that allow phenotypic selection of the transformed cells. Optionally, the expression vector can encode other molecules, such as, but not limited to, bone morphogenic protein (BMP)-2, BMP-4, cyclooxygenase (Cox)-2, fibroblast growth factor (FGF)-2, LIM mineralization protein (LMP)-1, vascular endothelial growth factor (VEGF).

An expression vector can optionally include a suicide gene, such as HSV thymidine kinase (HSV-TK). In such embodiments, once the multipotent stem cells engraft and promote strong bone formation, the majority of genetically engineered cells can be killed off by administration of ganciclovir (GCV). HSV-TK converts GCV into a toxic product and allows selective elimination of TK+ cells. An exemplary working concentration of GCV is 10-100 mg/kg/day for 7-21 days. Alternatively, PDGFB expression can be regulated using a TET-On system. In this embodiment, administration of Doxycycline (Dox) can induce PDGFB secretion from transduced cells. Doxycycline is added, for example at concentrations of 1-1000 ng/ml. In another embodiment, PDGFB can be regulated using a tamoxifen-inducible promoter system. In this embodiment, administration of tamoxifen can induced PDGFB secretion from transduced cells. Tamoxifen is added, for example, at concentrations of 1-1,000 mg/ml. In further embodiments, PDGFB can be regulated using an ecdysone receptor-inducible promoter system. In this embodiment, administration of ecdysone can induce PDGFB secretion from transduced cells. In the suicide promoter model, the HSV-TK vector will be included in the PDGF expression vector as a bicistronic vector. When PDGFB expression is no longer needed, the antibiotic, GCV, will be given to the subject orally, which will then activate the TK activity to kill off the transduced cells, which in essence will stop the expression of the transgenic PDGFB.

In one example, the vector is a viral vector, such as a retroviral vector, an adenoviral vector, or an adeno-associated vector (AAV). Suitable vectors are known in the art, and include viral vectors such as retroviral, lentiviral, adenoviral vectors, and AAV. In specific, non-limiting examples, the vector is a lentiviral vector, gammaretroviral vector, self-inactivating retroviral vector, adenoviral vector, or adeno-associated vector (AAV).

Viral vectors include an attenuated or defective DNA or RNA viruses, including, but not limited to, herpes simplex virus (HSV), papillomavirus, Epstein Barr virus (EBV), adenovirus, adeno-associated virus (AAV), Moloney leukemia virus (MLV) and human immunodeficiency virus (HIV, which is a lentiviral vector) and the like. Defective viruses, that entirely or almost entirely lack viral genes, can be used.

Use of defective viral vectors allows for administration to specific cells without concern that the vector can infect other cells. Thus, a specific tissue or cell type can be specifically targeted. Examples of particular vectors include, but are not limited to, a defective herpes virus 1 (HSV1) vector (Kaplitt et al. *Mol. Cell. Neurosci.*, 2:320-330, 1991), defective herpes virus vector lacking a glycoprotein L gene (See Patent Publication RD 371005 A), or other defective herpes virus vectors (See PCT Publication No. WO 94/21807; and PCT Publication No. WO 92/05263); an attenuated adenovirus vector, such as the vector described by Stratford-Perricaudet et al. (*J. Clin. Invest.*, 90:626-630 1992; La Salle et al., *Science* 259:988-990, 1993); and a defective adeno-associated virus vector (Samulski et al., *J. Virol.*, 61:3096-3101, 1987; Samulski et al., *J. Virol.*, 63:3822-3828, 1989; Lebkowski et al., *Mol. Cell. Biol.*, 8:3988-3996, 1988).

Genes can also be introduced in a retroviral vector (e.g., as described in U.S. Pat. Nos. 5,399,346, 4,650,764, 4,980,289 and 5,124,263; all of which are herein incorporated by reference; Mann et al., *Cell* 33:153, 1983; Markowitz et al., *J. Virol.*, 62:1120, 1988; PCT Application No. PCT/US95/14575; European Patent Application No. EP 453242; European Patent Application No. EP178220; Bernstein et al. Genet. Eng., 7:235, 1985; McCormick, *BioTechnol.*, 3:689, 1985; PCT Publication No. WO 95/07358; and Kuo et al. *Blood* 82:845, 1993). Most retroviruses are integrating viruses that infect dividing cells. Examples of retroviral vectors in which a foreign gene can be inserted include, but are not limited to: Moloney murine leukemia virus (MoMLV), Harvey murine sarcoma virus (HaMuSV), murine mammary tumor virus (MuMTV), and Rous Sarcoma Virus (RSV). In one embodiment, when the subject is a human, a vector such as the gibbon ape leukemia virus (GALV) can be utilized. A pseudotyped retroviral vector can be utilized that includes a heterologous envelope gene.

In one embodiment, the retroviral vector is a derivative of a murine or avian retrovirus, or a human or primate lentivirus. The lentiviruses are integrating viruses that infect nondividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest.

A number of additional retroviral vectors can incorporate multiple genes. All of these vectors can transfer or incorporate a gene for a selectable marker so that transduced cells can be identified and generated. To make the vector target-specific, a nucleic acid encoding PDGFB (with or without TK) can be inserted into the viral vector along with another gene which can serve as viral envelope protein; the vector also can encode the ligand for a receptor on a specific target cell. The envelope protein can be modified by attaching, for example, a sugar, a glycolipid, or a protein. In one specific, non-limiting example, targeting is accomplished by using an antibody to target the retroviral vector.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the long terminal repeat (LTR). These plasmids are missing a nucleotide sequence which enables the packaging mechanism to recognize an RNA transcript for encapsidation. Helper cell lines which have deletions of the packaging signal include, but are not limited to $\psi$2, PA317, and PA12, for example. Alternatively, NIH 3T3 or other tissue culture cells can be directly transfected with plasmids encoding the retroviral structural genes gag, pol and env, by conventional calcium phosphate transfection. These cell lines produce empty virions, since no genome is packaged. If a retroviral vector is introduced into such cells in which the packaging signal is intact, but the structural genes are replaced by other genes of interest, the vector can be packaged and vector virion produced. These cells are then transfected with the vector plasmid containing the genes of interest. The resulting cells release the retroviral vector into the culture medium. Thus, for production of viral particles, the gag, pol and env genes are coexpressed in the packaging cell line.

In some embodiments vectors can be constructed from different types of retrovirus, such as, HIV, MoMuLV ("murine Moloney leukemia virus" MSV ("murine Moloney sarcoma virus"); RSV ("Rous sarcoma virus"). In some examples, in order to construct recombinant retroviruses containing a nucleic acid sequence, a plasmid is constructed that contains the LTRs, the encapsidation sequence and the construct of the present disclosure comprising a nuclear targeting signal and a coding sequence. This construct is used to transfect a packaging cell line, which is able to supply the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that can include a part of the gag gene (Bender et al., *J. Virol.*, 61:1639, 1987). Recombinant retroviral vectors are purified by standard techniques.

Suitable vectors also include non-viral vectors. Exemplary non-viral vectors contain the sleeping beauty Tc1-like transposon and a DNA targeting sequence (DTS) facilitating nuclear entry. The cellular uptake (transfection) of non-viral vectors by mammalian cells can be improved on by using electroporation, insertion of a plasmid encased in liposomes, or microinjection. The use of DTS will promote nuclear uptake of the plasmid vector. An exemplary DTS is set forth below:

```
                                              (SEQ ID NO: 3)
    atgctttgca tacttctgcc tgctggggag cctggggact ttccacaccc taactgacac acattccaca gctggttggt acctgca
```

One non-viral vector with the single plasmid "Sleeping Beauty" transposon-based vector is described in Harris et al. (*Anal. Biochem.* 310:15-26, 2002, incorporated herein by reference). The Sleeping Beauty transposon systems employed in the methods disclosed herein can at least include a Sleeping Beauty transposon and a source of a Sleeping Beauty transposase activity. By Sleeping Beauty transposon is meant a nucleic acid that is flanked at either end by inverted repeats which are recognized by an enzyme having Sleeping Beauty transposase activity. By "recognized" is meant that a Sleeping Beauty transposase is capable of binding to the inverted repeat and then integrating the transposon flanked by the inverted repeat into the genome of the target cell. Representative inverted repeats that may be found in the Sleeping Beauty transposons of the subject methods include those disclosed in PCT Publication No. WO 98/40510 and PCT Publication No. WO 99/25817. Of particular interest are inverted repeats that are recognized by a transposase that shares at least about 80% amino acid identity to SEQ ID NO: 1 of PCT Publication No. WO 99/25817. For a complete description of the Sleeping Beauty Transposon system, see U.S. Pat. No. 6,613,752, which is incorporated herein by reference.

A second exemplary non-viral vector contains the sleeping beauty transposon a nuclear entry sequence (DTS) from the SV40 enhancer and other tissue specific DTSs (see Dean et al., *Gene Ther.* 12:881-890, 2005, incorporated herein by reference). Naturally occurring DNA sequences in the promoters of viruses or in the promoters of mammalian genes can be used to achieve nuclear entry of the DNA containing a transgene by incorporating these sequences into plasmid-expression vectors that can be expressed in a non-dividing cell. The techniques exploit the inherent nuclear entry properties of DNA sequences in gene promoters to transport DNA into the nucleus after the binding of endogenous cell-specific transcription factor proteins to specific DNA sequences.

For example, U.S. Pat. No. 5,827,705 discloses a plasmid DNA vector that incorporates a SV40 viral DNA sequence into a nucleic acid molecule to stimulate nuclear entry of the nucleic acid molecule into any mammalian cell nucleus (see also Dean, *Exp. Cell. Res.* 230:293 1997; Dean et al., *Gene Ther.* 12:881-890, 2005). In this system, the plasmid DNA containing the nuclear entry sequence (the SV40 DNA sequence) is introduced into the cytoplasm of the host cell, wherein proteins that coat bind the SV40 viral DNA in the plasmid and allow transport of the entire plasmid into the nucleus of the host cells. Nuclear entry can occur in non-dividing cells.

In one embodiment, the DNA is targeted into a specific site in the nuclei of the multipotent stem cells, wherein one or more transgenes (such as nucleic acids encoding PDGFB) of the vector are expressed. Methods are available for designing TALENs (Bogdanove and Voytas, Science. 2011 Sep. 30; 333(6051):1843-6. doi: 10.1126/science.1204094). TALEN-mediated gene targeting is effective in stem cells, including human embryonic stem cells (hESCs) and iPSCs (Hockenmeyer et al., Nat Biotechnol 29: 731-734, 2011). Genomic editing with TALENs capitalizes on the cell's ability to undergo homology directed repair (HDR), following an induced and targeted double-stranded DNA break (DSB). During this time a donor DNA template can be provided to the cell to insert new transgene or delete DNA sequences at the site of DSB (Cheng et al., Genes Cells. 17:431-8, 2012). TALENs can be designed that target any safe harbor locus, such as AAVS 1, CYBL, CCR5, and beta-globin. Zinc finger nucleases can also be used.

In additional embodiments, the methods allow for integration of a DNA, such as include a promoter operably linked to a nucleic acid encoding PDGFB, into an intron of the safe harbor locus. Thus, in some embodiments, a stem cell can be contacted with the upstream TALEN, the downstream TALEN, and the polynucleotide of interest encoding PDGFB, such that the nucleic acid of interest encoding PDGFB operably linked to a heterologous promoter is integrated into a safe-harbor locus in the multipotent stem cell.

In some embodiments, the methods include introducing into the multipotent stem cell an upstream transcription activator-like effector nuclease (TALEN) comprising an upstream DNA-binding domain linked to a DNA cleavage domain, wherein the upstream DNA binding domain specifically binds to the safe-harbor locus at a site upstream of a genomic insertion site in the genome of the multipotent stem cell, (b) a downstream transcription activator-like effector nuclease (TALEN) comprising a downstream DNA-binding domain linked to a DNA cleavage domain, wherein the downstream DNA binding domain specifically binds to the safe-harbor locus at a site downstream of the genomic insertion site in the genome of the neuronal stem cell, and (c) a single or double-stranded donor polynucleotide comprising sense and/or antisense strand polynucleotide overhangs that are complementary to corresponding polynucleotide overhangs of cleaved the genomic DNA when cleaved at the genomic insertion site. The complementary overhangs facilitate homologous recombination of the donor polynucleotide with the cleaved genomic DNA, to allow introduction of the polynucleotide into the genome of the cell. These methods provide introduction of the donor polynucleotide, including a promoter and a nucleic acid sequence encoding PDGFB, into the genomic insertion site into the safe harbor locus in the genome of the neuronal stem cell. In some embodiments, the upstream TALEN binds to the sense strand of a genomic DNA locus flanking the insertion site and the downstream TALEN binds to the antisense strand of a genomic DNA locus flanking the insertion site.

In additional embodiments, methods are provided for inserting a polynucleotide into the genome of a multipotent stem cell that include introducing into the multipotent stem cell a first TALEN with a DNA-binding domain specific for a DNA sequence within the CLYBL, CCR5 or AAVS 1 safe-harbor locus that binds to the sense strand of DNA upstream of a genomic sequence of interest and a second TALEN with a DNA-binding domain specific for a DNA sequence within the CLYBL, CCR5 or AAVS 1 safe-harbor locus that binds to the antisense strand of DNA downstream from the genomic sequence of interest, and a single or double-stranded donor polynucleotide with sense and/or antisense strand polynucleotide overhangs that are complementary to corresponding polynucleotide overhangs of genomic DNA cleaved by the introduced TALENs at a genomic insertion site. The complementary overhangs facilitate homologous recombination of the donor polynucleotide with the cleaved genomic DNA, providing for the introduction of the donor polynucleotide encoding PDGFB into the genome of the multipotent stem cell.

In another embodiment, the DNA is targeted into a specific site in the nuclei of the multipotent stem cells, wherein one or more transgenes (such as nucleic acids encoding PDGFB) of the vector are expressed. Methods to insert DNA to a specific site in the nuclei of the multipotent stem cells involve the clustered, regularly interspaced, short palindromic repeat (CRISPR) technology (Sander & Joung. *Nature Biotechnol* 32:347-355, 2014, doi: 10.1038/nbt.2842, which is incorporated by reference herein in its entirety); this approach generates RNA-guided nucleases, such as Cas9, with customizable specificities. CRISPRs are DNA loci containing short repetitions of base sequences. Each repetition is followed by short segments of "spacer DNA" from previous exposures to a virus (Marraffini & Sontheimer. *Nature Rev Genetics* 11:181-190, 2010, doi: 10.1038/nrg2749, which is incorporated by reference herein in its entirety). CRISPRs are often associated with Cas genes that code for proteins related to CRISPRs. The CRISPR/Cas system is a prokaryotic immune system that confers resistance and acquired immunity against invading foreign genetic elements such as plasmids and via RNA-guided DNA cleavage (Wiedenheft et al., *Nature* 482:331-338, 2012, which is incorporated by reference herein in its entirety). In the type II CRISPR/Cas system, short segments of foreign DNA, termed 'spacers' are integrated within the CRISPR genomic loci and transcribed and processed into short CRISPR RNA (crRNA). These crRNAs anneal to transactivating crRNAs (tracrRNAs) and direct sequence-specific cleavage and silencing of pathogenic DNA by Cas proteins. Target recognition by the Cas9 protein requires a 'seed' sequence within the crRNA and a conserved dinucleotide-containing protospacer adjacent motif (PAM) sequence upstream of the crRNA binding region (Jinek et al. *Science* 337:816-821, 2012, which is incorporated by reference herein in its entirety). The CRISPR/Cas system can thereby be retargeted to cleave virtually any DNA sequence by redesigning the crRNA. Significantly, the CRISPR/Cas system has been shown to be directly portable to human cells by co-delivery of plasmids expressing the Cas9 endonuclease and the necessary crRNA components (Cho et al., *Nature Biotechnol* 31:230-232, 2013; Cong et al., *Science* 339:819-823, 2013; Mali et al., *Science* 339:823-826, 2013, each of which is incorporated by reference herein in its entirety). These programmable RNA-guided DNA endonucleases have demonstrated multiplexed gene disruption capabilities (Cong et al., *Science* 339:819-823, 2013, which is incorporated by reference herein in its entirety) and targeted integration in iPS cells (Mali et al., *Science* 339:823-826, 2013, which is incorporated by reference herein in its entirety). Cas9 endonucleases have also been converted into nickases (Cong et al., *Science* 339:819-823, 2013, which is incorporated by reference herein in its entirety), enabling an additional level of control over the mechanism of DNA repair. The CRISPR/Cas system can be used for gene editing (adding, disrupting or changing the sequence of specific genes) and gene regulation in species throughout the tree of life (Mali et al., *Nature Methods* 10:957-963, 2013; doi: 10.1038/nmeth.2649, which is incorporated by reference herein in its entirety). By delivering the Cas9 protein and appropriate guide RNAs into a cell, the organism's genome can be cut at any desired location. It may be possible to use CRISPR to build RNA-guided gene drives capable of altering the genomes of entire populations (Esvelt et al., eLife doi:10.7554/eLife.03401, which is incorporated by reference herein in its entirety).

In additional embodiments, the methods allow for integration of a DNA, such as include a promoter operably linked to a nucleic acid encoding PDGFB, into an intron of the safe harbor locus. Thus, in some embodiments, a stem cell can be transformed with the third generation CRISPR/Cas9-sgRNA technology that is suitable for genome edition. To target PDGFB to genome safe harbors, such as AAVS 1 site, one can deliver three plasmids to Sca1$^+$ cells by nucleofection. One plasmid expresses Cas9 protein; one plasmid encodes an sgRNA that targets the AAVS 1 site. The third plasmid is a DNA donor, which is the PGK (or other) promoter and PDGFB coding sequence flanked by homologous arms of AAVS 1. Drug resistance genes such as puro can be incorporated in the plasmid. After plasmid transfection and selection, ~10% cells will be targeted with PDGFB. Methods for introducing DNA into multipotent stem cells also include chemical and physical methods. Chemical methods include liposome-based gene transfer or lipofection, calcium phosphate-mediated gene transfer, DEAE-dextran transfection techniques, and polyethyleneimine (PEI)-mediated delivery. Physical methods include ballistic gene transfer (introduces particles coated with DNA into cells), microinjection, and nucleofection (Amaxa biosystem, 2004).

Electroporation can be used to introduce non-viral vectors into cells and tissues in vivo. Generally, in this method, a high concentration of vector DNA is added to a suspension of host cell and the mixture is subjected to an electrical field of approximately 200 to 600 V/cm. Following electroporation, transformed cells are identified by growth on appropriate medium containing a selective agent. Electroporation has also been effectively used in animals or humans (see Lohr et al., *Cancer Res.* 61:3281-3284, 2001; Nakano et al, *Hum Gene Ther.* 12:1289-1297, 2001; Kim et al., *Gene Ther.* 10:1216-1224, 2003; Dean et al. *Gene Ther.* 10:1608-1615, 2003; and Young et al., *Gene Ther.* 10:1465-1470, 2003).

Another targeted delivery system for a polynucleotide encoding PDGFB is a colloidal dispersion system. Colloidal dispersion systems include macromolecule complexes, nanocapsules, microspheres, beads, and lipid-based systems including oil-in-water emulsions, micelles, mixed micelles, and liposomes. One colloidal dispersion system is a liposome. Liposomes are artificial membrane vesicles which are useful as delivery vehicles in vitro and in vivo. It has been shown that large unilamellar vesicles (LUV), which range in size from 0.2-4.0 microns, can encapsulate a substantial percentage of an aqueous buffer containing large macromolecules. RNA, DNA and intact virions can be encapsulated within the aqueous interior and be delivered to cells in a biologically active form (Fraley et al., Trends Biochem. Sci. 6:77, 1981). In order for a liposome to be an efficient gene transfer vehicle, the following characteristics should be present: (1) encapsulation of the nucleic acid of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14-18 carbon atoms, particularly from 16-18 carbon atoms, and is saturated. Illustrative phospholipids include, for example, phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Another targeting delivery system is the use of biodegradable and biocompatible polymer scaffolds (see Jang et al., Expert Rev. Medical Devices 1:127-138, 2004). These scaffolds usually contain a mixtures of one or more biodegradable polymers, for example and without limitation, saturated aliphatic polyesters, such as poly(lactic acid) (PLA), poly(glycolic acid), or poly(lactic-co-glycolide) (PLGA) copolymers, unsaturated linear polyesters, such as polypropylene fumarate (PPF), or microorganism produced aliphatic polyesters, such as polyhydroxyalkanoates (PHA), (see Rezwan et al., Biomaterials 27:3413-3431, 2006; Laurencin et al., Clin. Orthopaed. Rel. Res. 447:221-236). By varying the proportion of the various components, polymeric scaffolds of different mechanical properties are obtained. A commonly used scaffold contains a ratio of PLA to PGA is 75:25, but this ratio may change depending upon the specific application. Other commonly used scaffolds include surface bioeroding polymers, such as poly(anhydrides), such as trimellitylimidoglycine (TMA-gly) or pyromellitylimidoalanine (PMA-ala), or poly(phosphazenes), such as high molecular weight poly(organophosphazenes) (P[PHOS]), and bioactive ceramics. The gradual biodegradation of these scaffolds allows the gradual release of drugs or gene from the scaffold. Thus, an advantage of these polymeric carriers is that they represent not only a scaffold but also a drug or gene delivery system. This system is applicable to the delivery of plasmid DNA and also applicable to viral vectors, such as AAV or retroviral vectors, as well as transposon-based vectors.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Methods of Treatment

The compositions and methods described herein can be used to produce PDGFB in multipotent stem cells that are capable of homing to and engrafting the bone marrow. These cells can be hematopoietic stem cells and/or MSC. These methods are of use for therapeutic or prophylactic treatment of a condition or disease affecting bone, for example bone growth (e.g., bone formation), bone maintenance and/or bone repair. These multipotent stem cells that produce PDGFB can be used for the treatment of a condition or disease characterized by impaired bone formation, such as due to aging, hormonal status, or bone loss due to genetic or physiological disorders, e.g., osteoporosis, and osteogenesis imperfecta. The multipotent stem cells that produce PDGFB can also be used to enhance bone healing, especially the healing of bone fractures. The multipotent stem cells that produce PDGFB can be used to treat subjects undergoing bone marrow transplantation which includes total body irradiation preconditioning, and are at a high risk for osteoporosis. In some embodiments, the multipotent stem cells that produced PDGFB increase bone formation and/or increase bone mass and strength and/or reduce osteomalacia. In additional embodiments, the multipotent stem cells increase trabecular connections and/or decrease cortical porosity.

In some embodiments, a mixture of hematopoietic stem cells and MSCs is administered to the subject. Addition of mesenchymal cells to the hematopoietic cells can act as partners to promote their engraftment into the vascular niches in the marrow cavity.

In some embodiments, the multipotent stem cells produce a moderate amount of PDGFB, specifically about 1 to about 10 ng per $10^6$ cells of PDGFB in 24 hours. In other embodiments, the multipotent stem cells produce about 2 to about 6 ng per $10^6$ cells of PDGFB in 24 hours. In specific non-limiting examples, the multipotent stem cells produce about 1 ng of PDGFB per $10^6$ cells, about 2 ng of PDGFB per $10^6$ cell, about 3 ng of PDGFB per $10^6$ cells, about 4 ng of PDGFB per $10^6$ cells, about 5 ng of PDGFB per $10^6$ cells, about 6 ng of PDGFB per $10^6$ cells, about 7 ng of PDGFB per $10^6$ cells, about 8 ng of PDGFB per $10^6$ cells, about 9 ng of PDGFB per $10^6$ cells, or about 10 ng of PDGFB per $10^6$ cells. In further embodiments, the serum level of PDGF of the subject is normal following the administration of the cells, and the serum levels of calcium and PTH of the subject is normal following the administration of the cells.

When the nucleic acids encoding PDGFB are introduced into cells that are capable of homing to and engrafting the bone marrow, the PDGFB is expressed in skeletal tissue. Without being bound by theory, the use of multipotent stem cells reduces safety concerns and increasing efficacy of delivery.

Methods are provided to promote fracture healing that utilize the stem cells described herein. The fracture can be in any bone, including but not limited to cranial bones such as the frontal bone, parietal bone, temporal bone, occipital bone, sphenoid bone, ethmoid bone; facial bones such as the zygomatic bone, superior and inferior maxilla, nasal bone, mandible, palantine bone, lacrimal bone, vomer bone, the inferior nasal conchae; the bones of the ear, such as the malleus, incus, stapes; the hyoid bone; the bones of the shoulder, such as the clavicle or scapula; the bones of the thorax, such as the sternum or the ribs; the bones of the spinal column including the cervical vertebrae, lumbar vertebrae, and thoracic vertebrae; the bones of the arm, including the humerus, ulna and radius; the bones of the hands, including the scaphoid, lunate, triquetrum bone, psiform bone, trapezium bone, trapezoid bone, cpitate bone, and hamate bone; the bones of the palm such as the metacarpal bones; the bones of the fingers such as the proximal, intermediate and distal phalanges the bones of the pelvis such as the ilium, sacrum and coccyx; the bones of the legs, such as the femur, tibia, patella, and fibulal; the bones of the feet, such as the calcaneus, talus, navicular bone, medial cuneiform bone, intermediate cuniform bone, lateral cuneiform bone, cuboidal bone, metatarsal bone, proximal phalanges, intermediate phalanges and the distal phalanges; and the pelvic bones. In one example, a bone fracture is repaired in the absence of extra-skeletal bone formation, such as in the absence of bone formation in the soft tissues.

Methods are also provided to promote spinal fusion using the stem cells described herein. Spinal fusion can be induced in any of the vertebrae, including, but not limited to, the cervical vertebrae, lumbar vertebrae, and thoracic vertebrae. In one example, spinal fusion occurs in the absence of extra-skeletal bone formation, such as in the absence of bone formation in the soft tissues.

In additional embodiments, the stem cells disclosed herein can be used to treat subjects that have a broken bone due to any disease, defect, or disorder which affects bone strength, function, and/or integrity, such as decreasing bone tensile strength and modulus. Examples of bone diseases include, but are not limited to, diseases of bone fragility, such as all types of osteoporosis according to etiology and pathogenesis. Other examples include subjects affected with malignancies and/or cancers of the bone such as a sarcoma, such as osteosarcoma. The methods can be used in human or non-human subjects (see for example, Akhter et al., *Calcif. Tissue Int.* 78: 357-362, 2006). The method can also be used to treat subjects that have had full body (or partial body) radiation therapy, and have fragility as a result of this therapy.

Other clinical conditions that can be treated by this approach include, but are not limited to, osteoporosis, transplantation-induced osteoporosis and bone loss, osteogenesis imperfecta, avascular necrosis, all types of metabolic bone diseases according to pathogenesis and etiology, avascular osteonecrosis, and genetic diseases which result in abnormal bone formation such as McCune-Albright syndrome (MAS).

In some embodiments, a therapeutically effective amount of stem cells expressing PDGF is administered to a subject to increase bone fracture healing in the subject. The fracture does not need to be completely healed for the method to be effective. For example, administration of a therapeutically effective amount of a disclosed agent or composition can increase bone fracture healing by a desired amount, for example by at least 10%, at least 20%, at least 50%, at least 60%, at least 70%, at least 80%, at least 90%, at least 95%, at least 98%, or at least 100% or more, as compared to the bone fracture healing in the absence of the composition.

In other embodiments, a therapeutically effective amount of stem cells expressing PDGFB is administered to a subject to increase bone strength in the subject. It is understood that the increase in bone strength does not need to occur in every bone of the subject, but can be limited to (or targeted to) particular bones or portions of particular bones (for example, the pelvis or femur or a portion thereof) in the subject. For example, administration of a therapeutically effective amount of a disclosed agent or composition can increase bone strength by a desired amount, for example by at least 10%, at least 20%, at least 50%, at least 60%, at least 70%, at least 80%, at least 90%, at least 95%, at least 98%, or at least 100% or more, as compared to the bone strength in the absence of the composition.

In some examples, an increase in bone strength can be measured as an increase in bone mineral density in a subject. The increase in bone mineral density does not need to occur in every bone of the subject, but can be limited to (or targeted to) particular bones or portions of particular bones (for example, the pelvis or femur or a portion thereof) in the subject. For example, administration of a therapeutically effective amount of a disclosed agent or composition can increase bone mineral density by a desired amount, for example by at least 10%, at least 20%, at least 50%, at least 60%, at least 70%, at least 80%, at least 90%, at least 95%, at least 98%, or at least 100% or more, as compared to the bone mineral density in the absence of the agent or composition. Methods of measuring bone mineral density in a subject are known and described herein.

Because bone growth (and, e.g., repair of bone fractures) is enhanced by mechanical loading of the bone, the methods described above can be combined with regimens involving or simulating physical loading of the bone. Such therapies increase bone growth at the desired locations within the skeletal system, and can be accomplished even in subjects that are immobilized or otherwise unable to undergo substantial physical activity. In addition to exercise, and/or physical therapy, treatment modalities employing vibration, e.g., ultrasound vibration, have been found to simulate mechanical loading and enhance bone growth. Additionally, because the methods described herein result in rapid and substantial bone growth, these therapies are most advantageously combined with administration of calcium and vitamin D at levels sufficient to prevent calcium deficiency that may otherwise occur with intense bone formation. For example, calcium intake can be coordinated with the degree or intensity of the formation to avoid calcium deficiency. In addition, to optimize the effects of the osteogenic growth factor expressed by the hematopoietic stem cell and its progeny, in some cases additional growth factors (including for example, osteogenic growth factors and cytokines). Accordingly, the compositions and methods for disclosed herein are suitable for treating subjects with bone wasting and/or bone fragility disorders, regardless of age, gender, or mobility status. Thus, the disclosed multipotent stem cells are of use for treating osteoporosis.

In some embodiments, the subject can be preconditioned prior to administration of the multipotent stem cells to destroy all or a portion of the native bone marrow and blood cells in the subject. Methods of preconditioning prior to administration of multipotent stems cells are known in the art, and include, for example, total or partial body irradiation, or chemically induced myeloablation.

In some embodiments, local preconditioning of a small area or region of bone marrow in the subject (such as at the hip femoral neck) can be performed prior to administration of the multipotent stem cells to destroy all or a portion of the native bone marrow and blood cells in a selected area of the body. After the local preconditioning, the multipotent stem cells can be administered systemically (e.g., by iv administration) or locally (e.g., by direct injection to the preconditioned site) to specifically increase bone formation at that site. This embodiment reduces damage in terms of cellular injury to non-preconditioned areas of the body, and allows for increased bone mass and strength at the locally treated site (e.g., the femoral neck).

In other embodiments, the subject is not preconditioned (or only a low amount of preconditioning is used) prior to administration of the multipotent stem cells. In some such embodiments, the subject is administered a therapeutically effective amount of multipotent stem cells, wherein each multipotent stem cell is transformed with a recombinant nucleic acid molecule comprising a strong heterologous promoter (e.g., a SFFV promoter) operably linked to a nucleic acid encoding PDGFB.

In several embodiments, a multipotent stem cell expressing a nucleic acid encoding PDGFB can be administered in a conjunction with an additional therapeutic agent, such as a growth factor. Non-limiting examples of suitable growth factors include osteogenin, Insulin-like Growth Factor (IGF)-1, IGF-II, TGF-β1, TGF-β2, TGF-β3, TGF-β4, TGF-β5, osteoinductive factor (OIF), basic Fibroblast Growth Factor (bFGF), acidic Fibroblast Growth Factor (aFGF), vascular endothelial growth factor (VEGF), Growth Hormone (GH), growth and differentiation factors (GDF)-5 through 9, osteogenic protein-1 (OP-1) and any one of the many known bone morphogenic proteins (BMPs), including but not limited to BMP-1, BMP-2, BMP-2A, BMP-2B, BMP-3, BMP-3b, BMP-4, BMP-5, BMP-6, BMP-7, BMP-8, BMP-8b, BMP-9, BMP-10, BMP-11, BMP-12, BMP-13, BMP-14, BMP-15. One or more agents that support the formation, development and growth of new bone, and/or remodeling of bone can be administered. Typical examples of compounds that function in such a supportive manner include, though are not limited to, extracellular matrix-associated bone proteins (e.g., alkaline phosphatase, osteocalcin, bone sialoprotein (BSP) and osteocalcin in secreted phosphoprotein (SPP)-1, type I collagen, fibronectin, osteonectin, thrombospondin, matrix-gla-protein, alkaline phosphatase and osteopontin).

In specific embodiments, for the treatment of a fracture, a multipotent stem cell expressing a nucleic acid encoding PDGFB can be administered in conjunction with Cox-2, LMP-1, FGF-2, a BMP or related proteins, or a nucleic acid encoding one or more of these proteins. In other embodiments, a multipotent stem cell expressing a nucleic acid encoding PDGFB can be administered in conjunction with a bone morphogenic protein, such as BMP-2, BMP-4, BMP-7, and/or BMP-2/4 hybrid, or a nucleic acid encoding a bone morphogenic protein. In another embodiment, a multipotent stem cell expressing a nucleic acid encoding PDGFB can be administered in conjunction with a growth factor, such as FGF-2 to further enhance fracture repair. The multipotent stem cell expressing a nucleic acid encoding PDGFB can also be submitted with a factor that promotes angiogenesis.

Other agents can also be administered, such as chemical compounds. In one embodiment, a multipotent stem cell expressing a nucleic acid encoding PDGFB is administered with an anti-inflammatory agent, such as a non-steroidal anti-inflammatory agent. In another embodiment, a multipotent stem cell expressing a nucleic acid encoding PDGFB is administered with an antibiotic, antifungal, or anti-viral agent. Thus, a multipotent stem cell expressing a nucleic acid encoding PDGFB can be used alone or with other therapeutic agents, to promote fracture healing and/or spinal fusion, or for the treatment of a bone disorder. This therapy may be used along with genes (such as Hox4) or small molecules (such as SR17), to increase competitiveness of the genetically modified hematopoietic stem cells against endogenous hematopoietic stem cells for homing and engraftment in the niches within the bone marrow.

EXAMPLES

The following examples are provided to illustrate particular features of certain embodiments, but the scope of the claims should not be limited to those features exemplified.

Cell therapy is now considered the third pillar of medicine: "Cells uniquely sense their surroundings, make decisions and exhibit varied and regulable behaviors," such as targeting (Fishbach et al., *Science translational medicine.* 2013; 5(179):179ps7 *Science translational medicine.* 2013; 5(179):179ps7). Prior work on the skeleton established proof of principle in the mouse using engineered stem cell therapy, which could be given intravenously and would result in a rejuvenation of the skeleton (Hall et al. *Molecular therapy the journal of the American Society of Gene Therapy.* 2007; 15(10):1881-9). Engraftment occurred at sites where bone is lost in osteoporosis models (i.e. the HSC niches) and substantial augmentation of bone matrix at these sites in response to a single intravenous injection of stem cells engineered to overexpress a bone growth factor (Hall et al., *op. cit*). Despite these advances, several serious problems were encountered. Instead of being stronger, the prior methods produced bones that were weak and sometimes fractured during processing. This was associated with severe hypocalcaemia, secondary hyperparathyroidism and osteomalacia. This constellation of findings suggested that the stimulus for bone formation was so strong that it overwhelmed the adaptive capacity of the gut to provide sufficient calcium for mineralization.

The present study sought to resolve these adverse side effects. In the previous work, a modified FGF2 gene was expressed in our stem cells. In the current study, the PDGFB gene was used. In addition, promoters of different strengths were utilized to variously express PDGFB in order to vary the dose of the gene product in the hematopoietic niches from high to low.

As disclosed below, the promoter with high activity duplicated the severe osteomalacia seen with the FGF2 gene construct. In sharp contrast, utilizing a moderate strength promoter, the osteomalacia was completely resolved and an increase in bone strength (load to failure) of 45% was shown. No traditional monotherapy for osteoporosis has long-term positive effect on maximum load (Amugongo et al., *Bone.* 67:257-268, 2014). Moreover a 20-fold increase in trabecular connectivity was uniquely produced that was relevant to bone mechanical performance.

Example 1

Experimental Strategies

In the present studies, methods were used that included isolating hematopoietic stem cells (HSCs), engineering these cells to overexpress a growth factor, and then transplanting these cells into a syngeneic host mouse (FIG. 1A) (Hall et al., supra). Alternatively mesenchymal stem cells (MSCs), along with HSCs could be used. Although MSCs have considerable potential for regenerative power of the skeleton, a means is required to target these cells to sites in the skeleton where bone has been lost. In contrast, HSCs characteristically target specifically to two sites in mice: the HSC niche at the endosteal bone surface and the HSC niches at the marrow vascular surfaces. MSCs in the presence of HSCs can home to marrow vascular niches. These are the two major sites of bone loss in humans with osteoporosis. In humans, there also is a third clinically relevant site of targeting, namely large osteons that contain hematopoietic stem cell niches.

With respect to dosing for the PDGFB expression, three different promoters of varying strengths were evaluated: SFFV (a strong viral promoter in HSC (Meng et al., *Molecular therapy: the journal of the American Society of Gene Therapy.* 2012; 20(2):408-16)), PGK (a moderate strength promoter) (Meng et al., *Mol. Ther.* 20:408-416, 2012), and P200 (a truncated PGK promoter to create a weaker promoter). The strong SFFV promoter was included as a "positive control," in order to test whether the significant overexpression of PDGFB, as was the case for FGF2, would produce severe osteomalacia. The groups where the other two promoters were employed were used to eliminate the osteomalacia.

Example 2

Transplantation with Lenti SFFV-PDGFB Transduced Scar Cells Leads to Massive Trabecular Bone Formation but Induces Osteomalacia Four weeks following transplantation with lenti SFFV-PDGFB transduced Sca1+ cells, mice femur bone mineral density (BMD) was measured by pQCT analysis. The lenti SFFV-PDGFB treated animals showed greater trabecular bone formation compared with the control group (325 mg/cm$^3$ vs. 135 mg/cm$^3$, P<0.01; FIG. 1B). However, the newly formed bone is largely unmineralized, as examined by von Kossa staining, which stains calcium or mineralized bone (Sheenan, *Theory and Practice of Histotechnology*. The C.V. Mosby Company; 1980) (FIG. 1C, 1D). When the PDGFB-treated mice were divided into low serum PDGF-BB (<1000 pg/ml) and high serum PDGF-BB (>1000 pg/ml) subgroups, BMD in the low serum PDGF-BB group was significantly higher than in the high serum PDGF-BB group (402 vs. 290 mg/cm$^3$, P<0.05, FIG. 1E). These data suggest that high-level of PDGF-BB had some unintended effects on BMD so that the PDGF-BB dosage was important to achieve maximum bone formation.

Example 3

Reducing Transgene Expression with Weaker Promoters

Since the mice with low-level serum PDGF-BB showed higher BMD, PDGFB expression was reduced by using weaker promoters, PGK and P200 (FIG. 2A). To examine the potency of different promoters in Sca1+ cells, several GFP reporter lentiviral vectors were cloned. This system allowed accurate measurement of the strength of each promoter. For this purpose, Sca1+ cells were transduced with lenti SFFV-GFP, PGK-GFP, or P200-GFP at the same low MOI of 0.1. Three days after transduction, average GFP intensity was analyzed by FACS. Similar transduction efficiency was observed for the 3 vectors (FIG. 2B). As expected, GFP expression driven by the PGK promoter is ~85% lower than that driven by the SFFV promoter (15% vs. 100%), and GFP expression mediated by the P200 promoter is ~50% lower than PGK promoter (9% vs. 15%) (FIG. 2C). The creation of this system allowed investigation of the dosage effects of PDGF on bone formation (see below).

Example 4

Moderate Levels of PDGFB Expression Mediated by the PGK Promoter Leads to Substantial Bone Formation without Inducing Osteomalacia To investigate the dosage effects of PDGFB on bone formation, Sca1+ cells were transduced with lenti SFFV-PDGFB, PGK-PDGFB (SEQ ID NO: 26), P200-PDGFB or GFP control vectors, and then transplanted into mice following preconditioning with 6 Gy irradiation (n=8 per group). Because large marrow space was occupied by bony tissues that resulted in severe anemia, SFFV-PDGFB treated mice were sacrificed 7 weeks after transplantation. Animals from the other groups were healthy, and were maintained until the end of the experiment at 12 weeks after transplantation. Five weeks after transplantation, serum PDGF-BB levels in the SFFV-PDGFB mice were 2-3 fold higher than GFP control (1074±422 vs. 342±118 pg/ml, P<0.001, FIG. 3A). In contrast, no significant differences were observed in serum PDGF-BB levels between the PGK-PDGFB group (398±248 pg/ml), the P200-PDGFB group (285±49 pg/ml), and the control group (342±118 pg/ml, P>0.05).

Figure 3B:
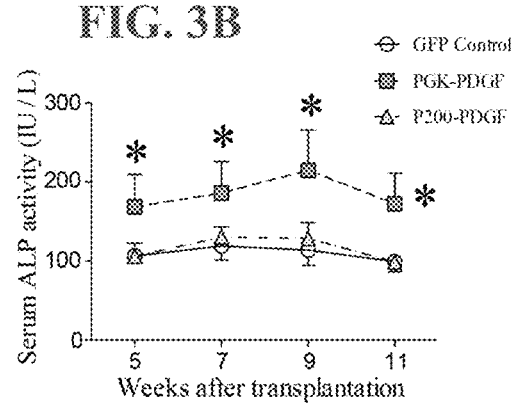
Figure 3C:
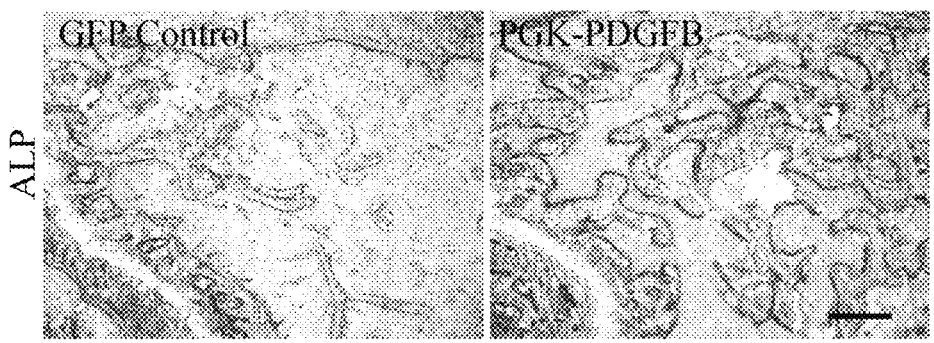
Figure 3D:
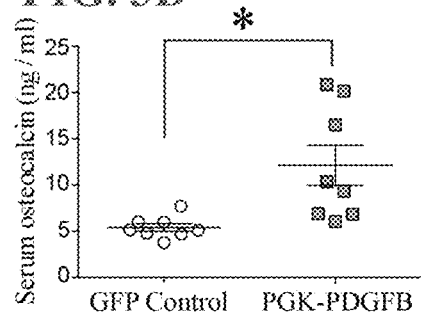

To monitor the dynamics of bone formation, the serum alkaline phosphatase (ALP) activity (a bone formation biomarker (Tobiume et al., *The Journal of clinical endocrinology and metabolism*. 1997; 82(7):2056-61)) was monitored at 5, 7, 9 and 11 weeks after transplantation (FIG. 3B). The ALP activity in the PGK-PDGFB group was 50% higher than GFP control animals from 5 weeks to 11 weeks post-transplantation. Consistent with this result, ALP activity was markedly increased in PGK-PDGFB treated mice throughout the marrow space compared to controls, as evident by ALP staining of femur sections (FIG. 3C). However, P200-PDGFB treated femur did not show any increases in ALP activity in both serum (FIG. 3B) and bone sections. Serum levels of osteocalcin, another bone formation biomarker, was measured. In keeping with the ALP data, it was found that serum osteocalcin levels increased ~150% in PGK-PDGFB treated mice relative to control (12.1±6.1 vs. 5.4±1.2 ng/ml; P<0.01) (FIG. 3D).

Micro-computed tomography (μCT) and histology analyses were conducted to investigate the bone structure. μCT analysis showed that after PGK-PDGFB treatment the femur was packed with thick and well-connected trabecular bone at both metaphysis and mid-shaft. In contrast, fewer trabeculae in metaphysis and virtually no trabeculae in midshiaft were observed in GFP control mice (FIG. 4A). Measurement of μCT bone structure parameters showed that relative bone volume, trabecular thickness, trabecular number and connectivity density were substantially increased in PGK-PDGFB treated mice compared to control (P<0.001 for all comparisons) (FIG. 4BC). Bone formation was only observed on the endosteal surface and not on the periosteal surface. Of note, the cortical bone volume was also increased by 20-30% (FIG. 4D). Cortical porosity was significantly decreased following treatment (4.5%±0.8 vs. 2.7%±0.2; P=0.0003).

To investigate whether PGK-PDGFB-mediated strong bone formation leads to incomplete mineralization, Von Kossa staining was conducted on a longitudinal thin bone section. Von Kossa staining of femur sections as well as similar osteoid width compared to control suggested that newly formed bone was fully mineralized in the PGK-PDGFB treated group (FIGS. 4F, 4G, and 4H). Consistent with the ALP and osteocalcin data, no obvious bone formation was observed in P200-PDGFB treated mice, as examined by both μCT and histology analyses.

Taken together, these data suggest that PGK-PDGFB treatment considerably increases mineralized bone formation, whereas a decrease of PDGFB expression by 50% with the use of the P200 promoter completely abrogates the bone-formation effects of PDGFB. These data strongly suggest that maintaining the PDGFB dose is important to promote the formation of fully mineralized bone at maximum levels.

Example 5

Moderate Levels of PDGFB Treatment do not Perturb the Ca$^{2+}$/Pi/PTH Axis

Figure 5A:
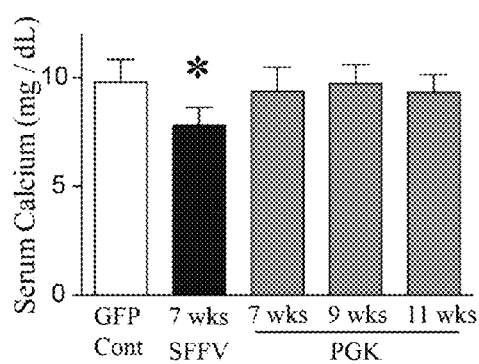
FIGS. 5A-5D. PGK-PDGFB treatment does not affect serum $Ca^{2+}$, phosphate, PTH, and FGF23 levels. (A) Serum calcium levels. Hypocalcaemia was observed in the SFFV-PDGFB treated animals, but not in the PGK-PDGFB treated animals. (B) Serum phosphate levels. Serum phosphate levels in the SFFV-PDGFB group at 7 weeks after transplantation were significantly lower than those in all other test groups (*P<0.05). (C) Serum PTH levels at 11 weeks after transplantation. GFP control vs. PGK-PDGFB, P=0.5, not significant. (D) Serum FGF23 levels at 11 weeks after transplantation. GFP control vs. PGK-PDGFB, P=0.5, not significant.
Figure 5B:
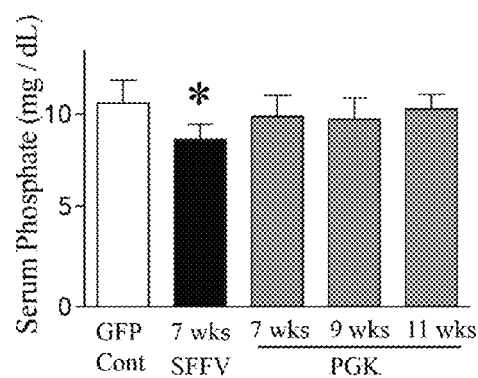
Figure 5C:
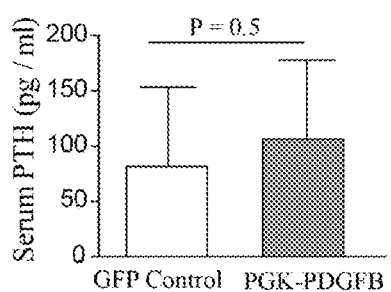
Figure 5D:
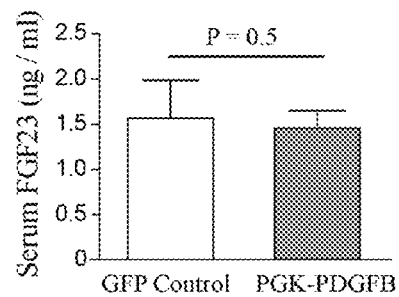

The previous FGF2-based therapy showed that rapid bone formation is associated with hypocalcemia, hypophosphatemia, and hyperparathyroidism (Hall et al., supra). Thus, serum calcium, phosphate, and parathyroid hormone (PTH) levels were measured after transplantation with PDGFB-transduced Sca1+ cells. Decreased serum calcium and phosphate levels were observed in SFFV-PDGFB treated mice relative to control, which may have attributed to the sickness of SFFV-PDGFB treated mice at 7 weeks after transplantation (FIG. 5AB). In contrast, moderate levels of PDGFB expression mediated by the PGK promoter did not affect serum calcium and phosphate levels examined at 7, 9, and 11 weeks after transplantation (FIG. 5AB). In addition, the serum levels in PGK-PDGFB mice of PTH and FGF23, a factor that controls phosphate homeostasis and is associated with osteomalacia (Liu et al., *Current opinion in nephrology and hypertension.* 2007; 16(4):329-35), were also indistinguishable from normal levels (FIGS. 5C and 5D). These data suggest that moderate levels of PDGFB delivered by lenti PGK-PDGFB-transduced hematopoietic cells induce bone formation without affecting the $Ca^{2+}$/Pi/ PTH axis.

Example 6

PGK-PDGFB Treatment Increases Bone Strength

Whole bone mechanical strength measurements are a major predictor of in vivo fracture resistance that needs to be addressed to prevent patient injury (Cole et al., *Clinical orthopaedics and related research.* 2011; 469(8):2139-49). To investigate the mechanical properties of bone following PGK-PDGFB treatment, three-point bending was performed. FIG. 6A shows the force-displacement curves of one representative sample from each test group. The force-displacement curves demonstrated the increased maximum load-to-failure as well as elevated stiffness of the bone in PGK-PDGFB treated group compared to control. PGK-PDGFB treatment led to a 45% increase in maximum load-to-failure of femurs (32.0±5.0 vs. 22.1±4.2 N, P=0.001) and 46% increase of stiffness (265.1±43.5 vs. 181.7±33.5 N/mm, P=0.0037) when compared to control femurs (FIG. 6B). Consistent with μCT and histology data, femurs from P200-PDGFB treated group exhibited biomechanical properties similar to that of femurs of GFP control mice (22.7±3.0 vs. 22.1±4.2 N, P=0.56). The increased maximum load-to-failure is positively correlated with bone mass increase in cortical and midshaft trabecular bone ($R^2$=0.75, P=0.0005. FIG. 6D, 6E). These data suggest that the new bone is functional and of high biomechanical quality.

Example 7

PDGFB Promotes Bone Formation by Increasing Proliferation and Osteogenic Potential of MSCs Bone formation is regulated by osteoblasts, which are differentiated from mesenchymal stem cells (MSCs). It was asked if the increased bone formation in the PGK-PDGFB group was the result of increased MSC proliferation. For this purpose, MSC numbers from femurs were measured at 12 weeks after transplantation using CFU-F and CFU-Ob assays. Indeed, an approximately 100% increase in the number of CFU-F and CFU-Ob colonies was observed in the femurs from PGK-PDGFB treated mice compared to control (FIG. 7AB). To consolidate this observation, the effects of PDGF-BB were investigated on in vitro MSC proliferation and bone nodule formation. Bone marrow cells were isolated from 6-week old mice and cultured in MSC medium supplemented with PDGF-BB at different concentrations (0, 0.3, 3 or 30 ng/ml). Both 3 ng/ml and 30 ng/ml PDGF-BB significantly increased MSC proliferation (FIG. 7C), suggesting that PDGF-BB promotes mesenchymal cell expansion. In comparison, PDGF-BB at 3 ng/ml significantly enhanced MSC-mediated bone nodule formation, whereas mineralized nodule formation was inhibited by high-level PDGF-BB at 30 ng/ml (FIG. 7D). This finding indicates that the increased bone formation following PGK-PDGFB treatment is attributable to enhanced proliferation and osteogenic potential of MSCs.

It was then asked whether increased MSC proliferation in femurs from PDGFB-treated mice would lead to enhanced osteoblast activities. To address this question, Runx2 and Sp7 (also known as osterix), both transcription factors are expressed by preosteoblasts (Xian et al., *Nature medicine.* 2012; 18(7):1095-101), and osteocalcin, a marker of mature bone-forming cells, were stained (Minkin, *Calcified tissue international.* 1982; 34(3):285-90). As expected, expression levels of Runx2 and Sp7 as well as osteocalcin were considerably increased in PGK-PDGFB treated tibias compared to control (FIG. 7E). To consolidate these findings, osteogenesis-related gene expression was measured in the tibias at 12 weeks post transplantation. Consistent with increases in serum ALP activity, the expression of Alp mRNA was increased ~7-fold after PGK-PDGFB treatment (FIG. 7F). In addition, Spp1 (also known as osteopontin) and Col1a1 expression also increased ~22-fold and 5-fold, respectively (FIG. 7F). Moreover, bone formation growth factors Bmp2 and Bmp4 were upregulated by ~3 fold in PGK-PDGFB treated group (FIG. 7F). Consistent with the immunostaining data, the expression of preosteoblast marker genes Cbfa1, which encodes Runx2, and Sp7, which encodes osterix, was also increased by ~5-fold and 7-fold, respectively, in comparison to control (FIG. 7F). Taken together, these results suggest that PDGF-BB increased bone formation by promoting MSC expansion, increasing osteoblast activities, and upregulating the expression of a battery of osteogenesis-related genes.

Example 8

PDGFB Increases Bone Remodeling

Figure 8A:
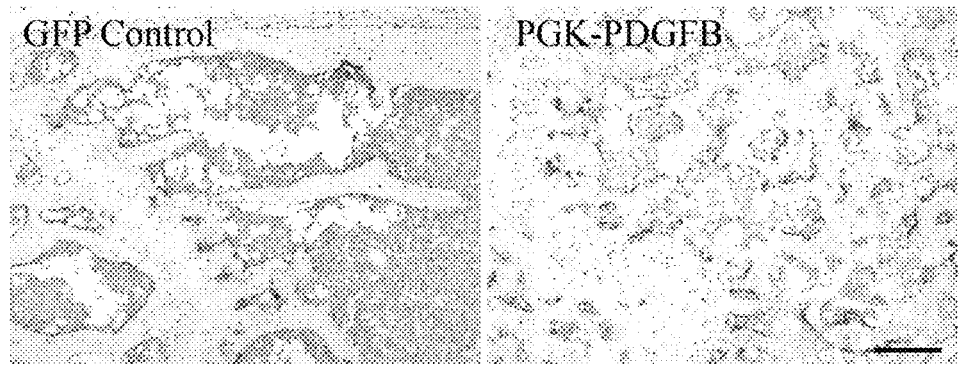
FIGS. 8A-8C. Sca1+ Lenti-PGK-PDGFB treatment increased bone turnover. (A) TRAP staining of the distal femur of GFP control or PGK-PDGFB treated mice. TRAP-expressing osteoclasts were stained red. Scale bar: 200 μm. (B) Serum CTX-1 levels (a biomarker of bone resorption) at 9 weeks after transplantation. PGK-PDGFB treated mice showed significantly increased serum CTX-1 levels (*P<0.05). (C) qPCR analysis of osteoclastogenesis-related genes in the tibias. GFP control vs. PGK-PDGFB, *P<0.05. N=8.
Figure 8B:
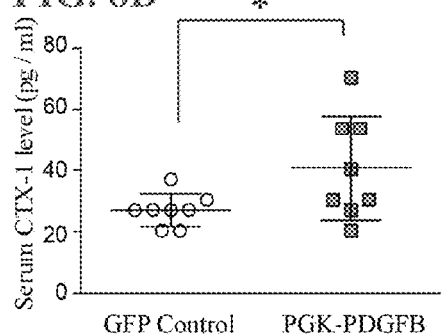
Figure 8C:
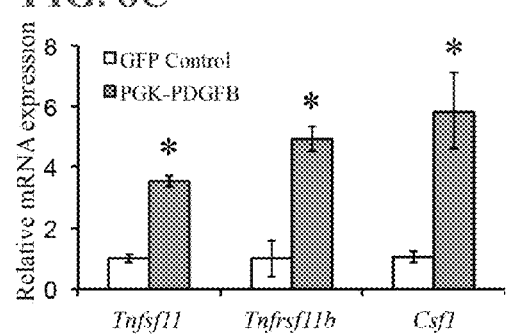

Finally, it was asked whether osteoclastogenesis was affected by PDGFB treatment. For this purpose, the activity of tartrate-resistant acid phosphatase (TRAP), a specific marker for osteoclasts, was analyzed (Minkin, *Calcified tissue international.* 1982; 34(3):285-90). Of interest, the number of TRAP+ osteoclasts was significantly increased in the femur of PGK-PDGFB mice, in which the bone surface was often covered by osteoclasts (FIG. 8A). This observation, together with the finding that PDGFB treatment leads to heightened osteoblast activities at bony surfaces, suggests that PDGFB treated animals have increased bone remodeling. Consistent with increased TRAP activity, serum CTX-1, a biochemical marker of bone turnover (Tyagi et al., *PloS one.* 2012; 7(9):e44552), increased by 30-40% in PGK-PDGFB mice compared to control (P<0.05) (FIG. 8B). To consolidate these findings, osteoclastogenesis-related gene expression also was measured in the mouse tibias at 12 weeks after transplantation (FIG. 8C). Tnfsf11, which encodes Rank1, and Csf1, which encodes M-CSF, were each upregulated by ~3 fold and 6 fold, respectively. Moreover, Tnfrsf11b, the gene encoding osteoprotegerin (Opg) that serves as an antagonist to Rank1, was also increased. Taken together, these results suggest that PDGFB treatment also increases osteoclast activities to promote bone remodeling.

This study disclosed herein is an example of the unique capabilities of cell therapy. It is demonstrated that in normal mice, after myeloablation and a single intravenous injection of HSCs that were engineered to overexpress PDGFB driven by a moderate promoter, specifically the PGK promoter, there is a rapid, persistent and robust formation of mineralized bone leading to an increase in bone strength (+45%) as measured by three-point bending. Importantly, net bone formation was seen at all three sites where bone is lost during osteoporosis of aging in humans: 1) at the end of cortical surface, 2) cortical canals, and 3) in the trabecular compartment. One of the most remarkable findings with respect to the sites of bone formation was a 20-fold increase in trabecular connections that have mechanical performance implications. In relation to this, evidence was found for de novo bone formation in the marrow cavity; trabecular bone was found in situ where no trabeculae existed in the control animals. Accordingly the disclosed strategy could completely replace all bone lost in the osteoporotic process, and thus rejuvenate the skeleton.

One aspect of the disclosed therapy was stem cell targeting. Hematopoietic stem cells were used, rather than mesenchymal stem cells. MSCs also have the capacity to produce large amounts of bone. However, these cells have only been used for local therapy (Chandra et al., *Journal of cellular biochemistry.* 2010; 111(2):249-57) and require appropriate targeting mechanisms. HSCs are able to home to the bone marrow and specifically engraft at the niches where aging-induced bone loss occurs. On the other hand, MSCs in the presence of HSCs, can form partners that would enhance the homing and engraftment of both stem cells to the marrow vascular stem cell niches near the endostea bone surface (Méndez, et al., *Nature* 466:829-834, 2010). Therefore, MSCs can also be used in combination with HSCs. The ratio of MSCs to HSCs can be 0.01 to 0.99. Alternatively, MSCs, after appropriate but yet-to-identified modifications to enhance its ability to home and stay at the marrow niche, can also be used.

Osteomalacia was observed with a high dose of FGF2, possibly because of a specific mineralization defect or the attending secondary hyperparathyroidism. The FGF2-induced severe osteomalacia was reproduced by using a high dose of PDGF-BB. This is consistent with the mineralization defect due to an inordinately high stimulus for bone formation as opposed to a specific defect in the mineralization process. However, osteomalacia was rescued completely by reducing the amount of PDGF-BB. Without being bound by theory, these findings are consistent with the concept that calcium deficiency can be created by an increased loss from the serum pool of calcium as well as a decreased input into the serum pool of calcium.

A potential problem of developing anabolic therapies is a resistance to therapy over time (McClung et al., *ASBMR Annual Meeting.* 2014, abstract #1152). Although this issue was not tested directly, no decrease was detected in the increment in alkaline phosphatase over the three-month experimental period. Moreover, in the context of the experimental animal (normal bone mass), bone formation was occurring robustly despite the fact the additional bone was not mechanically required. Thus, the therapy could cause a large increment of skeletal mass. The disclosed stem cell gene therapy could be utilized in combination with a specific exercise program to enhance the trabecular compartment at mechanically appropriate sites. The large increment in trabecular connections also could provide a model to further study the mechanisms of trabecular connections.

MSCs engineered to overexpress BMP 2/4 were much more effective in filling in a calvarial critical size defect than stem cells alone (Lau et al., *Calcified tissue international.* 2009; 85(4):356-67). Consequently, BMP 2/4 was the first growth factor that tested in the HSC-based transplantation scheme. However, no positive effect was identified on bone formation with BMP 2/4 (Hall et al., *The journal of gene medicine.* 2009; 11(10):877-88). The one growth factor that did show a positive response in prior work was FGF2 which increased hematopoietic stem cell proliferation (Hall et al., *Molecular therapy* 15(10):1881-1889, 2007) (de Parseval et al., *Cytokine.* 5(1):8-15, 1993). PDGF-BB also increases hematopoietic stem cell proliferation (Kasperk et al., *Growth factors.* 3(2):147-158, 1990) (de Haan et al., *Developmental cell.* 4(2):241-251, 2003). Without being bound by theory, the transplanted stem cells may need to have a competitive advantage of increased proliferation by growth factor induced autocrine/paracrine mechanisms.

PDGF-BB has been shown to directly stimulate bone resorption (Tasjian et al., *Endocrinology.* 1982; 111(1):118-24). In the model disclosed herein, evidence was found for elevated Csf1 and Tnfsf11 gene expression together with an increased number of TRAP$^r$ osteoclasts findings, which are consistent with increased bone resorption. Inasmuch as the serum PTH was normal in the modest activity promoter (PGK) group, this finding is interpreted to be consistent with the innate ability of PDGF-BB to stimulate bone resorption (Mitlak et al., *Journal of bone and mineral research* 11(2): 238-247, 1996). Such an increase in bone resorption is indicative of an increase in bone remodeling which has the potential advantage of decreasing bone age. Without being bound by theory, this could improve the mechanical performance of bone since in aging humans there is an increase in risk for fracture above and beyond the low bone density, a finding that has been attributed to in part to poor material properties of aging bone (Mosekilde et al., *Bone.* 8(2):79-85, 1987).

The therapeutic regimen has the requirement of total body irradiation transplanted HSCs homing and engraftment. Large efforts have been made in the past to eliminate or reduce this preconditioning with only modest success (Blaise & Castagna. *Hematology/the Education Program of the American Society of Hematology. American Society of Hematology Education Program.* 2012: 237-245, 2012. The disclosed results suggest this is feasible because only a 5% engraftment of donor cells would lead to substantial increase in bone formation.

There is another potential application of the therapeutic regimen disclosed herein, namely transplantation osteoporosis and fracture (McClune et al., *Current osteoporosis reports.* 11(4):305-310, 2013). Without being bound by theory, by utilizing the CRISPR/Cas system to insert a therapeutic gene at a safe site and using this transcriptionally regulated dosing procedure, the therapeutic regimen can be applied as a preventative therapy for transplantation-induced osteoporosis that has a high risk of occurring after transplantation (McClune et al., *Seminars in hematology.* 49(1): 59-65, 2012). This therapy as a potential application for patients undergoing bone marrow transplantation for medical reasons inasmuch as they are at high risk for osteoporosis and fracture (Xerxes-Pundole et al., *ASBMR Annual Meeting.* 2014, abstract #1084).

Figure 9:
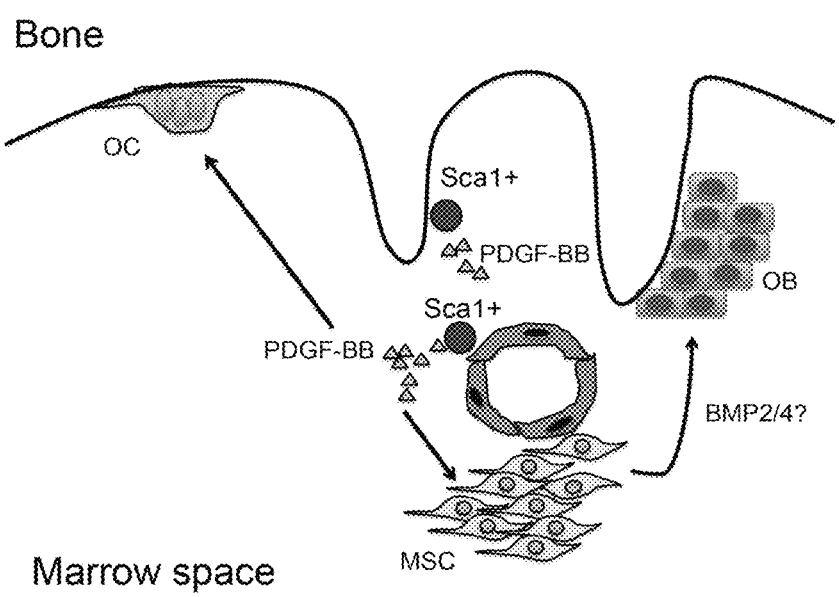
FIG. 9. Schematic diagram of PDGFB-Sca1+ cells induced bone formation. PDGFB-Sca1+ cells were homing and engrafted to hematopoietic stem cell niche at the endosteal surface and in the trabecular compartment (perivascular niches). Without being bound by theory, PDGF-BB released from Sca1+ cells stimulates MSC proliferation and recruits MSCs to the niches, while elevated growth factors (e.g. BMP2/4) in response to PDGF-BB facilitates MSCs differentiation towards bone cells. OB, osteoblast; OC, osteoclast; GF, growth factor.

Without being bound by theory, one proposed mechanism of action for our therapeutic regimen is depicted in FIG. 9. Following transplantation, PDGFB expressing Sca1$^+$ cells were homing and engrafted to hematopoietic stem cell niche at the endocortical surface and at the trabecular surface. PDGF-BB released from Sca1+ cells stimulated MSC proliferation as well as recruits MSCs to the niches; PDGF treatment was associated with an increase of BMP2 and BMP4, while the elevated BMPs facilitate MSCs differentiation towards bone cells.

The transplantation of mouse hematopoietic stem cells engineered to express PDGF-BB by the PGK promoter in the normal mouse resulted in a rapid, persistent and robust formation of mineralized bone which leading to a considerable increase in bone strength. The PDGFB expressing HSCs targeted the niches at the endosteal surface and at the trabecular compartment (perivascular niches), where bone is lost in the human osteoporotic skeleton. The PGK promoter drives the expression of optimal levels of PDGF-BB in bone marrow without affecting PDGF-BB baseline levels in circulation. In the trabecular compartment there was a large increase in trabecular connections and also evidence of de novo trabecular formation, findings with positive mechanical applications. These data suggest that HSC-based PDGFB treatment can be used therapeutically for several bone loss-related disorders.

Example 9

Figure 10A:
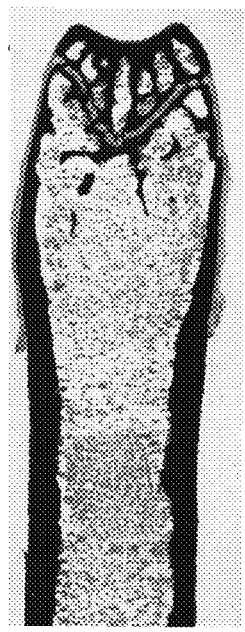
FIGS. 10A-10B. Digital image of increased bone formation in the OVX mice seven weeks after PDGFB overexpressing Sca1+ cells transplantation. Representative von Kossa staining showed that significantly increased trabecular bones were seen at the metaphysis of the femur in the PGK-PDGFB treated mice (B) compared to the OVX control mice (A).
Figure 10B:
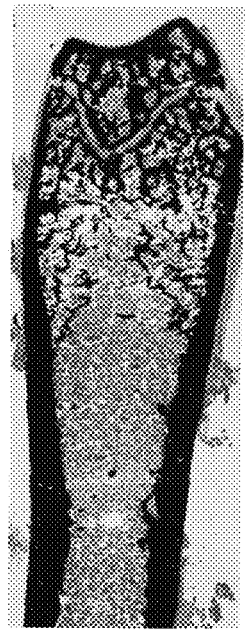

Transplantation of PDGFB-Overexpressing Sca1+ Cells into Ovariectomy-Induced Bone Loss Mouse Model can Promote Systemic Bone Formation Ovariectomy (OVX) surgery was performed on 3-month old C57/B6 mice. Four weeks later, mice received 6 Gy irradiation, and 1×10⁶ Lenti-GFP or Lenti-PGK-PDGFB transduced Sca1+ cells were transplanted into OVX mice. Seven weeks later, mice were euthanized and histology was performed on femurs to assess the bone formation effects. There was significantly increased trabecular bone formation on the metaphysis in the PGK-PDGFB treated group (see FIG. 10).

Example 10

Use of PDGF-DSS6 Fusion Protein for Treating Osteoporosis

It has been reported that DSS6 (six repetitive sequences of aspartate, serine, serine) is a peptide that has strong binding affinity to bone surface thus can target bone tissue. A PDGFB-DSS6 fusion protein was created by conjugating PDGFB with DSS6. It was determined if systemic injection of PDGF-DSS6 fusion protein was able to promote bone formation in an osteoporosis mouse model.

Ovariectomy surgery was performed on C57/B6 female mice. Eight weeks later, saline or 1 mg/kg PDGF-DSS6 fusion was administered intravenously every week for eight continuous weeks. Mice were then euthanized for microCT analysis. The cortical thickness of the midshaft of the tibias was significantly increased in the PDGF-DSS6 treated group. The pore size of the cortical bones showed a trend of reduction but was not significant yet (FIGS. 11A-11B).

Example 11

Materials and Methods

Mice:
Six-week old female C57BL/6 mice were purchased from the Jackson laboratory (Bar Harbor, Me.). All experimental protocols were approved.

Bone Marrow Sca1+ Cells Isolation:
Bone marrow Sca1+ cell isolation was performed as previously described (Meng et al., *PLoS One* 7(5):e37569, 2012). Briefly, bone marrow cells were harvested from femurs and tibias, and Sca1+ cells were purified using Sac1 MACS® magnetic beads (MiltenyiBiotec, Auburn, Calif.). Prior to viral transduction, cells were cultured 48 hours in Iscove's modified Dulbecco's medium (IMDM, Invitrogen) containing 10% fetal bovine serum (Invitrogen) and 100 ng/ml of human TPO, mouse SCF, human FL, human IL-3, and G-CSF.

Lentiviral Vectors and Transduction of Sca1+ Cells:
Human PDGFB ORF (open reading frame) was subcloned into a lentiviral vector under the control of the spleen focus-forming virus (SFFV) promoter, the phosphoglycerate kinase (PGK) promoter, or the truncated PGK promoter (P200). Lentiviral packaging was performed as previous described (Meng et al., *PLoS One* 7(5):e37569, 2012). Briefly, lentiviral vectors were produced by transient transfection of the vector plasmid in human 293T cells along with helper plasmid (CMVdR8.74) and envelope plasmid (MD.G). Sca1+ cells were transduced once at a multiplicity of infection (MOI) of 2 for 6 h in 6-well non-TC treated plates precoated with RetroNectin (Takara, Otsu, Japan). Transduction efficiency was approximately 70% by flow cytometry and real-time PCR analysis.

Transplantation:
Recipient mice were irradiated from a $^{60}$Co source (Eldorado model, Atomic Energy of Canada, Commercial Products Division, Ottawa, Canada) at a single dose of 6 Gy (1 Gy/minute). Twenty-four hours later, 1×10⁶ lentiviral transduced Sca1+ cells were resuspended in 200 μl IMDM medium and transplanted into each mouse via tail vein injection.

Flow Cytometry:
To compare the strength of promoters in mouse hematopoietic cells, Sca1+ cells were transduced with lentiviral vectors SFFV-GFP, PGK-GFP, or P200-GFP at the same MOI (0.1). Three days later, cells were collected and resuspended in phosphate-buffered solution. 50,000 cells from each sample were analyzed on a FACSAria II flow cytometer (BD Biosciences, San Jose, Calif.).

Histology and Immunostaining:
Mouse femurs were fixed in 1% paraformaldehyde (PFA) containing 0.1% picric acid overnight at 4° C., and frozen sections were obtained as previously described (Hall et al., *The journal of gene medicine*. 11(10):877-888, 2009). Briefly, undecalcified femurs were embedded in SCEM embedding medium (Section Lab Co., Japan). After trimming, the sample surface was covered with the Cryofilm™ type 2C adhesive film (Section Lab Co., Japan) and 5 μm thickness sections were cut using Cryostat (Leica CM3050S). The sections were used for measuring alkaline phosphatase (ALP) activity and tartrate-resistant acid phosphatase (TRAP) activity, von Kossa staining, and immunohistochemistry. ALP activity staining was performed using the Alkaline Phosphatase Staining Kit II (Stemgent). For TRAP activity staining, sections were preincubated for 10 minutes in TRAP solution followed by 5 minutes of incubation in development solution (2 mg/ml pararosanilline and 20 mg/ml sodium nitrate). For von Kossa staining, sections were incubated with 1% Silver Nitrate solution for 45 minutes first, then rinsed thoroughly in distilled water and incubated with 5% thiosulfate solution for 5 minutes. After washes, sections were counterstained with hematoxylin and eosin. For immunohistochemical staining, sections were blocked with 3% hydrogen peroxide for 10 minutes followed by 4% normal horse serum for 30 minutes, and subsequently incubated overnight at 4° C. with primary antibodies against Runx2 (Abcam, USA), Sp7 (Abcam, USA), or Osteocalcin (Takara, USA). The slides were then incubated with biotinylated secondary antibody (Vector Laboratories) and developed with DAB reagent (Vector Laboratories). All the images were captured using an Olympus BX51 microscope system (Olympus, USA).

pQCT Analysis:

Femurs were fixed in 4% PFA overnight and then stored in PBS with 0.1% sodium azide at 4° C. Trabecular bone mineral density (BMD) was measured using an XCT 960M with XCT software version 5.40 (Roche Diagnostics, Basel, Switzerland) as previously described (Meng et al., *PLoS One* 7(5):e37569, 2012). Trabecular BMD value was calculated by dividing trabecular mineral content by the trabecular bone volume and expressed as milligrams per cubic centimeter.

μCT Analysis:

μCT analysis of the femoral bone was performed using a Scanco VivaCT 40 instrument (Scanco Medical AG, Briitisellen, CH). Femurs were scanned at an isotropic voxel size of 10.4 μm$^3$, and energies of 55 keV and 70 keV were used for scanning metaphysis and midshaft, respectively. For metaphyseal scans, the region of interest was a set distance proximal to the growth plate after the bone was normalized for any variations in length. Midshaft scans were also normalized for any variations in bone length. Trabecular bone was segmented at a density of greater than 220 mg/cm$^3$ and the cortical bone segmented at a density of greater than 260 mg/cm$^3$.

Serum Analysis:

Serum PDGF-BB, serum PTH, serum FGF23, serum osteocalcin, and serum C-Telopeptide of Type I Collagen (CTX-1) levels were measured using PDGFB ELISA kit (R&D Systems, Minneapolis, Minn.), PTH ELISA kit (RayBiotech, Norcross, Ga.), FGF23 ELISA kit (Millipore, Temecula, Calif.), osteocalcin ELISA kit (Biomedical technologies Inc., Ward Hill, Mass.) and CTX-1 ELISA kit (Novateinbio, Woburn, Mass.), respectively. Serum calcium and phosphate were measured using colorimetric assay kits (Biovision, Milpitas, Calif.). Serum alkaline phosphatase (ALP) activity was measured by QuantiChrom ALP kit (BioAssay Systems, Hayward, Calif.).

Quantitative Reverse Transcriptase Polymerase Chain Reaction (RT-PCR):

RNA was extracted from tibias using QIAzol® lysis reagent (Qiagen) followed by purification with RNeasy® kit and DNase treatment (Qiagen) according to the manufacturer's instruction. Reverse transcription into cDNA was performed using EasyScript™ Reverse Transcript kit (Applied Biological Materials, Canada). Real-time PCR was performed using SYBR® Green PCR Master Mix (Applied Biosystems) on 7500 Fast Real-Time PCR System (Applied Biosystems). The samples were normalized to GAPDH expression. Primer sequences are listed below:

| Primer sequences used for qRT-PCR analysis | | |
|---|---|---|
| Gene | Primer sequences | SEQ ID NO: |
| Gapdh | Forward Primer: 5'-GGGTGTGAACCACGAGAAAT-3' | 4 |
|  | Reverse Primer: 5'-CCTTCCACAATGCCAAAGTT-3' | 5 |
| Alp | Forward Primer: 5'-CTTGACTGTGGTTACTGCTG-3' | 6 |
|  | Reverse Primer: 5'-GAGCGTAATCTACCATGGAG-3' | 7 |
| Bmp2 | Forward Primer: 5'-TGGAAGTGGCCCATTTAGAG-3' | 8 |
|  | Reverse Primer: 5'-TGACGCTTTTCTCGTTTGTG-3' | 9 |
| Bmp4 | Forward Primer: 5'-CCTCAAGGGAGTGGAGATTG-3' | 10 |
|  | Reverse Primer: 5'-GACTACGTTTGGCCCTTCTG-3' | 11 |
| Sp7 | Forward Primer: 5'-AGCTCACTATGGCTCCAGTCC-3' | 12 |
|  | Reverse Primer: 5'-GCGTATGGCTTCTTTGTGCCT-3' | 13 |
| Cbfa1 | Forward Primer: 5'-CCAAGAAGGCACAGACAGAA-3' | 14 |
|  | Reverse Primer: 5'-ATACTGGGATGAGGAATGCG-3' | 15 |
| Spp1 | Forward Primer: 5'-GGTGATAGCTTGGCTTATGGACTG-3' | 16 |
|  | Reverse Primer: 5'-GCTCTTCATGTGAGAGGTGAGGTC-3' | 17 |
| Col1a1 | Forward Primer: 5'-GAGCGGAGAGTACTGGATCG-3' | 18 |
|  | Reverse Primer: 5'-TACTCGAACGGGAATCCATC-3' | 19 |
| Tnfsf11 | Forward Primer: 5'-CAGCATCGCTCTGTTCCTGTA-3' | 20 |
|  | Reverse Primer: 5'-CTGCGTTTTCATGGAGTCTCA-3' | 21 |
| Tnfrsf11b | Forward Primer: 5'-ACCCAGAAACTGGTCATCAGC-3' | 22 |
|  | Reverse Primer: 5'-CTGCAATACACACACTCATCACT-3' | 23 |
| Csf1 | Forward Primer: 5'-GGCTTGGCTTGGGATGATTCT-3' | 24 |
|  | Reverse Primer: 5'-GAGGGTCTGGCAGGTACTC-3' | 25 |

Colony Forming Unit Fibroblast (CFU-F) and Colony Forming Unit Osteoblast (CFU-Ob) Assay:

At 12 weeks after transplantation, bone marrow cells were harvested from long bones of PGK-PDGFB treated mice and control mice, and cell number was counted after lysis of red blood cells. 2×10$^5$ marrow cells were plated into 0.01% gelatin-coated plates for CFU-F and CFU-Ob assay. For CFU-F assay, cells were maintained in Mesenchymal Stem Cell Medium Kit (Applied Biological Materials) for 14 days, and stained with crystal violet. For CFU-Ob assay, cells were maintained in osteogenic medium (α-MEM supplemented with 10% FBS, 100 U/ml penicillin/streptomycin, 5 mM β-glycerophosphate, 10 μM dexamethasone, and 50 μg/ml ascorbic acid, and 20 ng/ml BMP2) for 21 days, and mineralized nodules were stained with Alizarin red.

In Vitro MSC Culture:

Mouse MSCs were isolated and cultured using standard protocol (Hall et al., *J Gene Med.*, 13:77-88, 2011). Bone marrow cells were obtained from 6 weeks old mice by flushing the femurs and tibia with α-MEM medium. After lysis of red blood cells, bone marrow cells were plated in α-MEM medium supplemented with 2% FBS, 5% serum replacement, 100 IU/ml penicillin and 100 μg/ml streptomycin. After 24 hours, non-adherent cells were removed by washing with PBS and adherent cells were continuously cultured until being almost confluent. Subsequent passaging was performed, and cells were used after passage 3. For the MSC proliferation assay, $1 \times 10^5$ cells were plated in each well of 6-well plates with α-MEM complete medium supplemented with PDGF-BB at different concentrations (0, 0.3, 3 or 30 ng/ml). Culture medium was changed every two days. Cell number was counted every three days. For bone nodule assay, $1 \times 10^5$ cells were maintained in osteogenic medium (α-MEM supplemented with 10% FBS, 100 U/ml penicillin/streptomycin, 5 mM β-glycerophosphate, 10 μM dexamethasone, and 50 μg/ml ascorbic acid, and 20 ng/ml BMP2) for 21 days. Culture medium was changed every two days, and mineralized nodules were stained with Alizarin red.

Mechanical Testing:

The mechanical strength of the femurs was evaluated at midshaft by the three-point bending approach, using an Instron DynaMight® 8841 servohydraulic tester (Instron, Norwood, Mass.). Bones were stored frozen in saline-soaked gauze, and thawed and rehydrated in saline before testing. The femur was positioned on the tester with the anterior aspect upwards on supports that were 7 mm apart. The bone was preloaded to 1 N and the midshaft then loaded to failure using a blade excursion rate of 5.0 mm/sec.

Statistical Analysis:

Data are presented as mean±standard deviation (SD). Data comparison between two groups was analyzed using Student's t test. Data comparison between more than two groups was analyzed using one-way ANOVA followed by Turkey's multiple comparisons test. The linear relationship was measured between maximum load force and femur cortical bone volume, as well as between maximum load force and trabecular bone volume in the midshaft using Pearson's correlation coefficient. A P value of <0.05 was considered statistically significant. Sample sizes were n=8 for each group, or specifically indicated if different.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of increasing bone mass and strength in a subject, comprising:
administering to the subject a therapeutically effective amount of hematopoietic stem cells transformed with a recombinant nucleic acid molecule encoding platelet derived growth factor (PDGF)B operably linked to a phosphoglycerate kinase-1 (PGK) promoter, wherein the transformed hematopoietic stem cells express PDGFB within the vascular niches in the marrow cavity; thereby increasing bone mass and strength in the subject.

2. The method of claim 1, wherein the subject is human, and wherein a serum concentration of PDGFB is 0.1 to 30 ng/ml at five weeks following administration of the hematopoietic stem cells.

3. The method of claim 1, wherein increasing bone mass and strength comprises an increase in trabecular number, an increase in trabecular connectivity, an increase in de novo trabecular bone formation, an increase in endosteal bone formation, and/or a decrease in bone porosity.

4. The method of claim 1, wherein the hematopoietic stem cell is transformed with a vector comprising the recombinant nucleic acid molecule.

5. The method of claim 4, wherein the vector is a retroviral vector, an adenoviral vector, or an adeno-associated vector (AAV).

6. The method of claim 5, wherein the retroviral vector is a lentiviral vector.

7. The method of claim 1, wherein the recombinant nucleic acid molecule is integrated into a safe harbor locus in a genome of the hematopoietic stem cell.

8. The method of claim 7, wherein the recombinant nucleic acid molecule is integrated into the safe harbor locus using CRISPR gene editing technology.

9. The method of claim 4, wherein the vector further comprises a suicide gene.

10. The method of claim 9, wherein the suicide gene is HSV thymidine kinase (HSV-TK).

11. The method of claim 1, wherein the subject has a bone disease or disorder that affects bone strength.

12. The method of claim 11, wherein the subject has a metabolic bone disease.

13. The method of claim 11, wherein the subject has osteoporosis, osteogenic imperfecta, or avascular necrosis.

14. The method of claim 1, wherein the subject has cancer.

15. The method of claim 14, wherein the subject is preconditioned using total or local body irradiation, or chemically induced myeloablation, prior to administration of the hematopoietic stem cells.

16. The method of claim 1, wherein the hematopoietic stem cells produce about 1 to about 10 ng per $10^6$ cells of PDGFB in 24 hours.

17. The method of claim 1, wherein the hematopoietic stem cells produce about 2 to about 6 ng per $10^6$ cells of PDGFB in 24 hours.

18. The method of claim 1, wherein the hematopoietic stem cells are autologous.

19. The method of claim 1, wherein the hematopoietic stem cells are Sca1 positive hematopoietic stem cells.

20. The method of claim 1, wherein the subject is preconditioned prior to administration of the hematopoietic stem cells.

21. The method of claim 20, wherein the subject is preconditioned using total or local body irradiation prior to administration of the hematopoietic stem cells.

22. The method of claim 20, wherein the subject is preconditioned using chemically induced myeloablation prior to administration of the hematopoietic stem cells.

23. The method of claim 1, wherein the hematopoietic stem cells are administered intravenously.

24. The method of claim 5, wherein the retroviral vector is a Molony leukemia virus (MLV) vector.

25. The method of claim 1, wherein the hematopoietic stem cells express an amount of PDGFB sufficient to increase bone strength.

* * * * *

SEQUENCE LISTING

```
<160> NUMBER OF SEQ ID NOS: 34

<210> SEQ ID NO 1
<211> LENGTH: 3393
<212> TYPE: DNA
<213> ORGANISM: Homo sapiens

<400> SEQUENCE: 1
cctgcctgcc tccctgcgca cccgcagcct cccccgctgc ctccctaggg ctcccctccg      60
gccgccagcg cccattttc  attccctaga tagagatact ttgcgcgcac acacatacat     120
acgcgcgcaa aaaggaaaaa aaaaaaaaaa agcccaccct ccagcctcgc tgcaaagaga     180
aaaccggagc agccgcagct cgcagctcgc agctcgcagc ccgcagcccg cagaggacgc     240
ccagagcggc gagcgggcgg gcagacggac cgacggactc gcgccgcgtc cacctgtcgg     300
ccgggcccag ccgagcgcgc agcgggcacg ccgcgcgcgc ggagcagccg tgcccgccgc     360
ccgggccccg cgccagggcg cacacgctcc cgccccccta cccggcccgg gcgggagttt     420
gcacctctcc ctgcccgggt gctcgagctg ccgttgcaaa gccaactttg gaaaaagttt     480 tttggggag  acttgggcct tgaggtgccc agctccgcgc tttccgattt tggggccctt     540
tccagaaaat gttgcaaaaa agctaagccg gcgggcagag gaaaacgcct gtagccggcg     600
agtgaagacg aaccatcgac tgccgtgttc cttttcctct tggaggttgg agtccctgg      660 gcgcccccac acggctagac gcctcggctg gttcgcgacg cagcccccg  gccgtggatg     720 ctcactcggg ctcgggatcc gcccaggtag cggcctcgga cccaggtcct gcgcccaggt     780
cctcccctgc ccccagcga cggagccggg gccggggcg  gcggcgcccg ggggccatgc     840
gggtgagccg cggctgcaga ggcctgagcg cctgatcgcc gcggacccga gccgagccca     900
cccccctccc cagcccccca cctggccgc  ggggcggcg  cgctcgatct acgcgtccgg     960
ggccccgcgg ggccgggccc ggagtcggca tgaatcgctg ctgggcgctc ttcctgtctc    1020
```

```
tctgctgcta cctgcgtctg gtcagcgccg aggggggaccc cattcccgag gagctttatg    1080
agatgctgag tgaccactcg atccgctcct tgatgatct  ccaacgcctg ctgcacggag    1140
accccggaga ggaagatggg gccgagttgg acctgaacat gacccgctcc cactctggag    1200
gcgagctgga gagcttggct cgtggaagaa ggagcctggg ttccctgacc attgctgagc    1260
cggccatgat cgccgagtgc aagacgcgca ccgaggtgtt cgagatctcc cggcgcctca    1320
tagaccgcac caacgccaac ttcctggtgt ggccgccctg tgtggaggtg cagcgctgct    1380
ccggctgctg caacaaccgc aacgtgcagt gccgccccac ccaggtgcag ctgcgacctg    1440
tccaggtgag aaagatcgag attgtgcgga agaagccaat ctttaagaag gccacggtga    1500
cgctggaaga ccacctggca tgcaagtgtg agacagtggc agctgcacgg cctgtgaccc    1560
gaagcccggg gggttcccag gagcagcgag ccaaaacgcc ccaaactcgg gtgaccattc    1620
ggacggtgcg agtccgccgg ccccccaagg gcaagcaccg gaaattcaag cacacgcatg    1680
acaagacggc actgaaggag acccttggag cctaggggca tcggcaggag agtgtgtggg    1740
cagggttatt taatatggta tttgctgtat tgccccatg  gggtccttgg agtgataata    1800
ttgtttccct cgtccgtctg tctcgatgcc tgattcggac ggccaatggt gcttccccca    1860
cccctccacg tgtccgtcca cccttccatc agcgggtctc ctcccagcgg cctccggcgt    1920
cttgcccagc agctcaagaa gaaaaagaag gactgaactc catcgccatc ttcttcccctt    1980
aactccaaga acttgggata gagtgtgag  agagactgat ggggtcgctc tttgggggaa    2040
acgggctcct tccctgcac  ctggcctggg ccacacctga gcgctgtgga ctgtcctgag    2100
gagccctgag gacctctcag catagcctgc ctgatccctg aaccctggc  cagctctgag    2160
gggaggcacc tccaggcagg ccaggctgcc tcggactcca tggctaagac cacagacggg    2220
cacacagact ggagaaaacc cctcccacgg tgcccaaaca ccagtcacct cgtctccctg    2280
gtgcctctgt gcacagtggc ttcttttcgt tttcgttttg aagacgtgga ctcctcttgg    2340
tgggtgtggc cagcacacca agtggctggg tgccctctca ggtgggttag agatggagtt    2400
tgctgttgag gtggctgtag atggtgacct gggtatcccc tgcctcctgc caccccttcc    2460
tccccacact ccactctgat tcacctcttc ctctggttcc tttcatctct ctacctccac    2520
cctgcatttt cctcttgtcc tggcccttca gtctgctcca ccaggggct  cttgaacccc    2580
ttattaaggc cccagatgat cccagtcact cctctctagg gcagaagact agaggccagg    2640
gcagcaaggg acctgctcat catattccaa cccagccacg actgccatgt aaggttgtgc    2700
agggtgtgta ctgcacaagg acattgtatg cagggagcac tgttcacatc atagataaag    2760
ctgatttgta tatttattat gacaatttct ggcagatgta ggtaaagagg aaaaggatcc    2820
ttttcctaat tcacacaaag actccttgtg gactggctgt gccccctgatg cagcctgtgg    2880
cttggagtgg ccaaatagga gggagactgt ggtaggggca gggaggcaac actgctgtcc    2940
acatgacctc catttcccaa agtcctctgc tccagcaact gcccttccag gtgggtgtgg    3000
gacacctggg agaaggtctc caagggaggg tgcagccctc ttgcccgcac ccctccctgc    3060
ttgcacactt ccccatcttt gatccttctg agctccacct ctggtggctc ctcctaggaa    3120
accagctcgt gggctgggaa tgggggagag aagggaaaag atccccaaga ccccctgggg    3180
tgggatctga gctcccacct cccttcccac ctactgcact tccccccttc ccgccttcca    3240
aaacctgctt ccttcagttt gtaaagtcgg tgattatatt tttgggggct ttcctttttat    3300
tttttaaatg taaaatttat ttatattccg tatttaaagt tgtaaaaaaa aataaccaca    3360
aaacaaaacc aaatgaaaaa aaaaaaaaaa aaa                                3393
```

<210> SEQ ID NO 2
<211> LENGTH: 241
<212> TYPE: PRT
<213> ORGANISM: Homo sapiens

<400> SEQUENCE: 2

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 3
<211> LENGTH: 87
<212> TYPE: DNA
<213> ORGANISM: Simian virus 40

<400> SEQUENCE: 3
atgctttgca tacttctgcc tgctggggag cctgggact ttccacaccc taactgacac      60
acattccaca gctggttggt acctgca                                         87

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gggtgtgaac cacgagaaat                                                 20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ccttccacaa tgccaaagtt                                           20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cttgactgtg gttactgctg                                           20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gagcgtaatc taccatggag                                           20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tggaagtggc ccatttagag                                           20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tgacgctttt ctcgtttgtg                                           20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cctcaaggga gtggagattg                                           20

<210> SEQ ID NO 11
<211> LENGTH: 20
<212> TYPE: DNA
<213> ORGANISM: Artificial Sequence
<220> FEATURE:

<223> OTHER INFORMATION: Primer

<400> SEQUENCE: 11
gactacgttt ggcccttctg                                               20

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
agctcactat ggctccagtc c                                             21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gcgtatggct tctttgtgcc t                                             21

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ccaagaaggc acagacagaa                                               20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
atactgggat gaggaatgcg                                               20

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
ggtgatagct tggcttatgg actg                                          24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
gctcttcatg tgagaggtga ggtc                                          24

```
<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gagcggagag tactggatcg                                            20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tactcgaacg ggaatccatc                                            20

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
cagcatcgct ctgttcctgt a                                          21

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
ctgcgttttc atggagtctc a                                          21

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
acccagaaac tggtcatcag c                                          21

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
ctgcaataca cacactcatc act                                        23

<210> SEQ ID NO 24
<211> LENGTH: 21
<212> TYPE: DNA
<213> ORGANISM: Artificial Sequence
<220> FEATURE:
<223> OTHER INFORMATION: Primer
```

<400> SEQUENCE: 24
ggcttggctt gggatgattc t                                            21

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
gagggtctgg caggtactc                                               19

<210> SEQ ID NO 26
<211> LENGTH: 7385
<212> TYPE: DNA
<213> ORGANISM: Artificial Sequence
<220> FEATURE:
<223> OTHER INFORMATION: Regulatory element

<400> SEQUENCE: 26
caggtggcac ttttcgggga aatgtgcgcg gaacccctat ttgtttattt ttctaaatac    60
attcaaatat gtatccgctc atgagacaat aaccctgata aatgcttcaa taatattgaa   120
aaaggaagag tatgagtatt caacatttcc gtgtcgccct tattcccttt tttgcggcat   180
tttgccttcc tgttttgct cacccagaaa cgctggtgaa agtaaaagat gctgaagatc    240
agttgggtgc acgagtgggt tacatcgaac tggatctcaa cagcggtaag atccttgaga   300
gttttcgccc cgaagaacgt tttccaatga tgagcacttt taaagttctg ctatgtggcg   360
cggtattatc ccgtattgac gccgggcaag agcaactcgg tcgccgcata cactattctc   420
agaatgactt ggttgagtac tcaccagtca cagaaaagca tcttacggat ggcatgacag   480
taagagaatt atgcagtgct gccataacca tgagtgataa cactgcggcc aacttacttc   540
tgacaacgat cggaggaccg aaggagctaa ccgcttttt gcacaacatg ggggatcatg    600
taactcgcct tgatcgttgg gaaccggagc tgaatgaagc cataccaaac gacgagcgtg   660
acaccacgat gcctgtagca atggcaacaa cgttgcgcaa actattaact ggcgaactac   720
ttactctagc ttcccggcaa caattaatag actggatgga ggcggataaa gttgcaggac   780
cacttctgcg ctcggccctt ccggctggct ggtttattgc tgataaatct ggagccggtg   840
agcgtgggtc tcgcggtatc attgcagcac tggggccaga tggtaagccc tcccgtatcg   900
tagttatcta cacgacgggg agtcaggcaa ctatggatga acgaaataga cagatcgctg   960
agataggtgc ctcactgatt aagcattggt aactgtcaga ccaagtttac tcatatatac  1020
tttagattga tttaaaactt catttttaat ttaaaaggat ctaggtgaag atccttttg   1080
ataatctcat gaccaaaatc ccttaacgtg agttttcgtt ccactgagcg tcagaccccg  1140
tagaaaagat caaaggatct tcttgagatc ctttttttct gcgcgtaatc tgctgcttgc  1200
aaacaaaaaa accaccgcta ccagcggtgg tttgtttgcc ggatcaagag ctaccaactc  1260
tttttccgaa ggtaactggc ttcagcagag cgcagatacc aaatactgtc cttctagtgt  1320
agccgtagtt aggccaccac ttcaagaact ctgtagcacc gcctacatac ctcgctctgc  1380
taatcctgtt accagtggct gctgccagtg gcgataagtc gtgtcttacc gggttggact  1440
caagacgata gttaccggat aaggcgcagc ggtcgggctg aacggggggt tcgtgcacac  1500
agcccagctt ggagcgaacg acctacaccg aactgagata cctacagcgt gagctatgag  1560
aaagcgccac gcttcccgaa gggagaaagg cggacaggta tccggtaagc ggcagggtcg  1620

```
gaacaggaga gcgcacgagg gagcttccag ggggaaacgc ctggtatctt tatagtcctg    1680
tcgggtttcg ccacctctga cttgagcgtc gattttgtg atgctcgtca ggggggcgga     1740
gcctatggaa aaacgccagc aacgcggcct ttttacggtt cctggccttt tgctggcctt    1800
ttgctcacat gttctttcct gcgttatccc ctgattctgt ggataaccgt attaccgcct    1860
ttgagtgagc tgataccgct cgccgcagcc gaacgaccga gcgcagcgag tcagtgagcg    1920
aggaagcgga gagcgccca atacgcaaac cgcctctccc cgcgcgttgg ccgattcatt     1980
aatgcagctg gcacgacagg tttcccgact ggaaagcggg cagtgagcgc aacgcaatta    2040
atgtgagtta gctcactcat taggcacccc aggctttaca ctttatgctt ccggctcgta    2100
tgttgtgtgg aattgtgagc ggataacaat ttcacacagg aaacagctat gaccatgatt    2160
acgccaagcg cgcaattaac cctcactaaa gggaacaaaa gctggagctg caagcttaat    2220
gtagtcttat gcaatactct tgtagtcttg caacatggta acgatgagtt agcaacatgc    2280
cttacaagga gagaaaaagc accgtgcatg ccgattggtg gaagtaaggt ggtacgatcg    2340
tgccttatta ggaaggcaac agacgggtct gacatggatt ggacgaacca ctgaattgcc    2400
gcattgcaga gatattgtat ttaagtgcct agctcgatac aataaacggg tctctctggt    2460
tagaccagat ctgagcctgg gagctctctg gctaactagg gaacccactg cttaagcctc    2520
aataaagctt gccttgagtg cttcaagtag tgtgtgcccg tctgttgtgt gactctggta    2580
actagagatc cctcagaccc ttttagtcag tgtggaaaat ctctagcagt ggcgcccgaa    2640
cagggacctg aaagcgaaag gaaaccagag gctctctcga cgcaggactc ggcttgctga    2700
agcgcgcacg gcaagaggcg aggggcggcg actggtgagt acgccaaaaa ttttgactag    2760
cggaggctag aaggagagag atgggtgcga gagcgtcagt attaagcggg ggagaattag    2820
atcgcgatgg gaaaaaattc ggttaaggcc agggggaaag aaaaaatata aattaaaaca    2880
tatagtatgg gcaagcaggg agctagaacg attcgcagtt aatcctggcc tgttagaaac    2940
atcagaaggc tgtagacaaa tactgggaca gctacaacca tcccttcaga caggatcaga    3000
agaacttaga tcattatata atacagtagc aaccctctat tgtgtgcatc aaaggataga    3060
gataaaagac accaaggaag ctttagacaa gatagaggaa gagcaaaaca aaagtaagac    3120
caccgcacag caagcggccg ctgatcttca gacctggagg aggagatatg agggacaatt    3180
ggagaagtga attatataaa tataaagtag taaaaattga accattagga gtagcaccca    3240
ccaaggcaaa gagaagagtg gtgcagagag aaaaaagagc agtgggaata ggagctttgt    3300
tccttgggtt cttgggagca gcaggaagca ctatgggcgc agcctcaatg acgctgacgg    3360
tacaggccag acaattattg tctggtatag tgcagcagca gaacaatttg ctgagggcta    3420
ttgaggcgca acagcatctg ttgcaactca cagtctgggg catcaagcag ctccaggcaa    3480
gaatcctggc tgtggaaaga tacctaaagg atcaacagct cctggggatt tggggttgct    3540
ctggaaaact catttgcacc actgctgtgc cttggaatgc tagttggagt aataaatctc    3600
tggaacagat ttggaatcac acgacctgga tggagtggga cagagaaatt aacaattaca    3660
caagcttaat acactcctta attgaagaat cgcaaaacca gcaagaaaag aatgaacaag    3720
aattattgga attagataaa tgggcaagtt tgtggaattg gtttaacata acaaattggc    3780
tgtggtatat aaaattattc ataatgatag taggaggctt ggtaggttta agaatagttt    3840
ttgctgtact ttctatagtg aatagagtta ggcaggata ttcaccatta tcgtttcaga    3900
cccacctccc aaccccgagg ggacccgaca ggcccgaagg aatagaagaa gaaggtggag    3960
```

| | |
|---|---|
| agagagacag agacagatcc attcgattag tgaacggatc tcgacggtat cggttaactt | 4020 |
| ttaaaagaaa aggggggatt gggggtaca gtgcagggga aagaatagta gacataatag | 4080 |
| caacagacat acaaactaaa gaattacaaa aacaaattac aaaaattcaa aattttatcg | 4140 |
| atcacgagac tagcctcgag aagcttgata tcgaattccc acggggttgg ggttgcgcct | 4200 |
| tttccaaggc agccctgggt tgcgcaggg acgcggctgc tctgggcgtg gttccgggaa | 4260 |
| acgcagcggc gccgaccctg gtctcgcac attcttcacg tccgttcgca gcgtcacccg | 4320 |
| gatcttcgcc gctacccttg tgggcccccc ggcgacgctt cctgctccgc ccctaagtcg | 4380 |
| ggaaggttcc ttgcggttcg cggcgtgccg gacgtgacaa acggaagccg cacgtctcac | 4440 |
| tagtaccctc gcagacggac agcgccaggg agcaatggca gcgcgccgac cgcgatgggc | 4500 |
| tgtggccaat agcggctgct cagcggggcg cgccgagagc agcggccggg aaggggcggt | 4560 |
| gcgggaggcg gggtgtgggg cggtagtgtg ggccctgttc ctgcccgcgc ggtgttccgc | 4620 |
| attctgcaag cctccggagc gcacgtcggc agtcggctcc ctcgttgacc gaatcaccga | 4680 |
| cctctctccc caggggatc cgcgatcgcc atgaatcgct gctgggcgct cttcctgtct | 4740 |
| ctctgctgct acctgcgtct ggtcagcgcc gaggggacc ccattcccga ggagctttat | 4800 |
| gagatgctga gtgaccactc gatccgctcc tttgatgatc tccaacgcct gctgcacgga | 4860 |
| gaccccggag aggaagatgg ggccgagttg gacctgaaca tgacccgctc ccactctgga | 4920 |
| ggcgagctgg agagcttggc tcgtggaaga aggagcctgg gttccctgac cattgctgag | 4980 |
| ccggccatga tcgccgagtg caagacgcgc accgaggtgt tcgagatctc ccggcgcctc | 5040 |
| atagaccgca ccaacgccaa cttcctggtg tggccgccct gtgtggaggt gcagcgctgc | 5100 |
| tccggctgct gcaacaaccg caacgtgcag tgccgcccca cccaggtgca gctgcgacct | 5160 |
| gtccaggtga aaagatcga gattgtgcgg aagaagccaa tctttaagaa ggccacggtg | 5220 |
| acgctggaag accacctggc atgcaagtgt gagacagtgg cagctgcacg gcctgtgacc | 5280 |
| cgaagcccgg ggggttccca ggagcagcga gccaaaacgc cccaaactcg ggtgaccatt | 5340 |
| cggacggtgc gagtccgccg gccccccaag ggcaagcacc ggaaattcaa gcacacgcat | 5400 |
| gacaagacgg cactgaagga gacccttgga gcctaggttt aaacgtcgac aatcaacctc | 5460 |
| tggattacaa aatttgtgaa agattgactg gtattcttaa ctatgttgct ccttttacgc | 5520 |
| tatgtggata cgctgcttta atgcctttgt atcatgctat tgcttcccgt atggctttca | 5580 |
| ttttctcctc cttgtataaa tcctggttgc tgtctcttta tgaggagttg tggcccgttg | 5640 |
| tcaggcaacg tggcgtggtg tgcactgtgt ttgctgacgc aaccccccact ggttggggca | 5700 |
| ttgccaccac ctgtcagctc ctttccggga ctttcgcttt cccctccct attgccacgg | 5760 |
| cggaactcat cgccgcctgc cttgcccgct gctggacagg ggctcggctg ttgggcactg | 5820 |
| acaattccgt ggtgttgtcg gggaagctga cgtccttttcc atggctgctc gcctgtgttg | 5880 |
| ccacctggat tctgcgcggg acgtccttct gctacgtccc ttcggccctc aatccagcgg | 5940 |
| accttccttc ccgcggcctg ctgccggctc tgcggcctct tccgcgtctt cgccttcgcc | 6000 |
| ctcagacgag tcggatctcc ctttgggccg cctccccgcc tggaattcga gctcggtacc | 6060 |
| tttaagacca atgacttaca aggcagctgt agatcttagc cacttttaa aagaaagggg | 6120 |
| gggactggaa gggctaattc actcccaacg aagacaagat ctgcttttttg cttgtactgg | 6180 |
| gtctctctgg ttagaccaga tctgagcctg ggagctctct ggctaactag ggaacccact | 6240 |
| gcttaagcct caataaagct tgccttgagt gcttcaagta gtgtgtgccc gtctgttgtg | 6300 |
| tgactctggt aactagagat ccctcagacc cttttagtca gtgtggaaaa tctctagcag | 6360 |

```
tagtagttca tgtcatctta ttattcagta tttataactt gcaaagaaat gaatatcaga      6420
gagtgagagg aacttgttta ttgcagctta taatggttac aaataaagca atagcatcac      6480
aaatttcaca aataaagcat ttttttcact gcattctagt tgtggtttgt ccaaactcat      6540
caatgtatct tatcatgtct ggctctagct atcccgcccc taactccgcc cagttccgcc      6600
cattctccgc cccatggctg actaattttt tttatttatg cagaggccga ggccgcctcg      6660
gcctctgagc tattccagaa gtagtgagga ggcttttttg gaggcctagg cttttgcgtc      6720
gagacgtacc caattcgccc tatagtgagt cgtattacgc gcgctcactg gccgtcgttt      6780
tacaacgtcg tgactgggaa accctggcg ttacccaact taatcgcctt gcagcacatc      6840
cccctttcgc cagctggcgt aatagcgaag aggcccgcac cgatcgccct cccaacagt      6900 tgcgcagcct gaatggcgaa tggcgcgacg cgccctgtag cggcgcatta agcgcggcgg      6960
gtgtggtggt tacgcgcagc gtgaccgcta cacttgccag cgccctagcg cccgctcctt      7020
tcgctttctt cccttccttt ctcgccacgt tcgccggctt tccccgtcaa gctctaaatc      7080
gggggctccc tttagggttc cgatttagtg ctttacggca cctcgacccc aaaaaacttg      7140
attagggtga tggttcacgt agtgggccat cgccctgata acggttttt cgcccttttga      7200 cgttggagtc cacgttcttt aatagtggac tcttgttcca aactggaaca cactcaacc      7260 ctatctcggt ctattctttt gatttataag gattttgcc gatttcggcc tattggttaa      7320
aaaatgagct gatttaacaa aaatttaacg cgaattttaa caaaatatta acgtttacaa      7380
tttcc      7385

<210> SEQ ID NO 27
<211> LENGTH: 515
<212> TYPE: DNA
<213> ORGANISM: Artificial Sequence
<220> FEATURE:
<223> OTHER INFORMATION: Promoter

<400> SEQUENCE: 27
ccacggggtt ggggttgcgc cttttccaag gcagccctgg gtttgcgcag ggacgcggct       60
gctctgggcg tggttccggg aaacgcagcg gcgccgaccc tgggtctcgc acattcttca      120
cgtccgttcg cagcgtcacc cggatcttcg ccgctaccct tgtgggcccc ccggcgacgc      180
ttcctgctcc gccccctaagt cgggaaggtt ccttgcggtt cgcggcgtgc cggacgtgac      240
aaacggaagc cgcacgtctc actagtaccc tcgcagacgg acagcgccag ggagcaatgg      300
cagcgcgccg accgcgatgg gctgtggcca atagcggctg ctcagcgggg cgcgccgaga      360
gcagcggccg ggaaggggcg gtgcgggagg cggggtgtgg ggcggtagtg tgggccctgt      420
tcctgcccgc gcggtgttcc gcattctgca agcctccgga gcgcacgtcg gcagtcggct      480
ccctcgttga ccgaatcacc gacctctctc cccag                                515

<210> SEQ ID NO 28
<211> LENGTH: 1723
<212> TYPE: DNA
<213> ORGANISM: Artificial Sequence
<220> FEATURE:
<223> OTHER INFORMATION: Promoter

<400> SEQUENCE: 28
gtcgacattg attattgact agttattaat agtaatcaat tacggggtca ttagttcata       60
gcccatatat ggagttccgc gttacataac ttacggtaaa tggcccgcct ggctgaccgc      120
```

| | |
|---|---|
| ccaacgaccc ccgcccattg acgtcaataa tgacgtatgt tcccatagta acgccaatag | 180 |
| ggactttcca ttgacgtcaa tgggtggact atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atgggtcgag gtgagcccca cgttctgctt cactctcccc | 420 |
| atctcccccc cctccccacc cccaattttg tatttattta ttttttaatt attttgtgca | 480 |
| gcgatggggg cggggggggg ggggcgcgc gccaggcggg gcgggcggg gcgaggggcg | 540 |
| gggcggggcg aggcggagag gtgcggcggc agccaatcag agcggcgcgc tccgaaagtt | 600 |
| tccttttatg gcgaggcggc ggcggcggcg gccctataaa aagcgaagcg cgcggcgggc | 660 |
| gggagtcgct gcgttgcctt cgccccgtgc cccgctccgc gccgcctcgc gccgcccgcc | 720 |
| ccggctctga ctgaccgcgt tactcccaca ggtgagcggg cgggacggcc cttctcctcc | 780 |
| gggctgtaat tagcgcttgg tttaatgacg gctcgtttct tttctgtggc tgcgtgaaag | 840 |
| ccttaaaggg ctccggagg gccctttgtg cgggggggag cggctcgggg ggtgcgtgcg | 900 |
| tgtgtgtgtg cgtggggagc gccgcgtgcg gcccgcgctg cccggcggct gtgagcgctg | 960 |
| cgggcgcggc gcgggctttt gtgcgctccg cgtgtgcgcg aggggagcgc ggccggggc | 1020 |
| ggtgccccgc ggtgcggggg ggctgcgagg ggaacaaagg ctgcgtgcgg ggtgtgtgcg | 1080 |
| tgggggggtg agcaggggt gtgggcgcgg cggtcgggct gtaaccccc cctgcacccc | 1140 |
| cctccccgag ttgctgagca cggcccggct tcgggtgcgg ggctccgtgc ggggcgtggc | 1200 |
| gcggggctcg ccgtgccggg cggggggtgg cgcaggtgg gggtgccggg cggggcgggg | 1260 |
| ccgcctcggg ccggggaggg ctcggggag gggcgcggcg gccccggagc gccggcggct | 1320 |
| gtcgaggcgc ggcgagccgc agccattgcc ttttatggta atcgtgcgag agggcgcagg | 1380 |
| gacttccttt gtcccaaatc tggcggagcc gaaatctggg aggcgccgcc gcaccccctc | 1440 |
| tagcgggcgc gggcgaagcg gtgcggcgcc ggcaggaagg aaatgggcgg gagggccttt | 1500 |
| cgtgcgtcgc cgcgccgccg tccccttctc catctccagc ctcggggctg ccgcagggg | 1560 |
| acggctgcct tcgggggga cggggcaggg cggggttcgg cttctggcgt gtgaccggcg | 1620 |
| gctctagagc ctctgctaac catgttcatg ccttcttctt tttcctacag ctcctgggca | 1680 |
| acgtgctggt tattgtgctg tctcatcatt ttggcaaaga att | 1723 |

<210> SEQ ID NO 29
<211> LENGTH: 1178
<212> TYPE: DNA
<213> ORGANISM: Artificial Sequence
<220> FEATURE:
<223> OTHER INFORMATION: Promoter

<400> SEQUENCE: 29

| | |
|---|---|
| ggctccggtg cccgtcagtg ggcagagcgc acatcgccca cagtccccga gaagttgggg | 60 |
| ggaggggtcg gcaattgaac cggtgcctag agaaggtggc gcgggtaaa ctggaaagt | 120 |
| gatgtcgtgt actggctccg ccttttccc gagggtgggg gagaaccgta tataagtgca | 180 |
| gtagtcgccg tgaacgttct ttttcgcaac gggtttgccg ccagaacaca ggtaagtgcc | 240 |
| gtgtgtggtt cccgcgggcc tggcctcttt acgggttatg gcccttgcgt gccttgaatt | 300 |
| acttccactg gctgcagtac gtgattcttg atcccgagct tcgggttgga agtgggtggg | 360 |
| agagttcgag gccttgcgct taaggagccc cttcgcctcg tgcttgagtt gaggcctggc | 420 |
| ctgggcgctg gggccgccgc gtgcgaatct ggtggcacct tcgcgcctgt ctcgctgctt | 480 |

```
tcgataagtc tctagccatt taaaattttt gatgacctgc tgcgacgctt tttttctggc        540
aagatagtct tgtaaatgcg ggccaagatc tgcacactgg tatttcggtt tttgggggccg       600 cgggcggcga cggggcccgt gcgtcccagc gcacatgttc ggcgaggcgg ggcctgcgag        660
cgcggccacc gagaatcgga cggggggtagt ctcaagctgg ccggcctgct ctggtgcctg      720
gcctcgcgcc gccgtgtatc gccccgccct gggcggcaag gctggcccgg tcggcaccag       780
ttgcgtgagc ggaaagatgg ccgcttcccg gccctgctgc agggagctca aaatggagga       840
cgcggcgctc gggagagcgg gcgggtgagt cacccacaca aaggaaaagg gcctttccgt       900
cctcagccgt cgcttcatgt gactccacgg agtaccgggc gccgtccagg cacctcgatt       960
agttctcgag cttttggagt acgtcgtctt taggttgggg ggaggggttt tatgcgatgg      1020
agtttcccca cactgagtgg gtggagactg aagttaggcc agcttggcac ttgatgtaat     1080
tctccttgga atttgcccttt tttgagtttg gatcttggtt cattctcaag cctcagacag    1140
tggttcaaag ttttttttctt ccatttcagg tgtcgtga                             1178

<210> SEQ ID NO 30
<211> LENGTH: 422
<212> TYPE: DNA
<213> ORGANISM: Artificial Sequence
<220> FEATURE:
<223> OTHER INFORMATION: Promoter

<400> SEQUENCE: 30
gctagctgca gtaacgccat tttgcaaggc atggaaaaat accaaaccaa gaatagagaa         60
gttcagatca agggcgggta catgaaaata gctaacgttg ggccaaacag gatatctgcg       120
gtgagcagtt tcggccccgg cccgggggcca agaacagatg gtcaccgcag tttcggcccc      180
ggcccgaggc caagaacaga tggtccccag atatggccca accctcagca gtttcttaag       240
acccatcaga tgtttccagg ctcccccaag gacctgaaat gaccctgcgc cttatttgaa       300
ttaaccaatc agcctgcttc tcgcttctgt tcgcgcgctt ctgcttcccg agctctataa       360
aagagctcac aaccccctcac tcggcgcgcc agtcctccga cagactgagt cgcccgggta      420
cc                                                                      422

<210> SEQ ID NO 31
<211> LENGTH: 630
<212> TYPE: DNA
<213> ORGANISM: Artificial Sequence
<220> FEATURE:
<223> OTHER INFORMATION: Promoter

<400> SEQUENCE: 31
agctagcgtg ccaacagatg aggttcacaa tctcttccac aaaacatgca gttaaatatc         60
tgaggatatt cagggacttg gatttggtgg caggagatca acataaacca agacaaggaa       120
gaagtcaaag aaatgaatca agtagattct ctgggtatata aggtaggggg attgggggggt      180 tggatagtgc agagtatggt actggcctaa ggcactgagg atcatccttt tcccacaccc       240
accagagaag gcttaggctc ccgagtcaac agggcattca ccgcctgggg cgcctgagtc       300
atcaggacac tgccaggaga cacagaaccc tagatgccct gcagaatcct tcctgttacg       360
gtccccctcc ctgaaacatc cttcattgca atatttccag gaaaggaagg gggctggctc       420
ggaggaagag aggtggggag gtgatcaggg ttcacagagg agggaactga atgacatccc       480
aggattacat aaactgtcag aggcagccga agagttcaca agtgtgaagc ctggaagccg       540
```

```
gcgggtgccg ctgtgtagga agaagctaa  agcacttcca gagcctgtcc ggagctcaga      600
ggttcggaag acttatcgac cgcgatcgcc                                       630
```

```
<210> SEQ ID NO 32
<211> LENGTH: 815
<212> TYPE: DNA
<213> ORGANISM: Artificial Sequence
<220> FEATURE:
<223> OTHER INFORMATION: Promoter

<400> SEQUENCE: 32
gccaagaaca tcttaagtca cagaaacatt agtttttgga agcagggttt gctgtaacta       60
tagtagaaat gacattctga ttccactcct agcttcacaa ggatatctgt gaaagatttg      120
gggcaaaact gttaagctgt ctgaaagtgc ttttgcataa gaaatgggtt ttactgctaa      180
aactgtcata ttgctgagtt tgaatgccc  taatggtaaa tgatactggg ttgccaaaaa      240
taaccagatt agtagttttt tcattcattt ggccgtctca gtaagtcaaa tattgatact      300
ttctactaag tcatcttgcc aacacccatt tgttatact  tatgctgaat ctgtttgtca      360
tctcttaagt aagaaaatta ttgattattt tgtggggatt taatttaaaa aaaatggtaa      420
tggatactgt aaaggagcat tatttggatg gtttaaaaac atcttccttg atgggaaaat      480
cttttaaaag gctttctaac ttggtgtaat tacttgaatt aaggaagtgc aatgccattc      540
tactgactta gaacaacttt tttgacttcc tgcaaagagg acccttacag tatttttgga      600
gaagttagta aaaccgaatc tgacatcatc acctagcagt tcatgcagct agcaagtggt      660
ttgttcttag ggtaacagag gaggaaattg ttcctcgtct gataagacaa cagtggagag      720
tatgcattta tttatttact tttacatttt tgattcgttt ttacagagaa aaacttctac      780
agagataaca attattttgc ttttcagaag gacgc                                 815
```

```
<210> SEQ ID NO 33
<211> LENGTH: 2135
<212> TYPE: DNA
<213> ORGANISM: Artificial Sequence
<220> FEATURE:
<223> OTHER INFORMATION: Promoter

<400> SEQUENCE: 33
ggctgggtgt gttttttgtct tgcatgaaga cttctctgca gagggcctgg cttctctagc      60
acaagcctgg caacatctgg tacctctaac tctaagatta ctcaagtaca ctgtagccct     120
ctcccagaag agttaatgtg agtggtctgt cagtagaatg ggcaggagtc caccactaag     180
ggaagctagc tccccaacaa tggggctggg tggaaactgg aggactcatg agaattccta     240
gtttaagact tttagagaaa cagtgcacgg cactgtggtt atatggcctt tccctccaaa     300
gagaaggtga tggccccgtt gtcatcctgg agtaggata  atgttggccc aggagccctg     360
gcaataaata gagtcagaag agcaaaacag cataggtct  gtgataatgg cagaactct      420 ctatactcag aagggaggac tgtcacctgg ggttccagcc atgactccct cctgttctcc     480
gccaagcaca agtggtctca gaagatacta gaatatagag gatacagagg atttactgaa     540
agagggactc cgtgtactgc ttttatgatg gggtgagatt tggtggtgac taagctgctc     600
agaatttatg catattcctg taagtgacct cacccatcct ctgggggaaa aaagcctca      660 taacctcatt gggtggtgac attggcaggg tttatcactt ggatctttcc ttgccgcttt     720
ttctttgttt gcagaggctt gctgtctcct gctctttctt tcacatacac ttcttcatgc     780
atgagccaat accgagcaca gcatgtgaca gaattagaga gacaacattt cttgcttgct     840
```

```
ctcttcctct taccactgtg ctgggttatg cggtgttgga ggcaaactgt tgcttatat      900
gatatattat agggtaagaa ggaaggggtt tttagtggtg ctcgggcaga ggccatggag      960
tgtaagcagc cttccctgct taagtggggt gcgctcagct tcactgatgc tgtggtccat     1020
tttgggactc agttgtcctg tgagcacagc tgttcatttg ctgtggtatc atctcaggat     1080
gatttccagc tcaggtctct acctctgtcc agcacacaca gccccataca tccccaaaca     1140
catcagacac tgcttggtaa cttccatccc agttgccagt tagttcttgc tcaggactc     1200
tcactttgtg gatgcaagag cctactgggg gcttgctcac cagagccagt ctttaagtat     1260
ttgtaaattg ttttcctgct tataggaagg agggccattg gctctgagcc actgcaaacc     1320
ataccttcta tttagacaca gaaaaaagcc aggtagtgga ggcagaagta tcagcggctg     1380
ttgtgcaccc ctttgatagc tgtgtgttgg agccagcctg ttctactgag caagtcctag     1440
gacagccaaa gctacacaga gaaactttgt ctcaaaaaaa aaaaaaaaag tcaaaaaaaa     1500
acccaaaata aacaaacaaa aaacacgaag ctaaacaaaa caaaaactag taaagggctg     1560
agcaacttga cttcttccct tgctttctaa ttggcaagca caagtcaact gtggcctctg     1620
gccctcggcc ctctcagttc tcctgcacca tggttcctcc ccaactgcta taaatctggc     1680
ttgatcaggt cacaaacaaa tcttgctacc tcttaaccaa taaacatgat ggcctggaaa     1740
aggttaagta ctgaaacccc tccctcttca ggatgccagc tgggaggagc tgaaggaaat     1800
taaagtactt cagtccacat ctgacagaac ttgccactgt gcctgcaacc ttgtctgaga     1860
ggaagtaagg actggtgtga ggagggagct gctaggtgac aaaggaaga gccctcagga      1920
tagggctggg gttgggagtg tgggattagg aaggaagagc tgggtgggtg gtgggtgaga     1980
gaagtaggca gacatgtatt cctcagggaa agctgtgtgg agggttggag ggagggaaga     2040
tcggatgcct gagctctgtg agagcccagg gatgtgattg ggggtctatt aattggctcc     2100
aacttccaag gtttatctg tgcagccctt ctctg                                 2135

<210> SEQ ID NO 34
<211> LENGTH: 1609
<212> TYPE: DNA
<213> ORGANISM: Artificial Sequence
<220> FEATURE:
<223> OTHER INFORMATION: Promoter

<400> SEQUENCE: 34
gatctctatt tatttagcaa taatagagaa agcatttaag agaataaagc aatggaaata       60
agaaatttgt aaatttcctt ctgataacta gaaatagagg atccagtttc ttttggttaa      120
cctaaatttt atttcatttt attgttttat tttattttat tttattttat tttgtgtaat      180
cgtagtttca gagtgttaga gctgaaagga agaagtagga gaaacatgca agtaaaagt       240
ataacacttt ccttactaaa ccgacatggg tttccaggta ggggcaggat tcaggatgac      300
tgacagggcc cttagggaac actgagaccc tacgctgacc tcataaatgc ttgctacctt      360
tgctgtttta attacatctt ttaatagcag gaagcagaac tctgcacttc aaaagttttt      420
cctcacctga ggagttaatt tagtacaagg ggaaaaagta caggggatg ggagaaaggc      480
gatcacgttg ggaagctata gagaaagaag agtaaatttt agtaaaggag gtttaaacaa      540
acaaaatata aagagaaata ggaacttgaa tcaaggaaat gattttaaaa cgcagtattc      600
ttagtggact agaggaaaaa aataatctga gccaagtaga agaccttttc ccctcctacc      660
cctactttct aagtcacaga ggcttttgt tcccccagac actcttgcag attagtccag      720
```

```
gcagaaacag ttagatgtcc ccagttaacc tcctatttga caccactgat taccccattg    780
atagtcacac tttgggttgt aagtgactt tatttttatt gtatttttga ctgcattaag    840
aggtctctag ttttttatct cttgtttccc aaaacctaat aagtaactaa tgcacagagc    900
acattgattt gtatttattc tatttttaga cataattat tagcatgcat gagcaaatta    960
agaaaaacaa caacaaatga atgcatatat atgtatatgt atgtgtgtat atatacacac   1020
atatatatat atatttttc ttttcttacc agaaggtttt aatccaaata aggagaagat   1080
atgcttagaa ccgaggtaga gttttcatcc attctgtcct gtaagtattt tgcatattct   1140
ggagacgcag gaagagatcc atctacatat cccaaagctg aattatggta gacaaaactc   1200
ttccactttt agtgcatcaa cttcttattt gtgtaataag aaaattggga aaacgatctt   1260
caatatgctt accaagctgt gattccaaat attacgtaaa tacacttgca aaggaggatg   1320
tttttagtag caatttgtac tgatggtatg gggccaagag atatatctta gagggagggc   1380
tgagggtttg aagtccaact cctaagccag tgccagaaga gccaaggaca ggtacggctg   1440
tcatcactta gacctcaccc tgtggagcca caccctaggg ttggccaatc tactcccagg   1500
agcagggagg gcaggagcca gggctgggca taaaagtcag ggcagagcca tctattgctt   1560
acatttgctt ctgacacaac tgtgttcact agcaacctca aacagacac              1609
```